(12) United States Patent
Osswald et al.

(10) Patent No.: US 11,246,927 B2
(45) Date of Patent: Feb. 15, 2022

(54) AGENTS FOR USE IN THE TREATMENT OF GLIOMA

(71) Applicant: DC EUROPA LIMITED, Cambridge (GB)

(72) Inventors: Matthias Osswald, Stuttgart (DE); Wolfgang Wick, Heidelberg (DE); Frank Winkler, Heidelberg (DE); Erik Jung, Heidelberg (DE); Jonas Blaes, Heßheim (DE)

(73) Assignee: DC EUROPA LIMITED, Cambridge (GB)

( * ) Notice: Subject to any disclaimer, the term of this patent is extended or adjusted under 35 U.S.C. 154(b) by 177 days.

(21) Appl. No.: 15/748,537

(22) PCT Filed: Jul. 6, 2016

(86) PCT No.: PCT/EP2016/001151
§ 371 (c)(1),
(2) Date: Jan. 29, 2018

(87) PCT Pub. No.: WO2017/020982
PCT Pub. Date: Feb. 9, 2017

(65) Prior Publication Data
US 2018/0221479 A1 Aug. 9, 2018

(30) Foreign Application Priority Data

Aug. 4, 2015 (EP) ..................................... 15002323

(51) Int. Cl.
| | | |
|---|---|---|
| *A61K 39/395* | (2006.01) |
| *A61K 31/155* | (2006.01) |
| *A61K 31/4985* | (2006.01) |
| *A61K 31/522* | (2006.01) |
| *C12N 15/113* | (2010.01) |
| *A61K 31/713* | (2006.01) |
| *A61K 31/495* | (2006.01) |
| *A61K 31/13* | (2006.01) |
| *A61K 31/7105* | (2006.01) |
| *A61P 35/00* | (2006.01) |
| *A61K 31/16* | (2006.01) |
| *A61K 31/497* | (2006.01) |
| *A61K 31/515* | (2006.01) |
| *A61K 31/5377* | (2006.01) |

(52) U.S. Cl.
CPC ........ *A61K 39/39558* (2013.01); *A61K 31/13* (2013.01); *A61K 31/155* (2013.01); *A61K 31/495* (2013.01); *A61K 31/4985* (2013.01); *A61K 31/522* (2013.01); *A61K 31/713* (2013.01); *A61K 31/7105* (2013.01); *A61P 35/00* (2018.01); *C12N 15/113* (2013.01); *C12N 15/1138* (2013.01); *A61K 31/16* (2013.01); *A61K 31/497* (2013.01); *A61K 31/515* (2013.01); *A61K 31/5377* (2013.01); *A61K 2300/00* (2013.01); *C12N 2310/14* (2013.01); *C12N 2330/50* (2013.01)

(58) Field of Classification Search
CPC .......... A61K 2300/00; A61K 39/39558; C12N 15/113; C12N 15/117; C12N 15/63; C12N 15/87
USPC .............. 424/9.1; 435/6.1, 91.1, 91.31, 458; 514/44 A; 536/23.1, 24.5
See application file for complete search history.

(56) References Cited

U.S. PATENT DOCUMENTS

2016/0287663 A1\* 10/2016 Gourdie .................. A61P 25/00

FOREIGN PATENT DOCUMENTS

| WO | 2003015713 A2 | 2/2003 |
| WO | 2009096615 A1 | 8/2009 |
| WO | 2015017034 A1 | 2/2015 |

OTHER PUBLICATIONS

Chuang, et al., "Role of Synaptojanin 2 in Glioma Cell Migration and Invasion", Cancer Research 64, 8271-8275 (2004).
Eyler, et al., "Glioma Stem Cell Proliferation and Tumor Growth Are Promoted by Nitric Oxide Synthase-2", Cell 146(1), 53-66 (2011).
Jacobs, et al., "Propentofylline decreases tumor growth in a rodent model of glioblastoma multiforme by a direct mechanism on microglia", Neuro-Oncology 14(2), 119-131 (2011).
Li, et al., "Mammalian diaphanous-related formin 1 is required for motility and invadopodia formation in human U87 glioblastoma cells", International Journal of Molecular Medicine 33, 383-391 (2013).
Osswald, et al., "Brain tumour cells interconnect to a functional and resistant network", Nature 528(7580), 93-98 (2015).
Patent Cooperation Treaty, International Searching Authority, Search Report and Written Opinion for PCT/EP2016/001151, 14 pages, dated Oct. 24, 2016.
Ren, et al., "AC1MMYR2 impairs high dose paclitaxel-induced tumor metastasis by targeting miR-21/CDK5 axis", Cancer Letters 362(2), 174-182 (2015).
Stylli, et al., "Invadopodia: At the cutting edge of tumour invasion", Journal of Clinical Neuroscience 15(7), 725-737 (2008).
Xie, et al., "Anesthetic pentobarbital inhibits proliferation and migration of malignant glioma cells", Cancer Letters 282(1), 35-42 (2009).
Zhang, et al., "Blockade of TGF-β signaling by the TGFβR-I kinase inhibitor LY2109761 enhances radiation response and prolongs survival in glioblastoma", Cancer Research 71(23), 7155-7167 (2011).

(Continued)

*Primary Examiner* — Jane J Zara
(74) *Attorney, Agent, or Firm* — Scully, Scott, Murphy & Presser, P.C.

(57) ABSTRACT

The present invention relates to agents for use in the treatment of glioma, in particular astrocytoma WHO II° and III°, as well as IV° (glioblastoma), in a subject.

1 Claim, 68 Drawing Sheets
Specification includes a Sequence Listing.

(56) References Cited

OTHER PUBLICATIONS

Avril T. et al., "Human Glioblastoma Stem-Like Cells are More Sensitive to Allogeneic NK and T Cell-Mediated Killing Compared With Serum-Cultured Glioblastoma Cells", Brain Pathology 22:159-174 (2012).

Garnier D. et al., "Glioblastoma Stem-Like Cells, Metabolic Strategy to Kill a Challenging Target", Frontiers in Oncology 9(118):1-18 (Mar. 2019).

Nishikawa M. et al., "Significance of Glioma Stem-Like Cells in the Tumor Periphery That Express High Levels of CD44 in Tumor Invasion, Early Progression, and Poor Prognosis in Glioblastoma", Stem Cells International 2018:5387041 (2018).

Wallenborn M. et al., "Molecular Analyses of Glioblastoma Stem-Like Cells and Glioblastoma Tissue", PLoS One 15(7):e0234986 (2020).

Yi Y. et al., "Glioblastoma Stem-Like Cells: Characteristics, Microenvironment, and Therapy", Frontiers in Pharmacology 7(477) (Dec. 2016).

\* cited by examiner

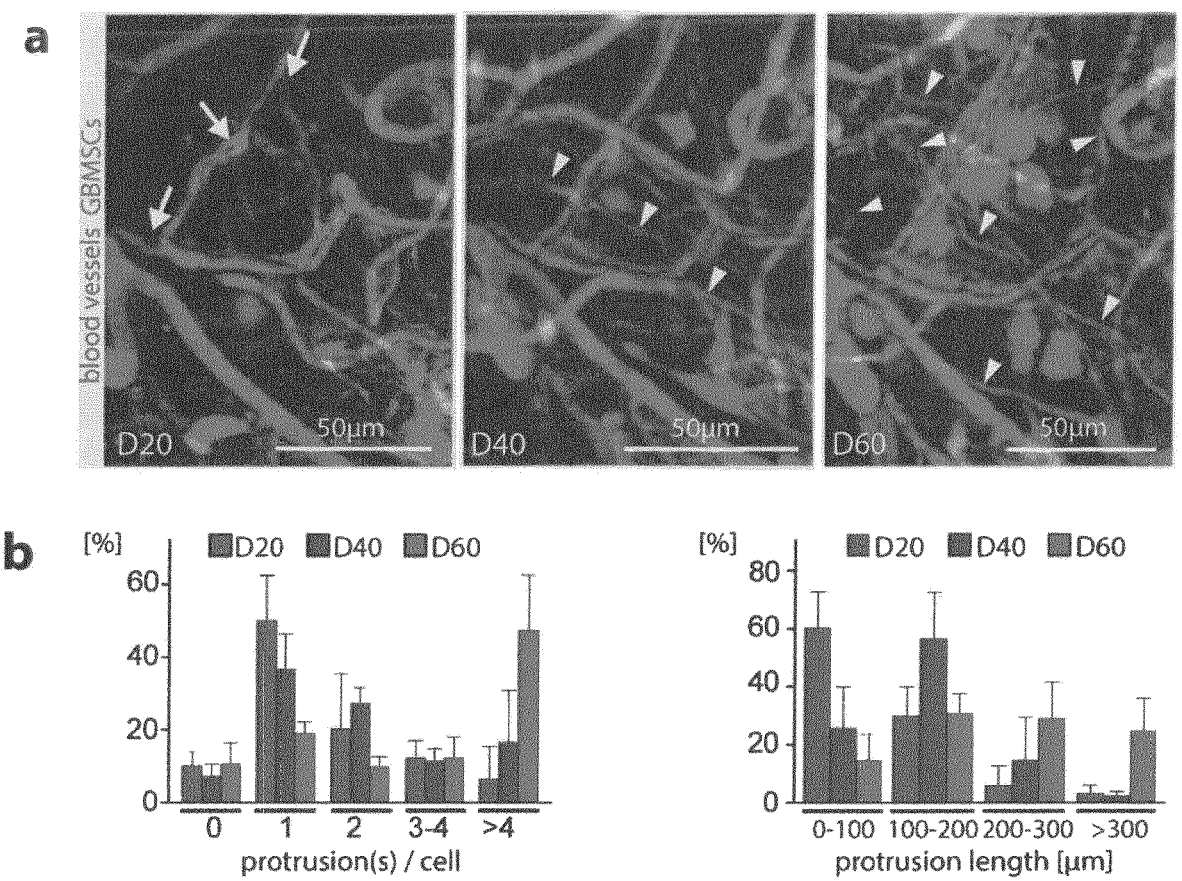
Figure 1 a, b

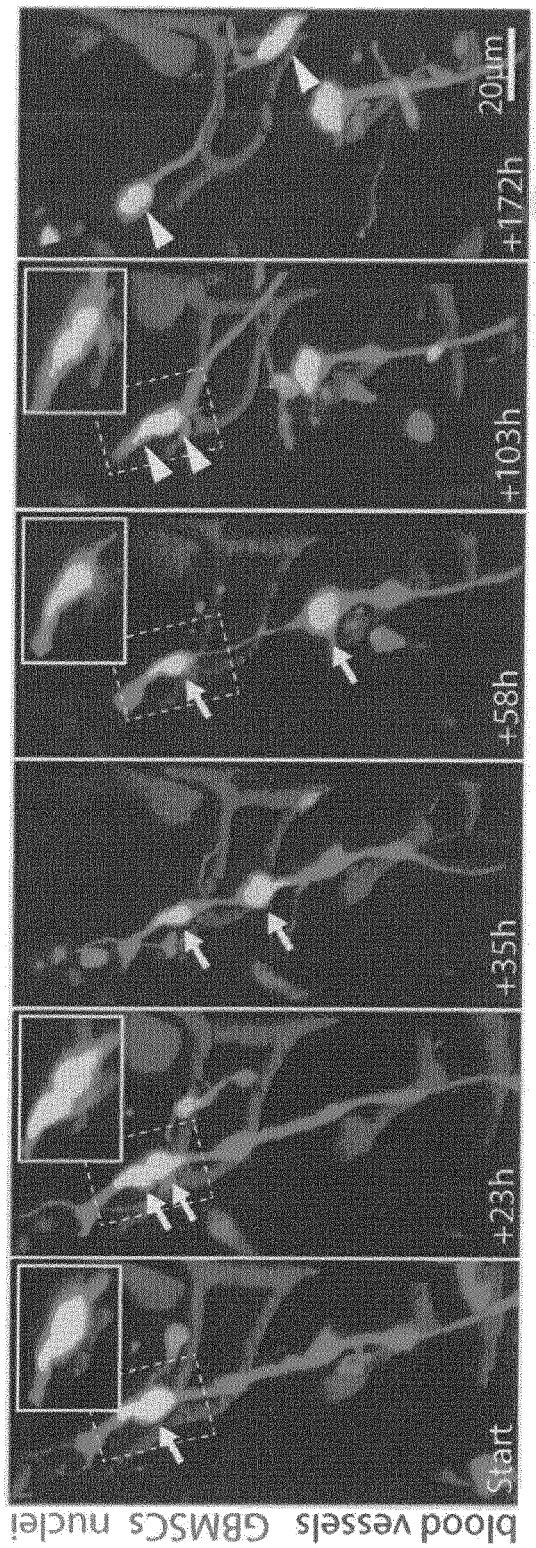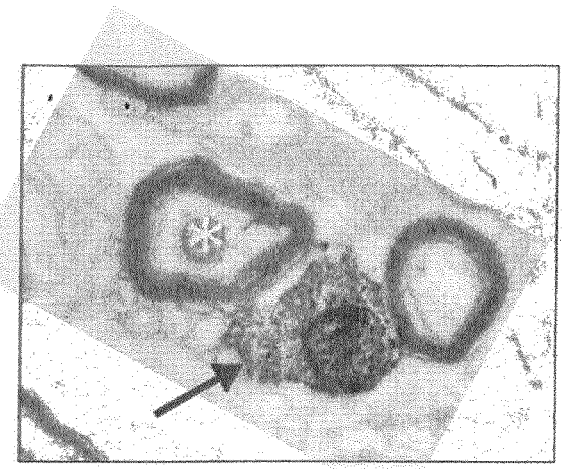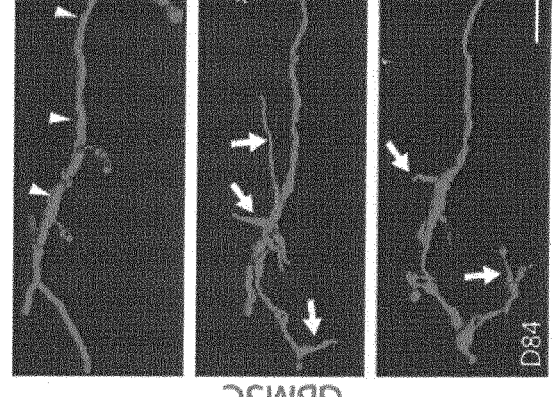
Figure 1 c, d, e, f

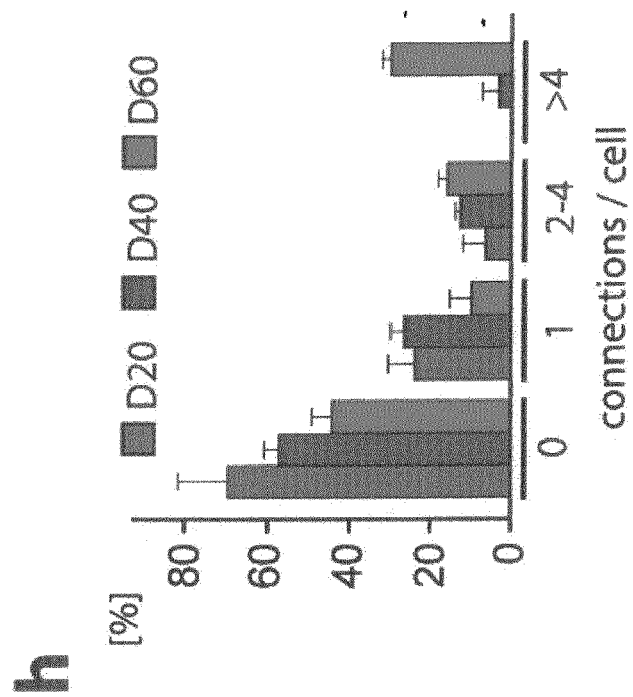
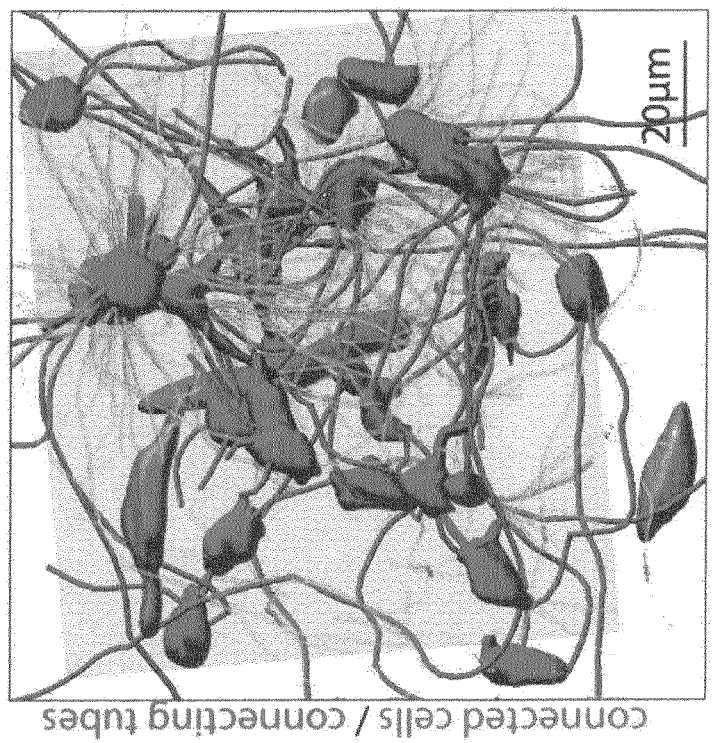
Figure 1 g, h

Figure 2:
Figure 2:
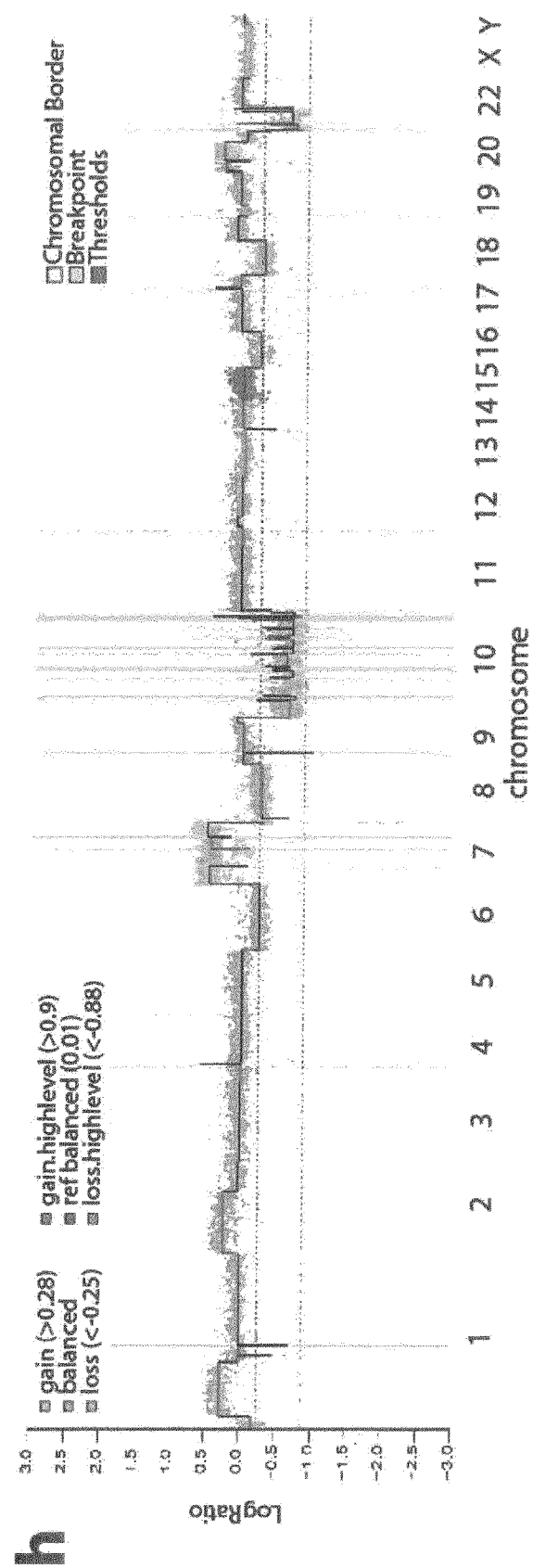
Figure 2:
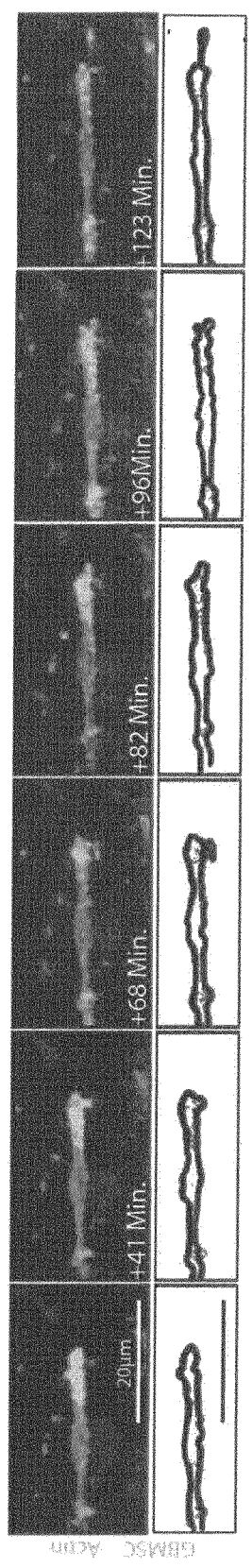

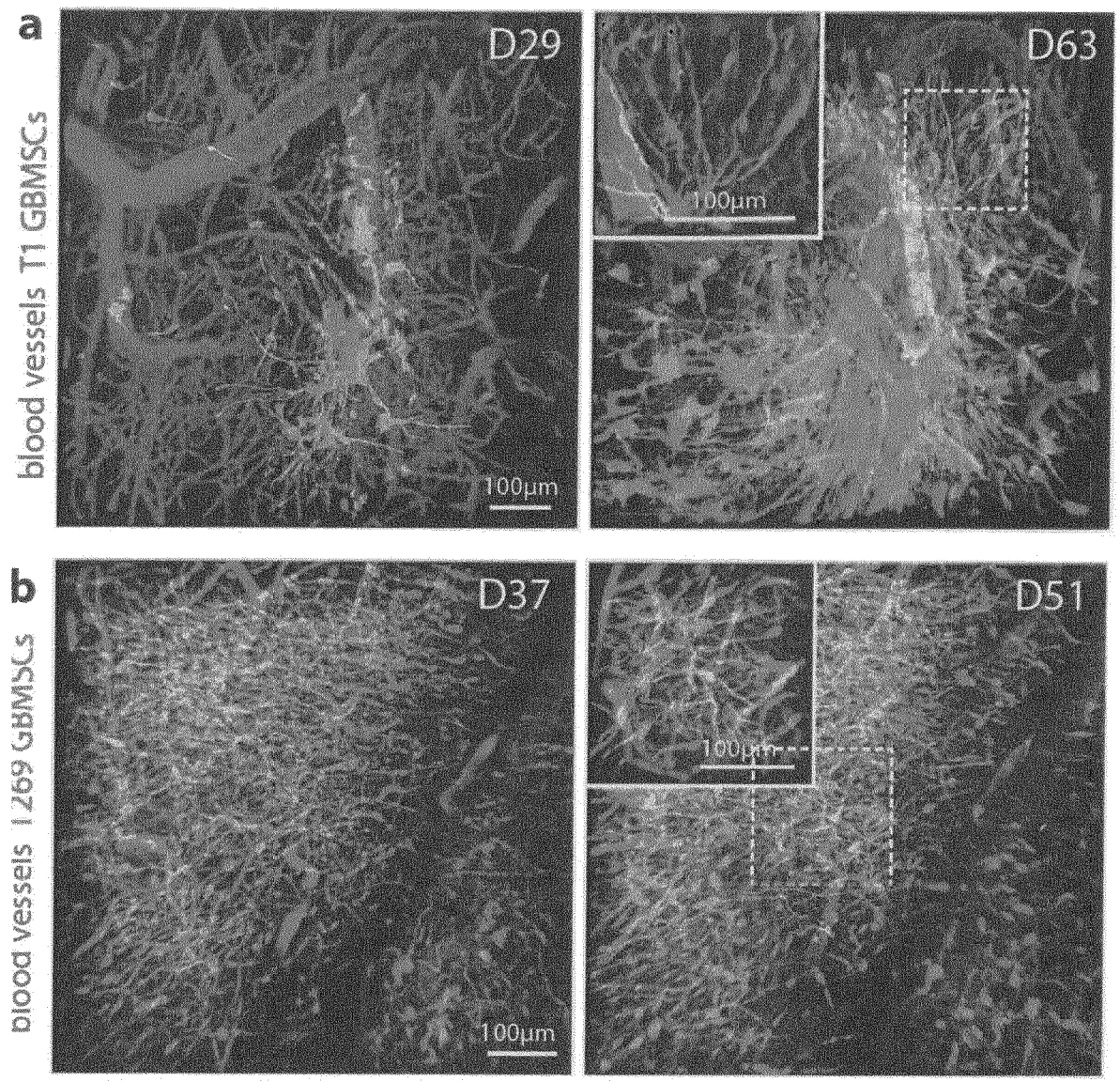
Figure 2 a, b

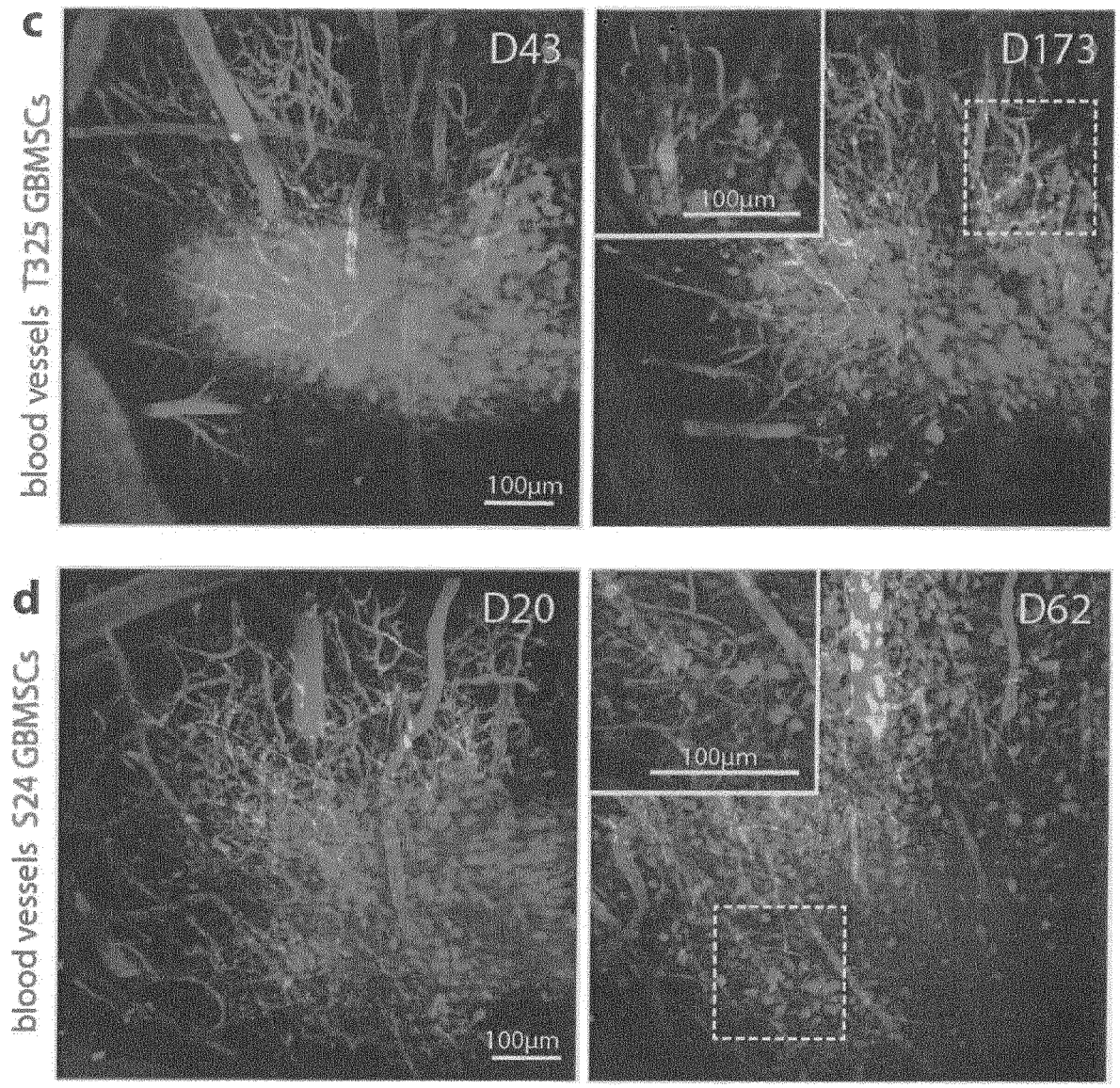
Figure 2 c, d

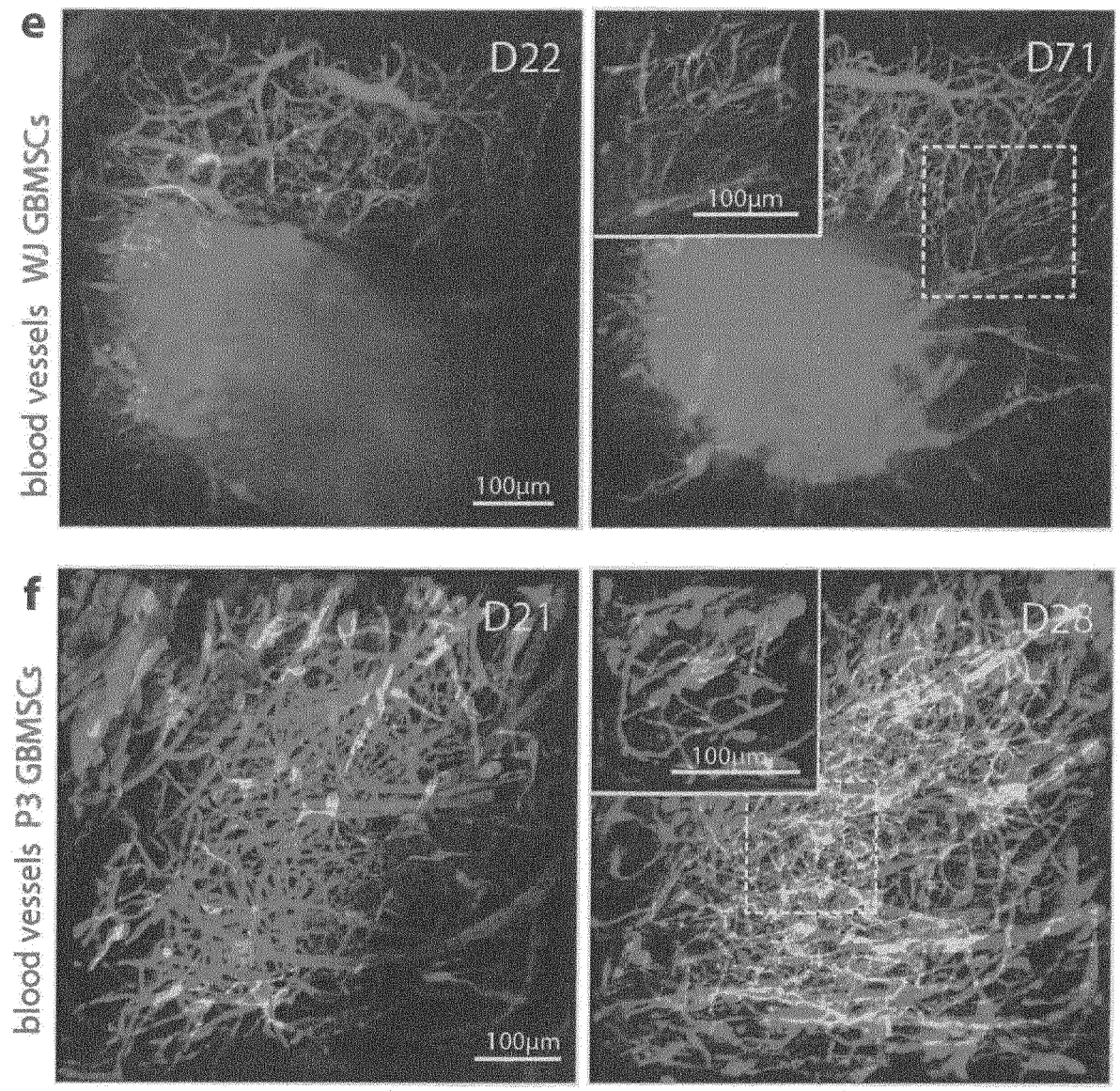
Figure 2 e, f

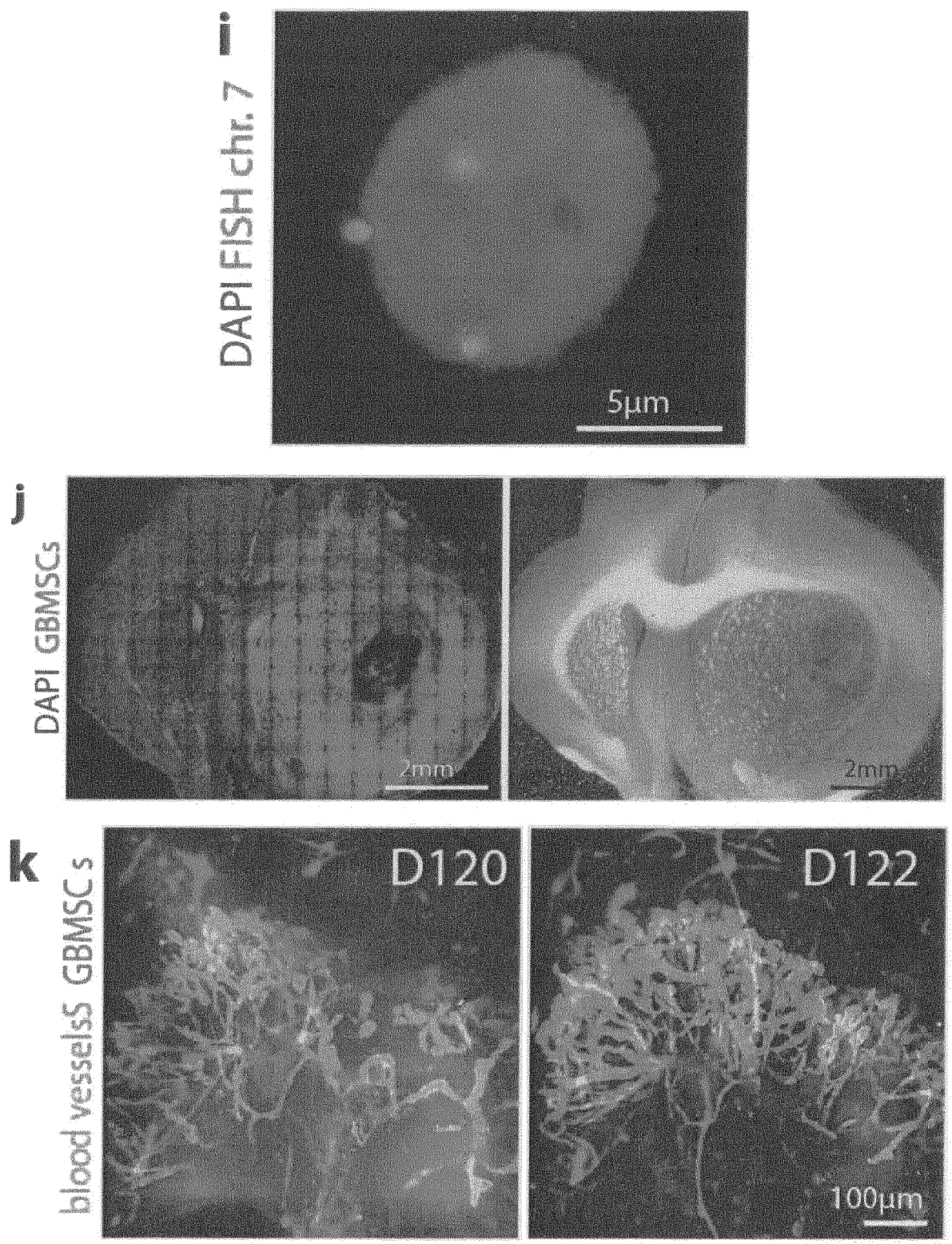
Figure 2 i, j, k

Figure 3:
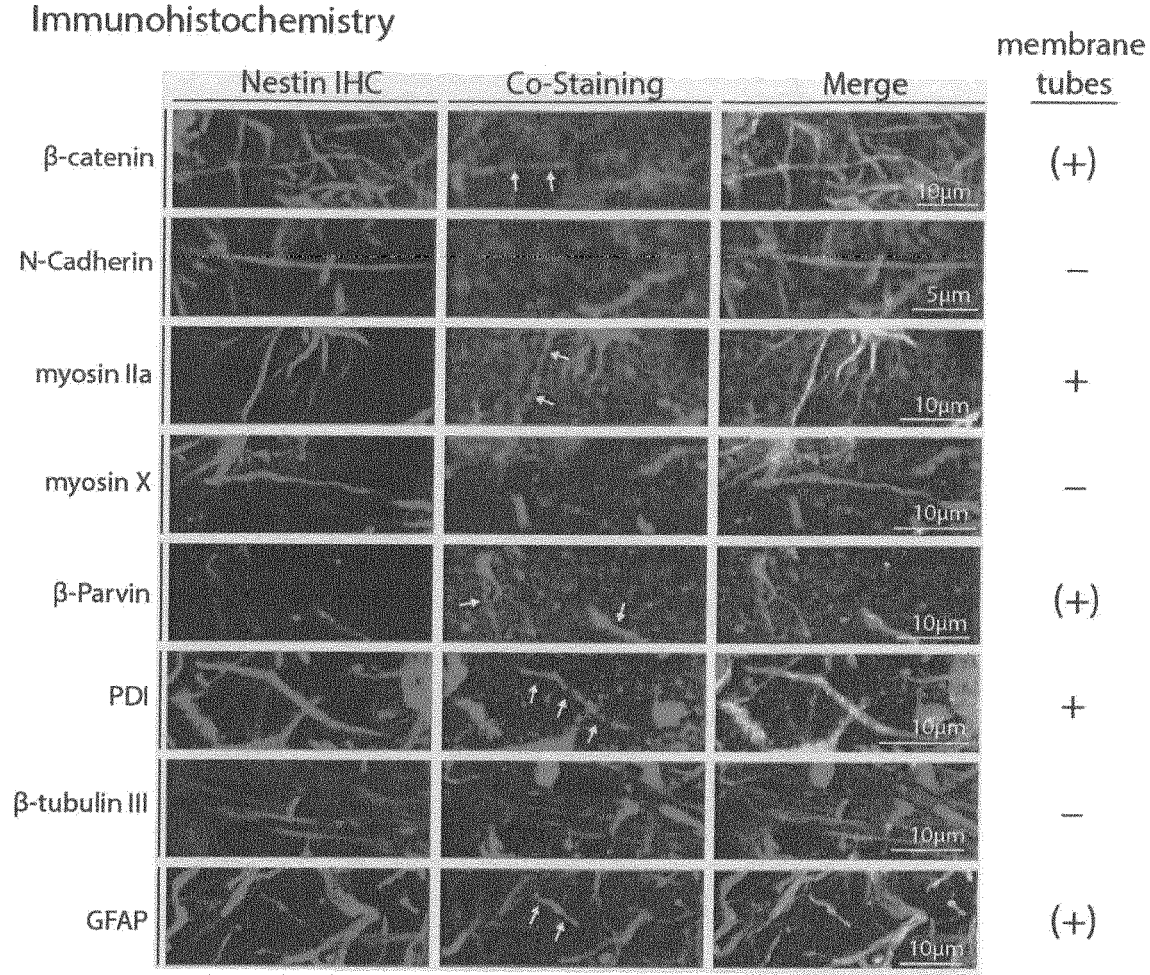

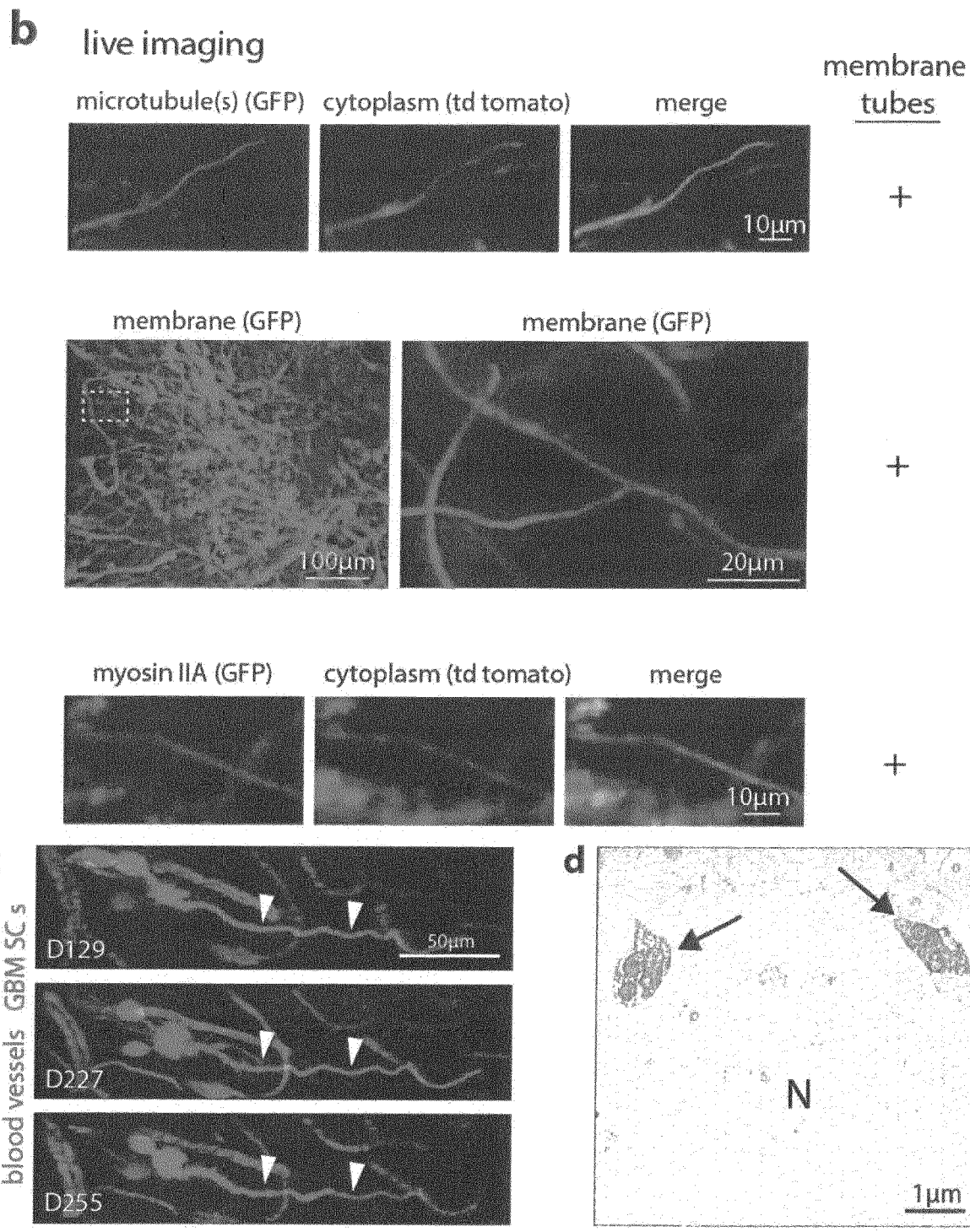
Figure 3 b, c, d

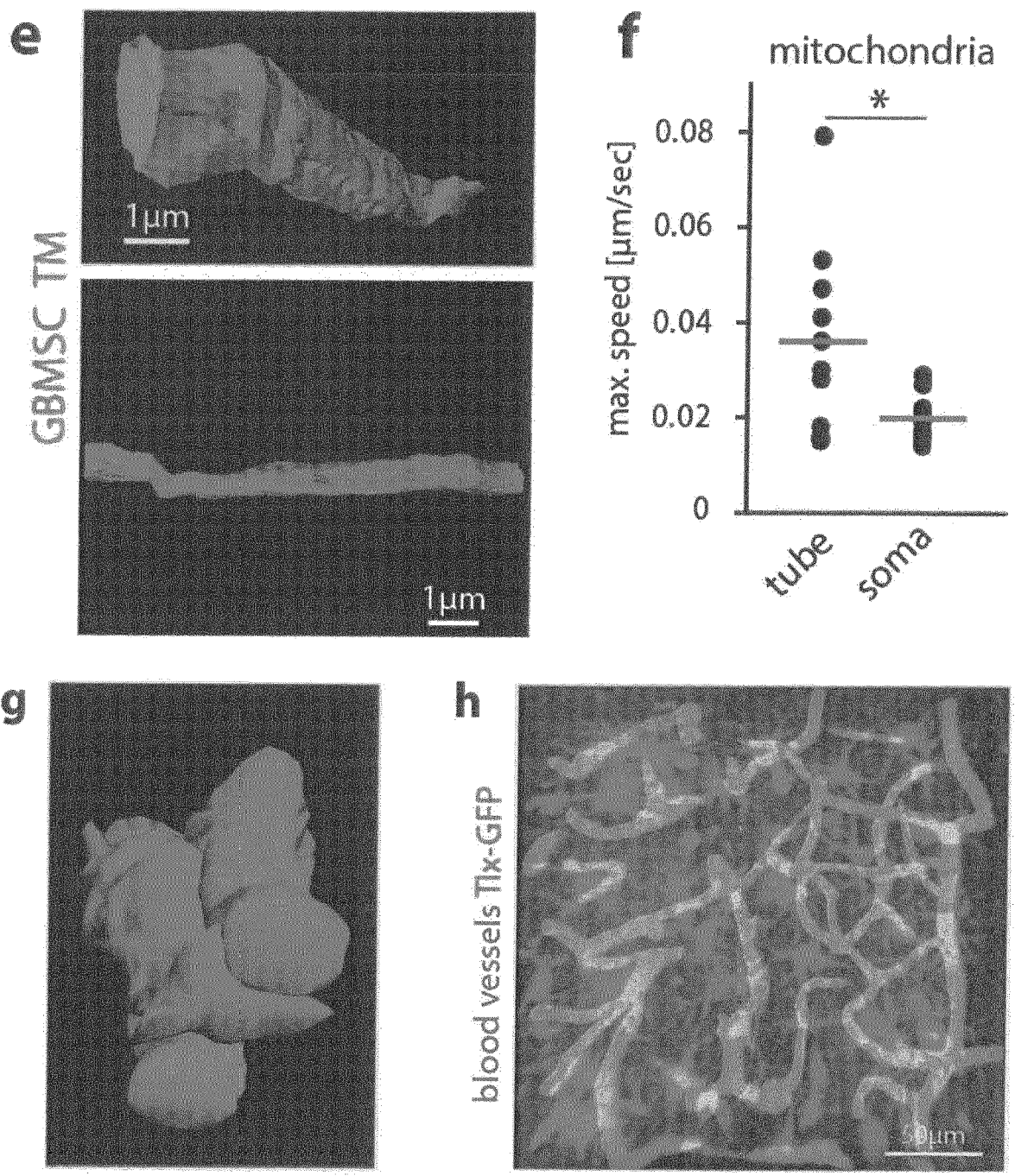
Figure 3 e, f, g, h

Figure 4:
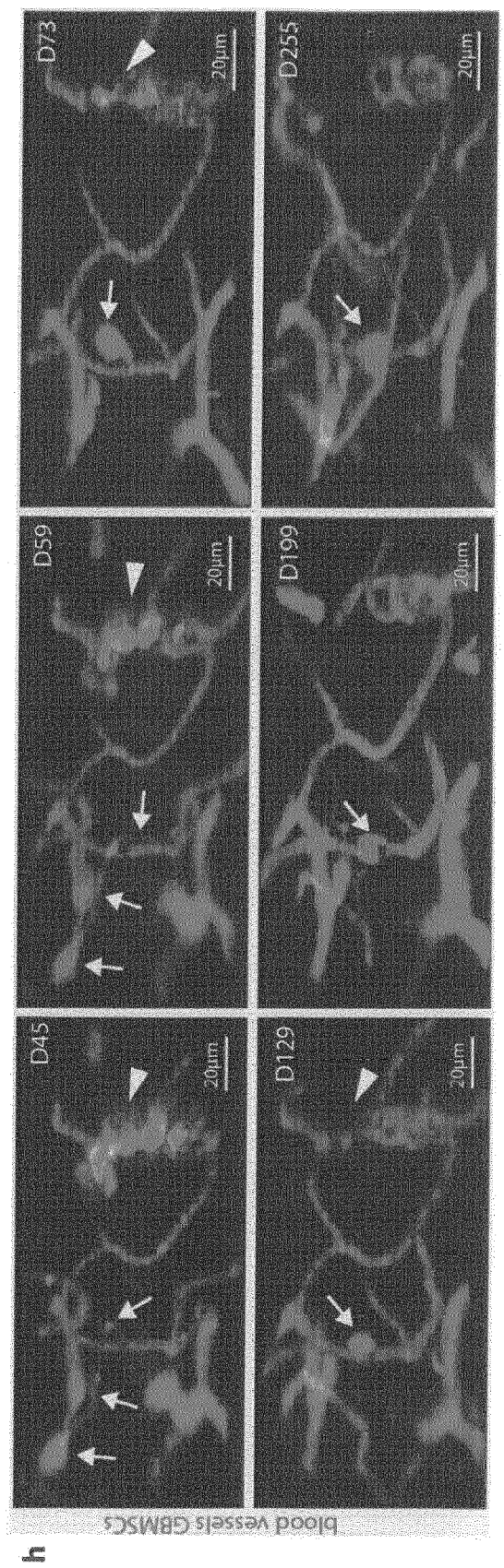
Figure 4:
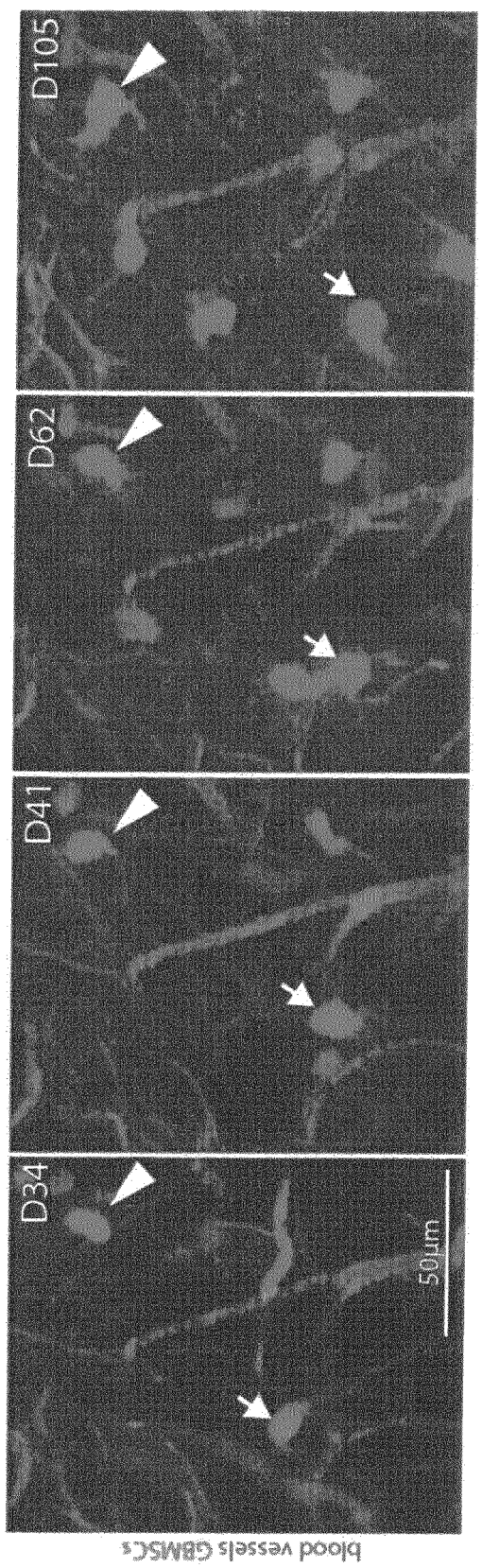

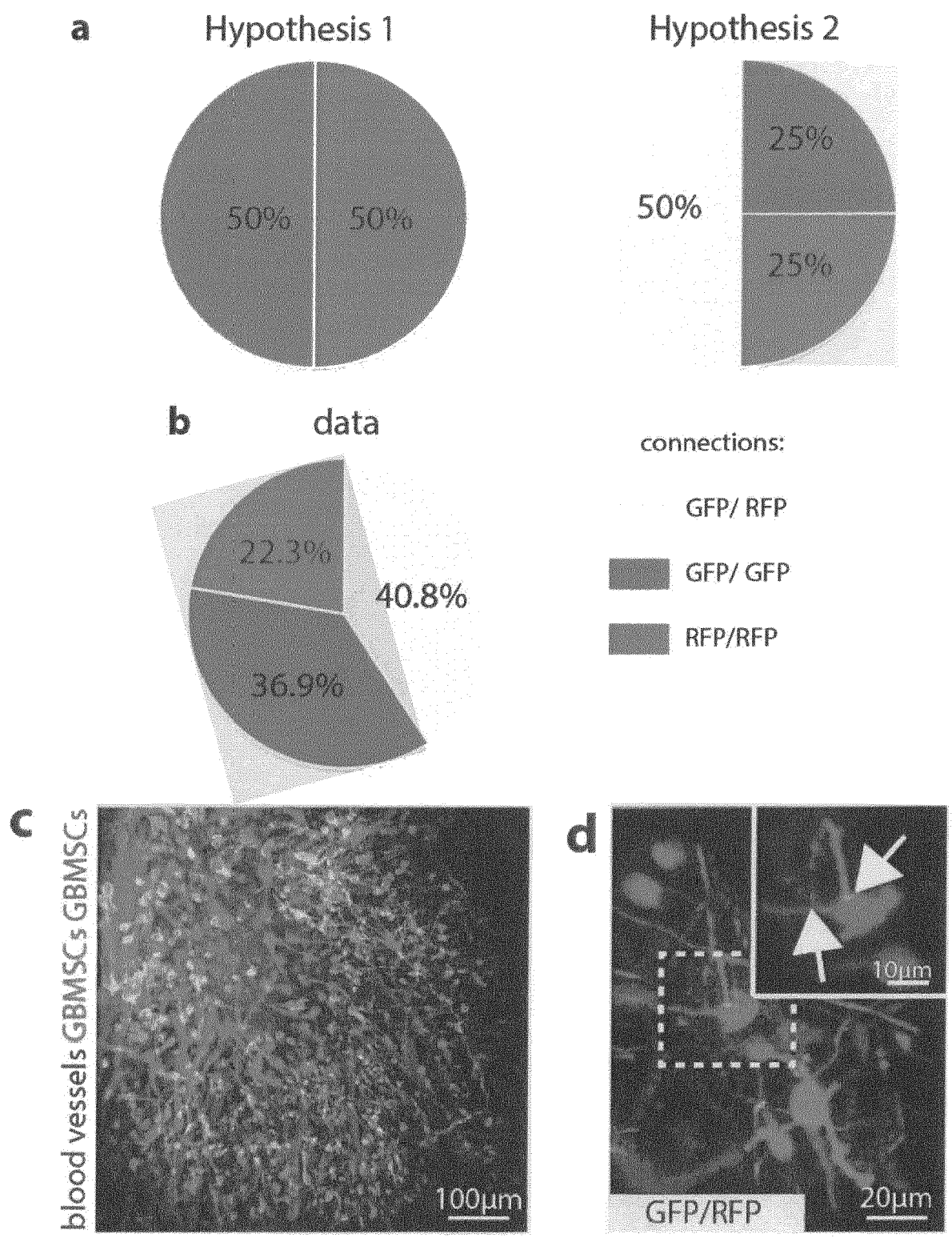
Figure 4 a, b, c, d

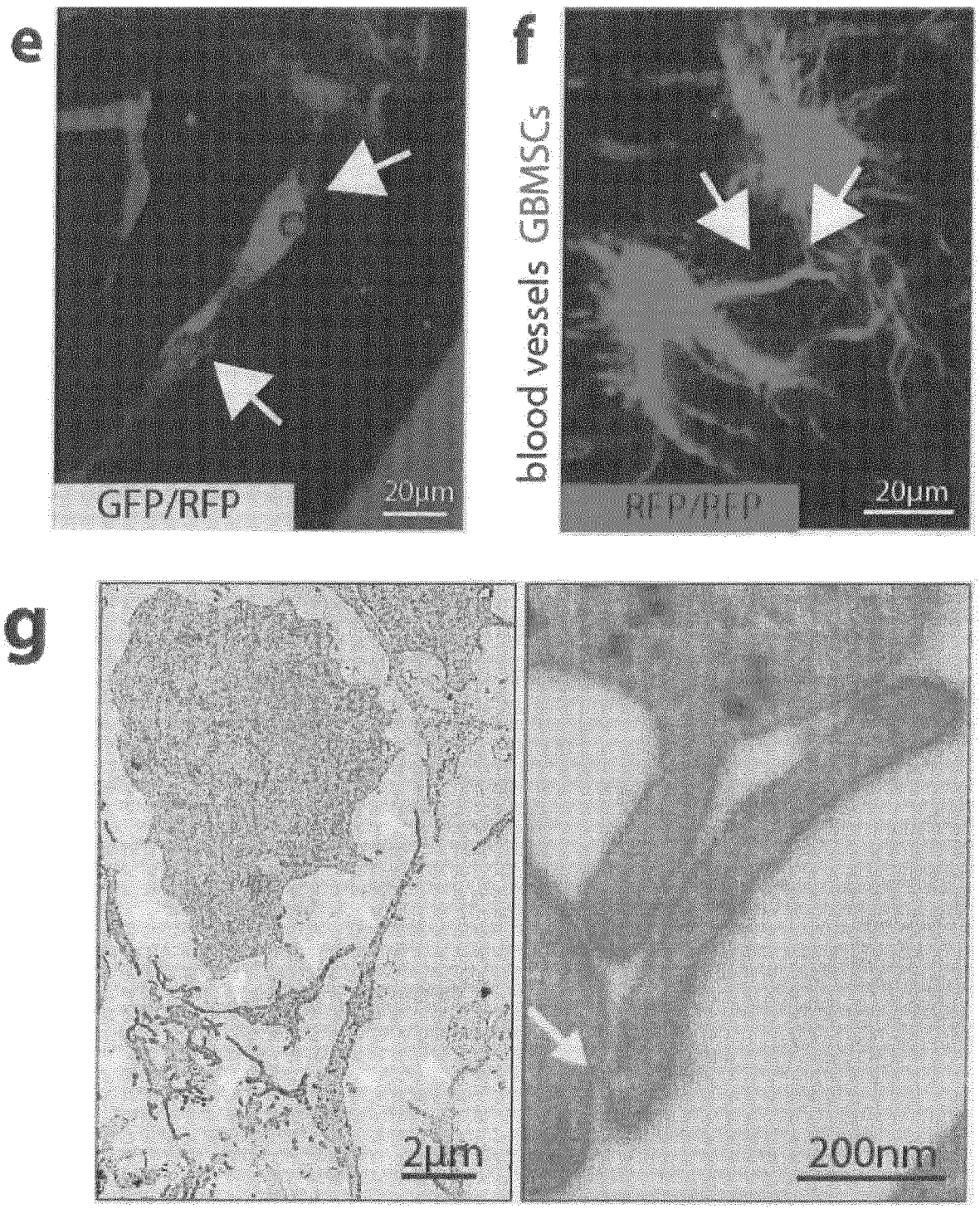
Figure 4 e, f, g

Figure 7:
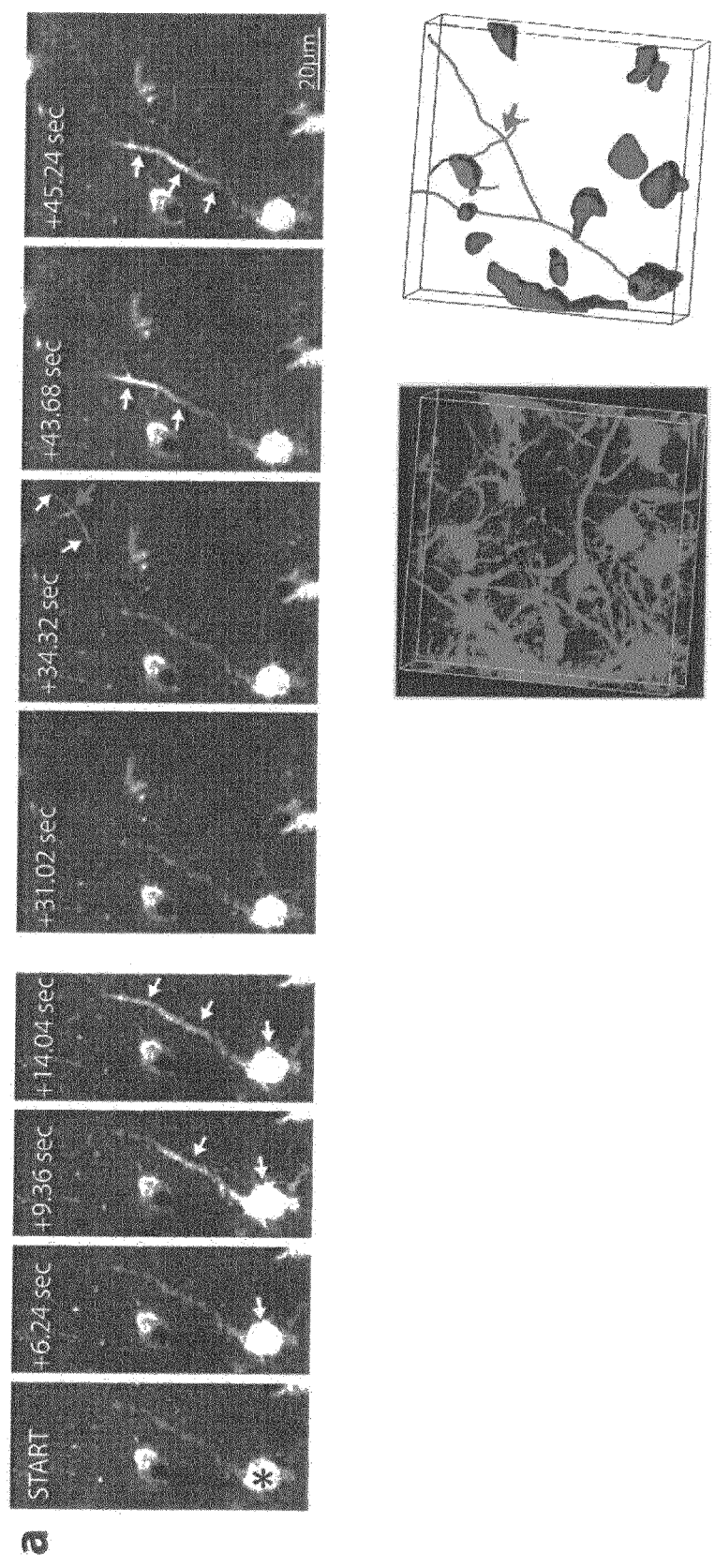

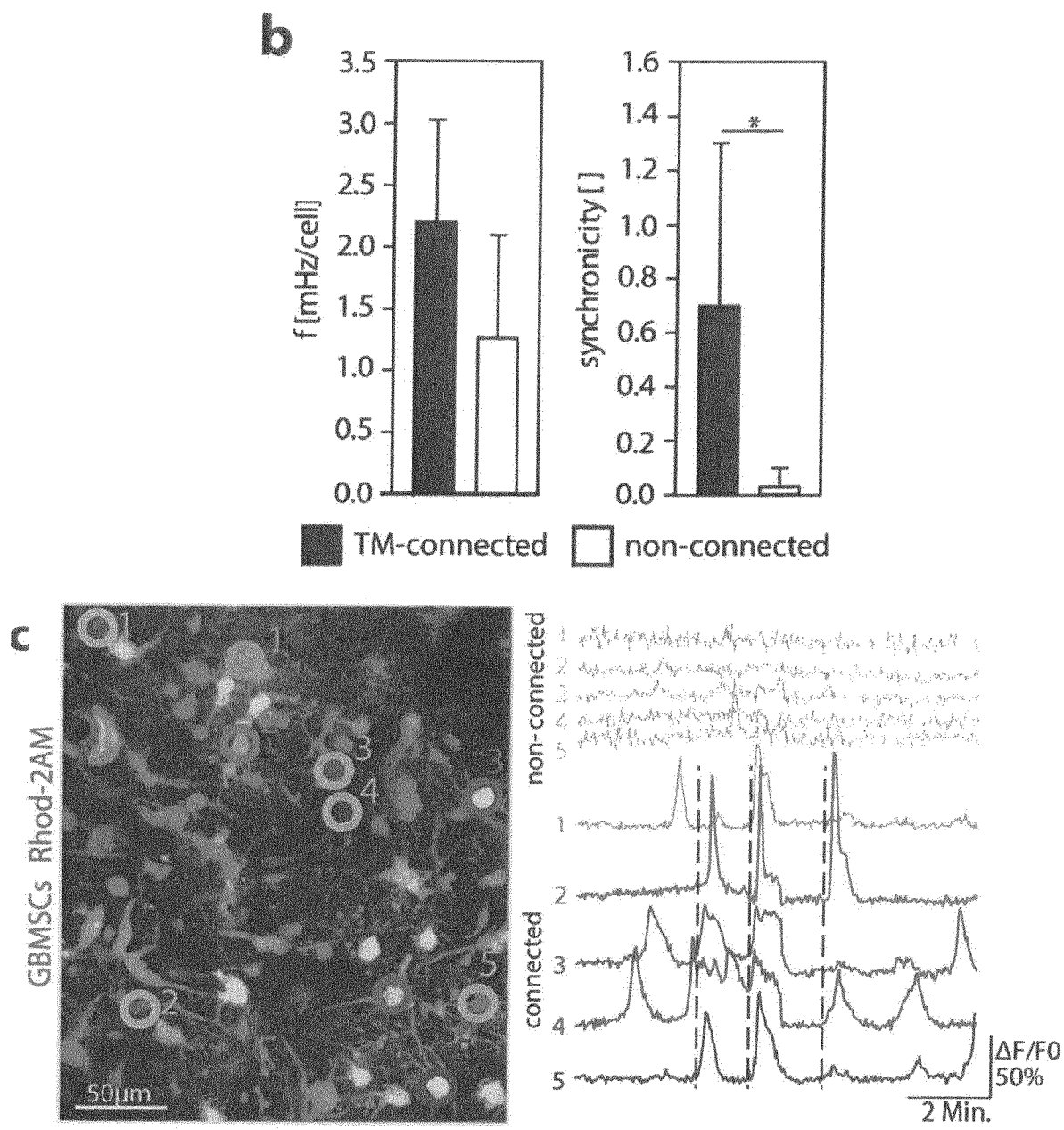
Figure 7 b, c

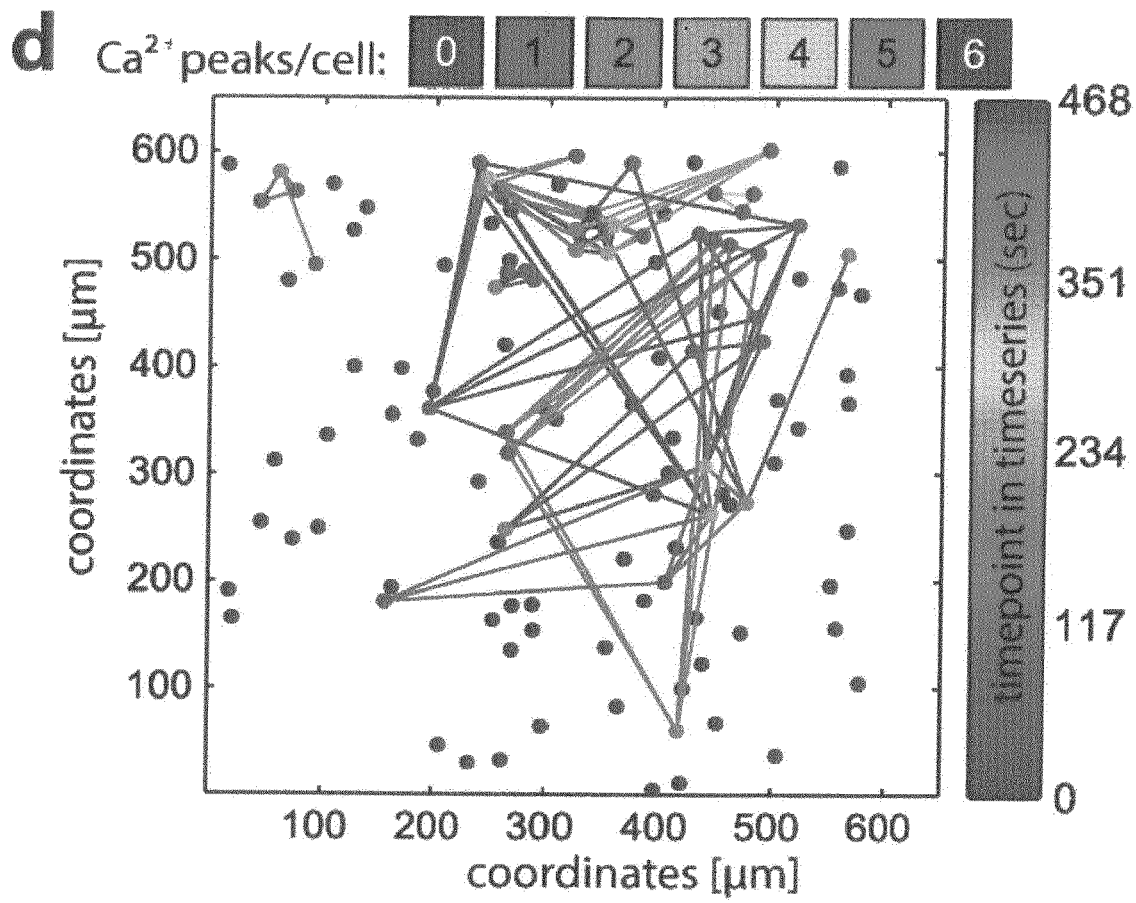
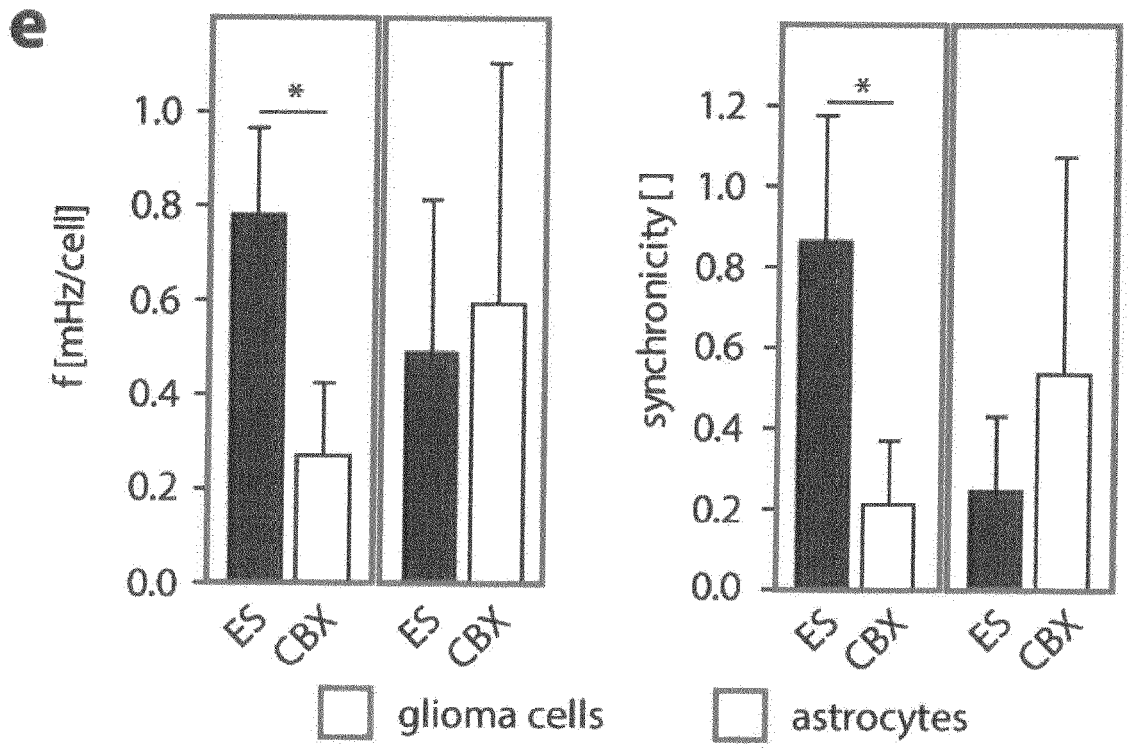
Figure 7 d, e

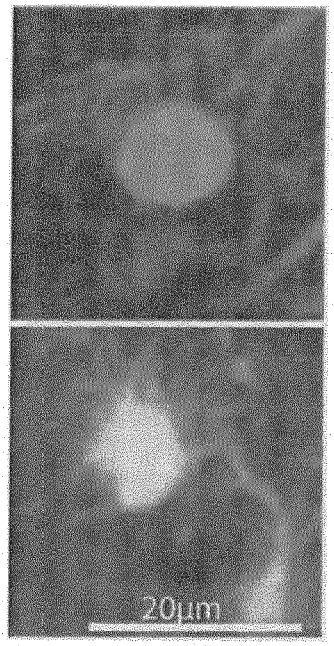
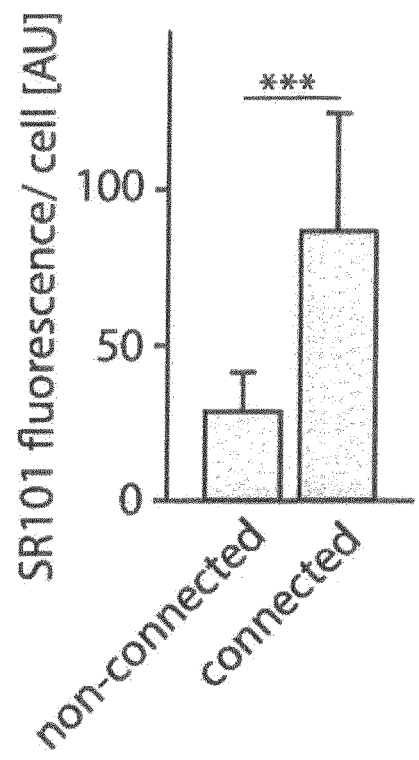
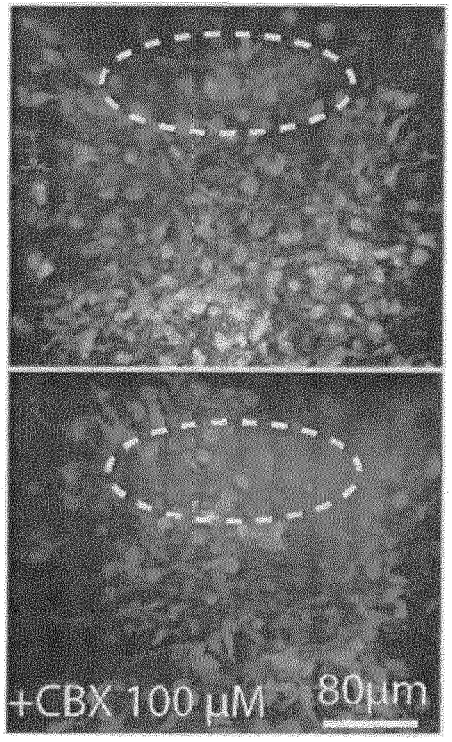
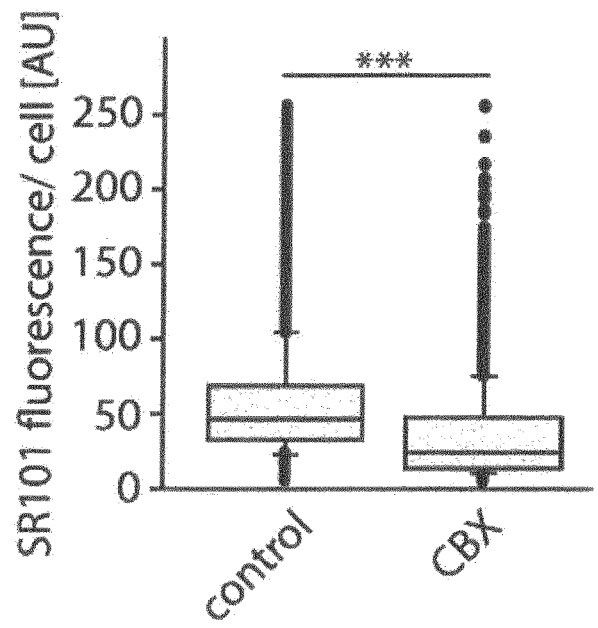
Figure 7 f, g

Figure 8:
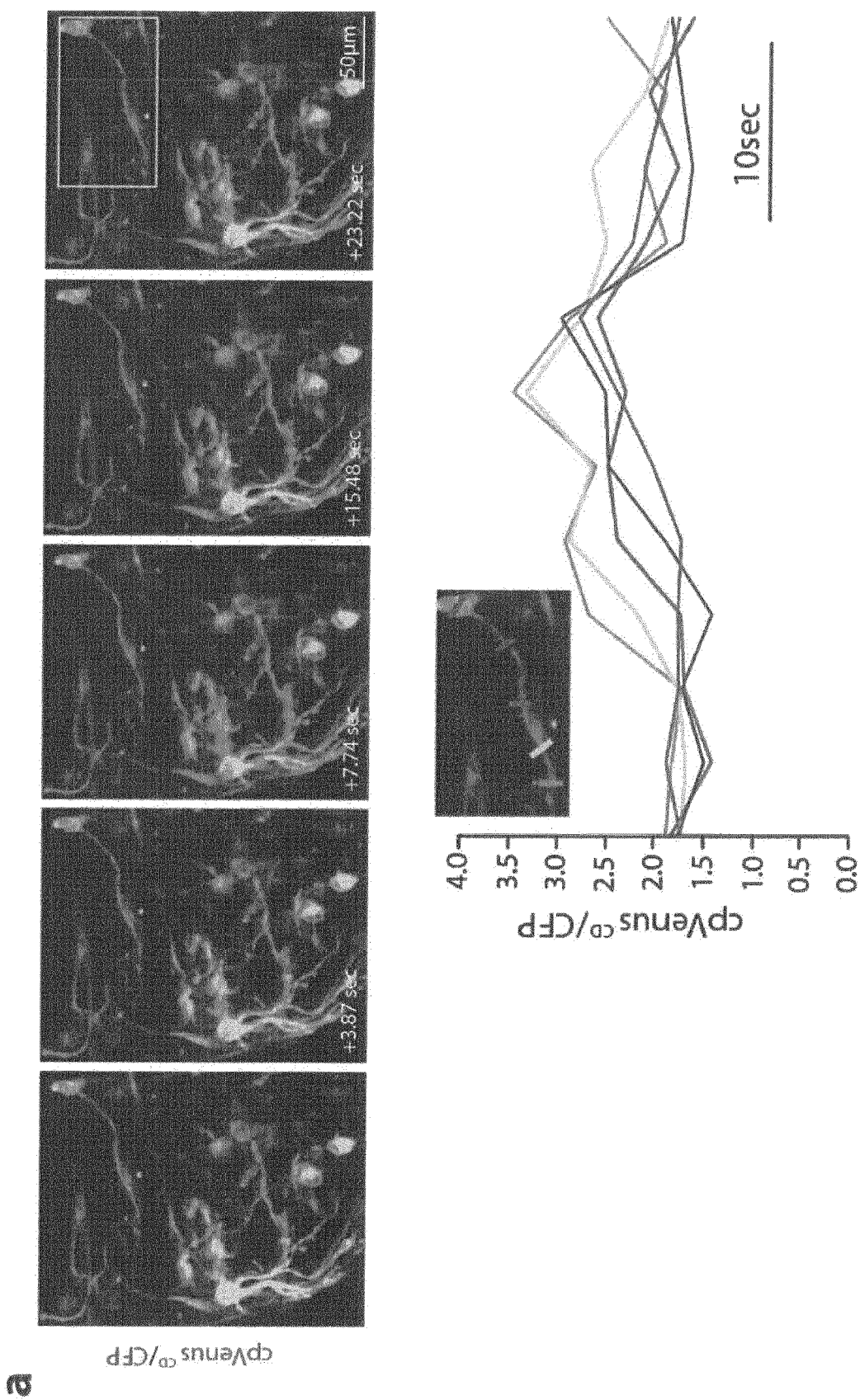
Figure 8:
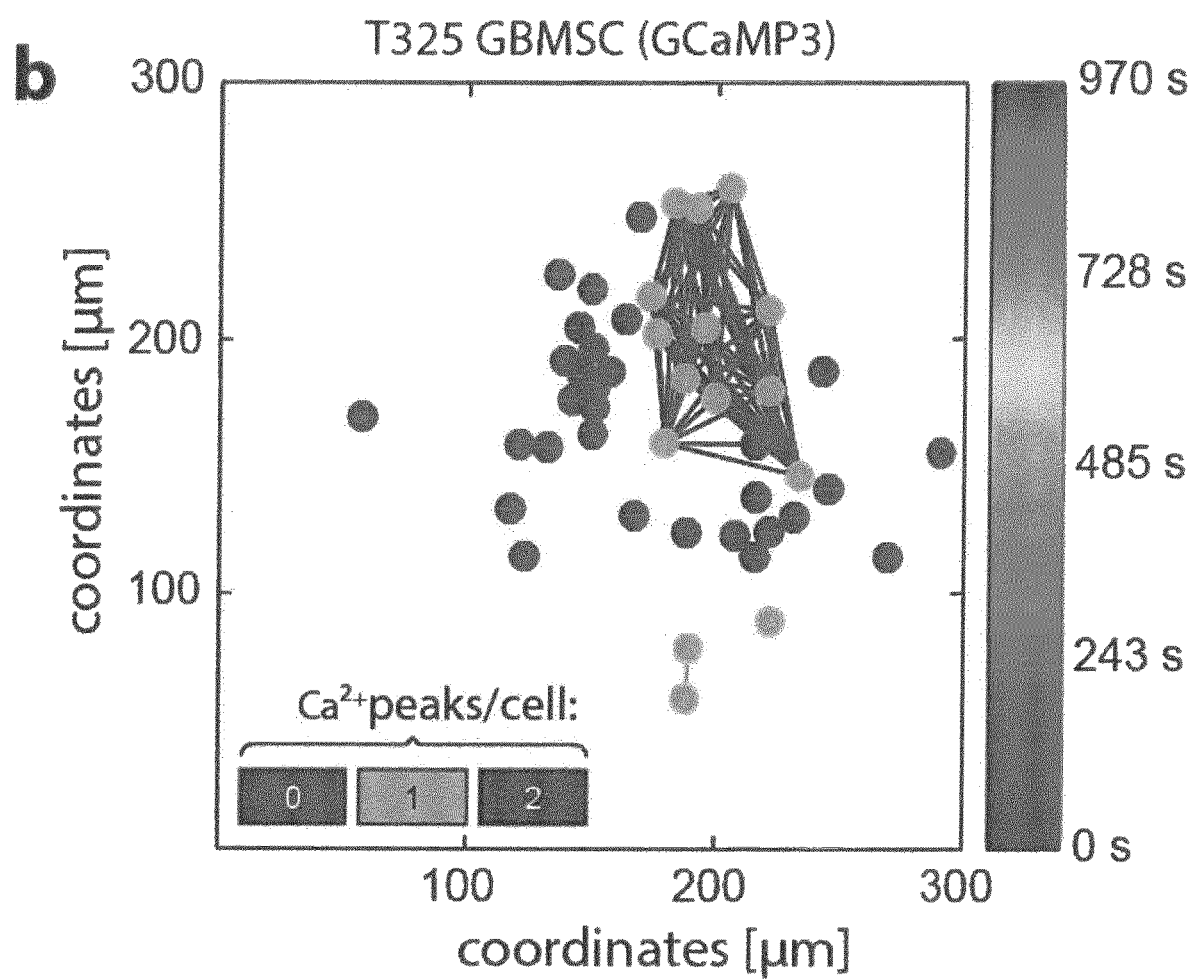
Figure 8:
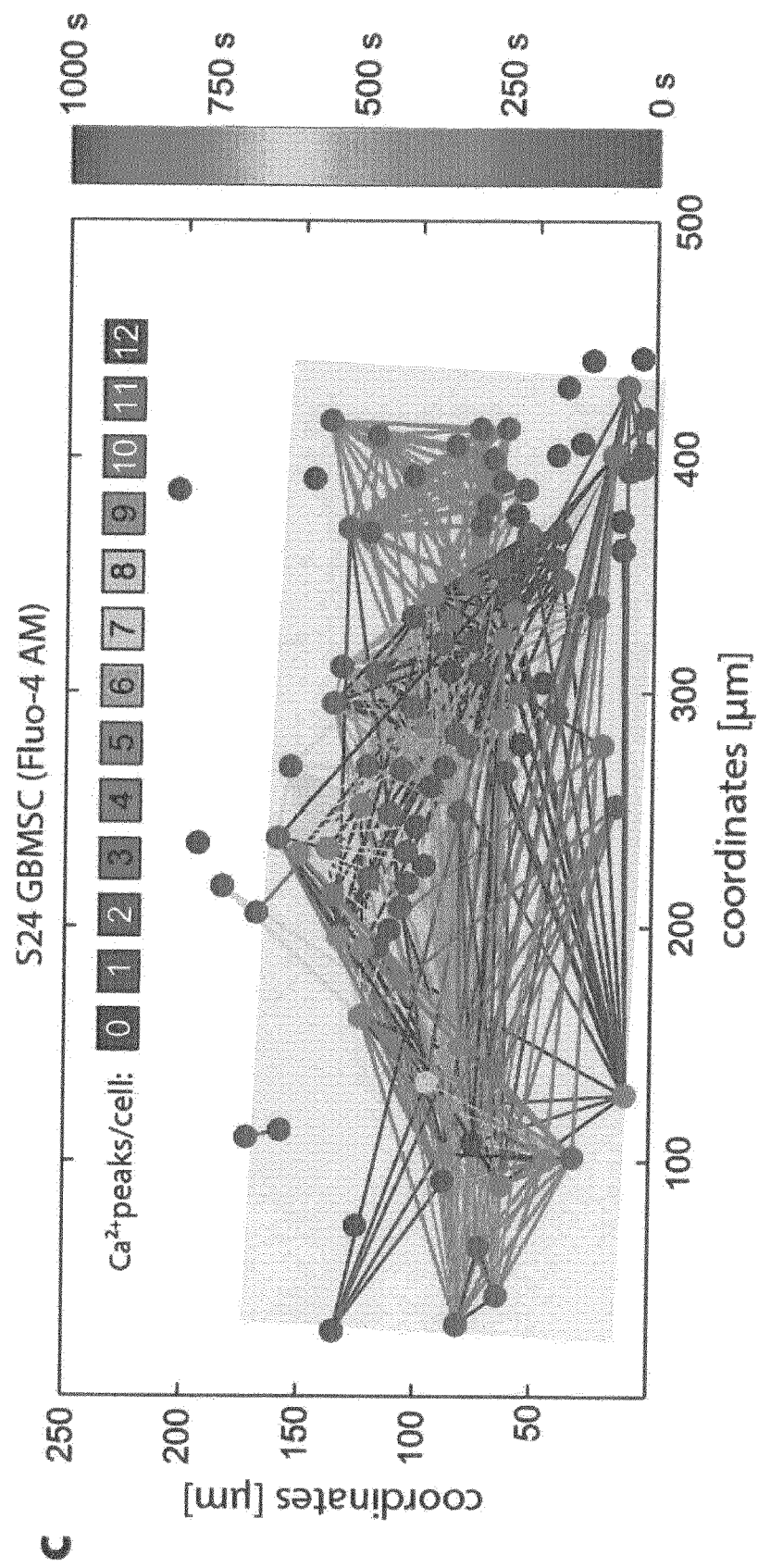

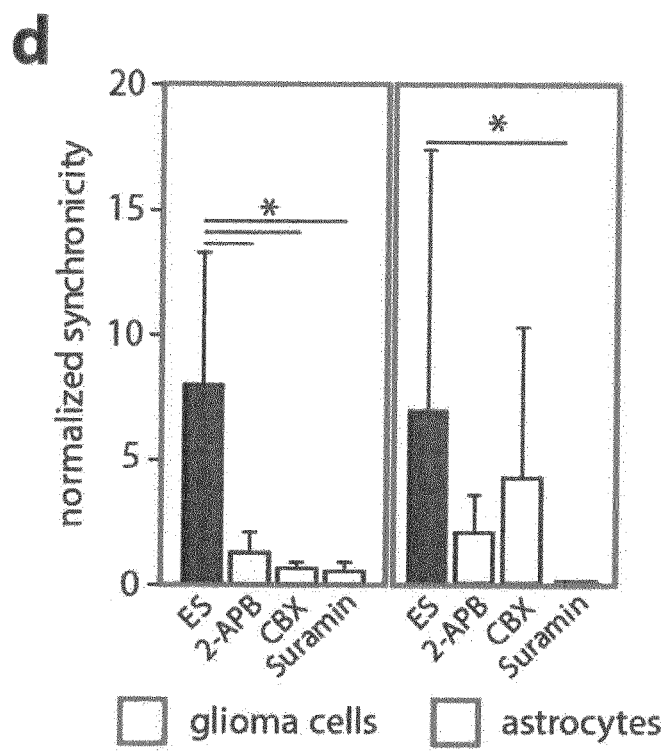
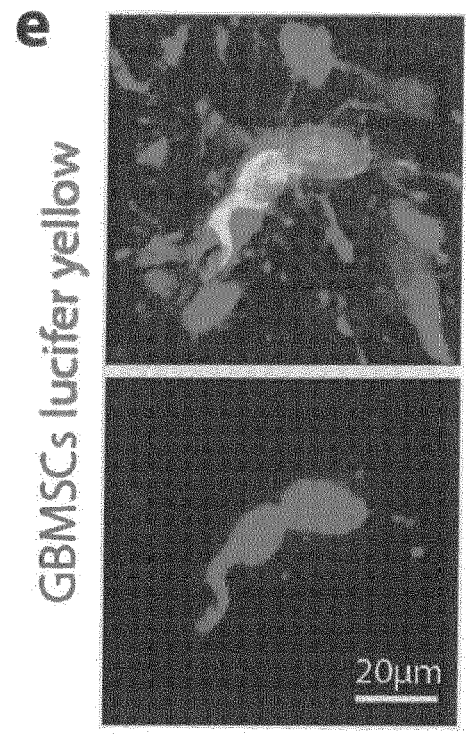
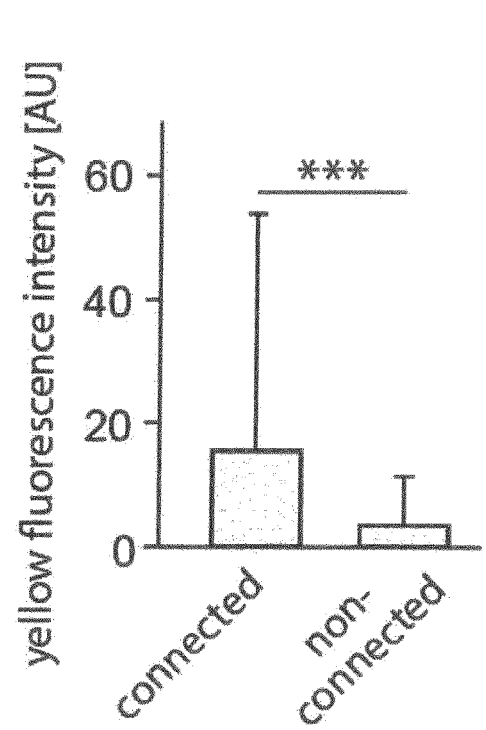
Figure 8 d, e, f, g

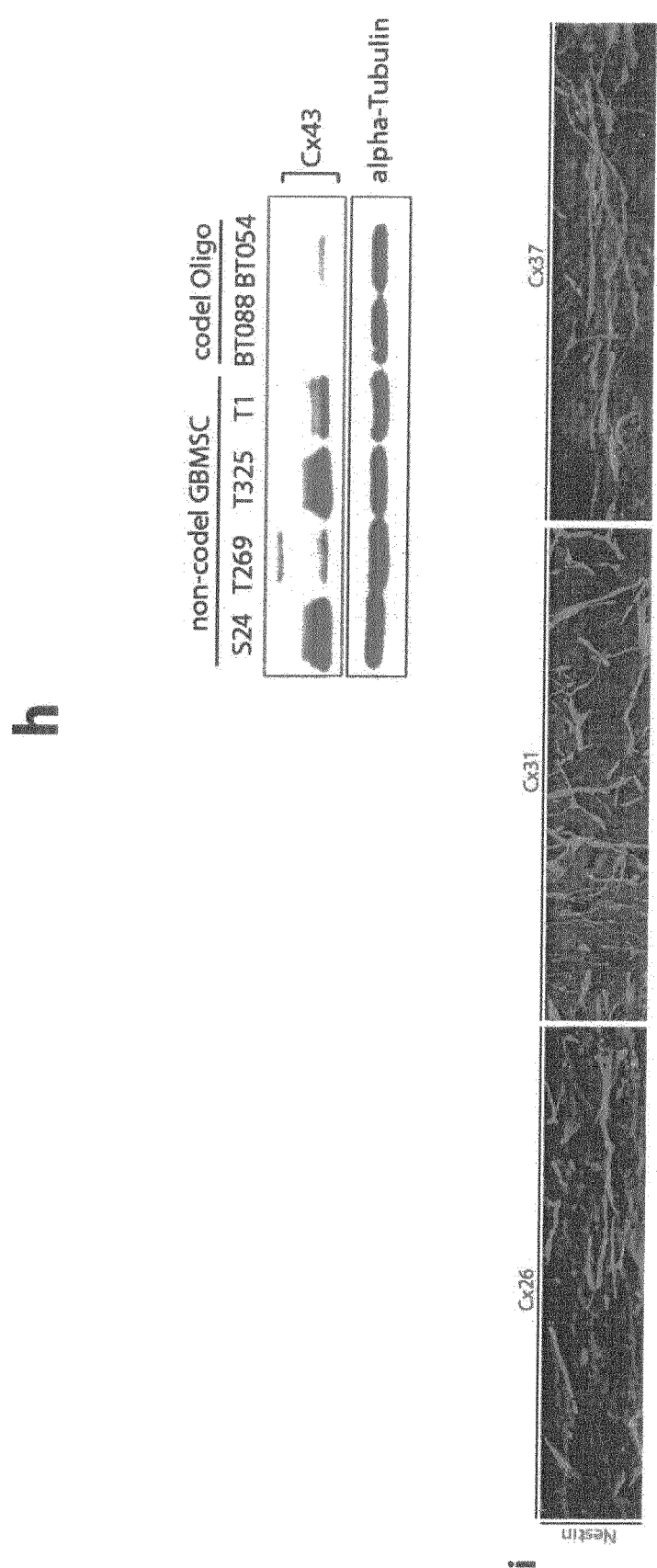
Figure 8 h, i

Figure 10:
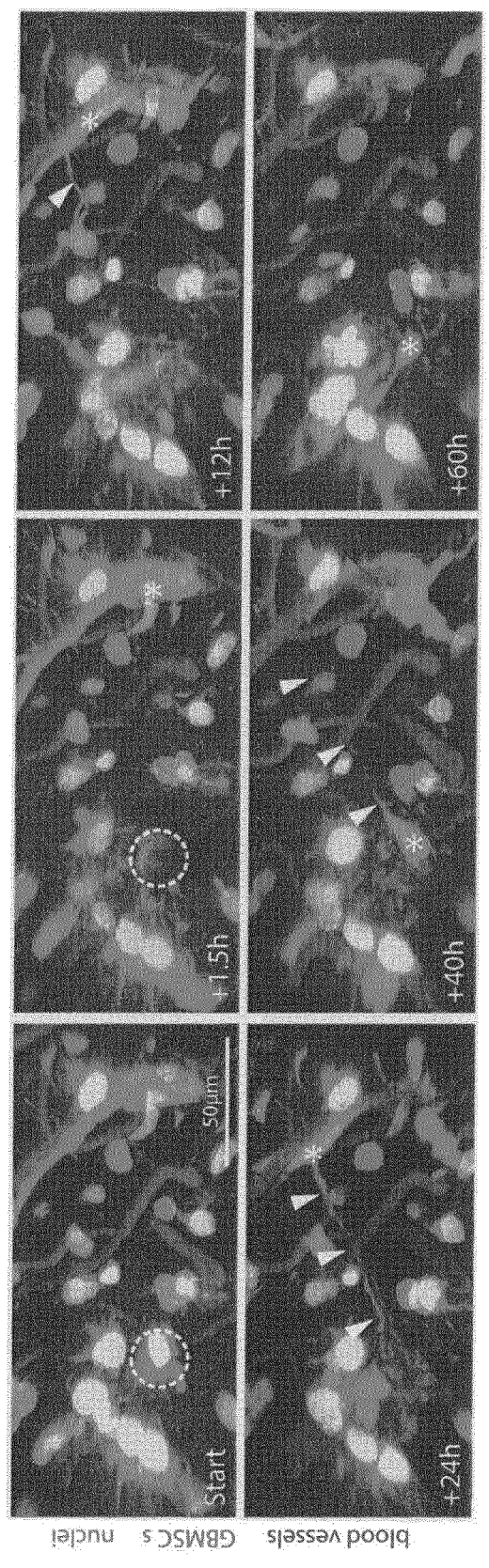
Figure 10:
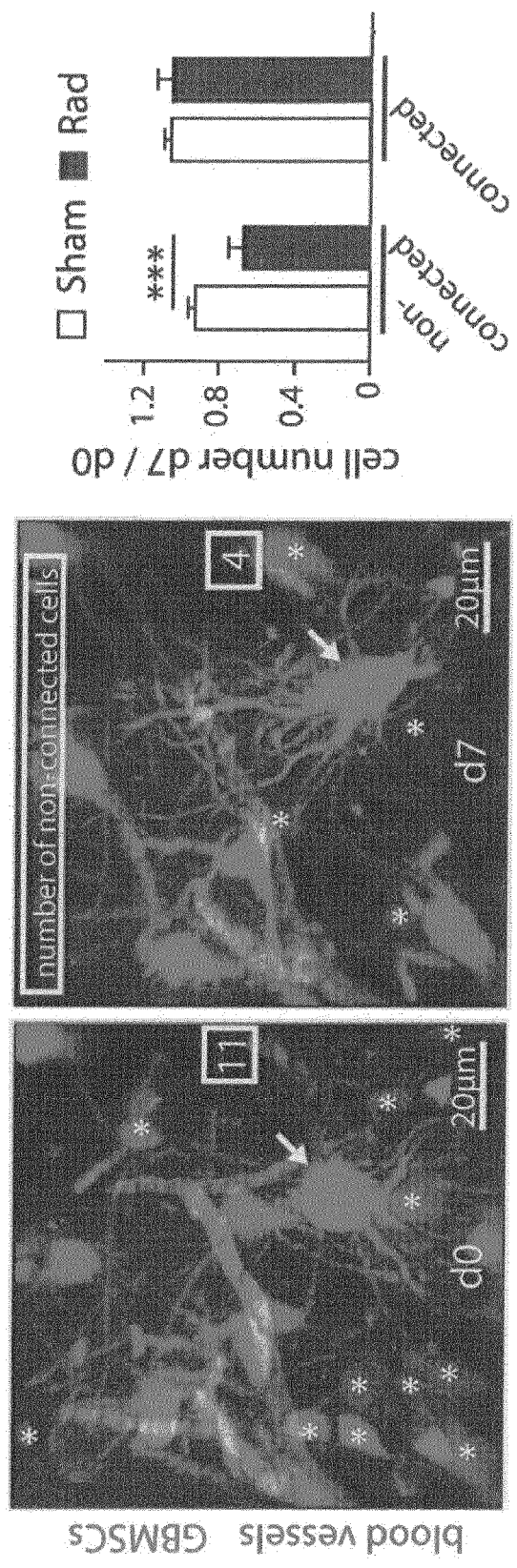

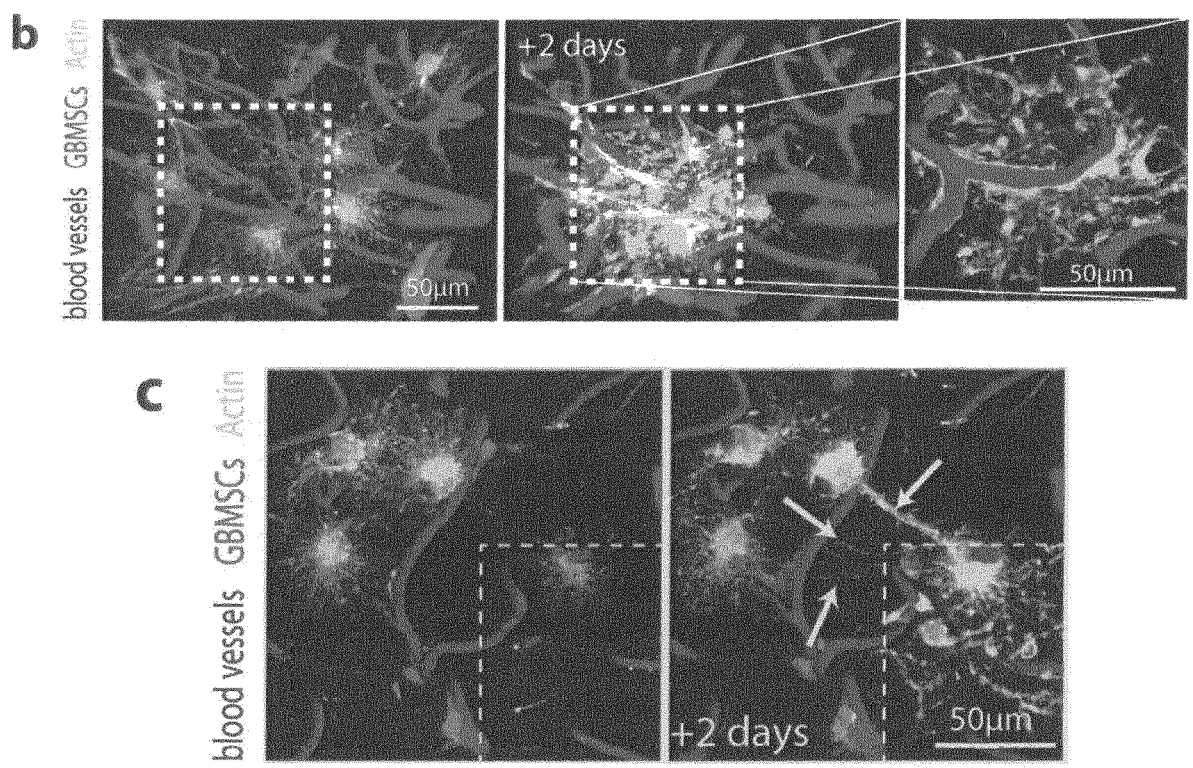
Figure 10 b, c

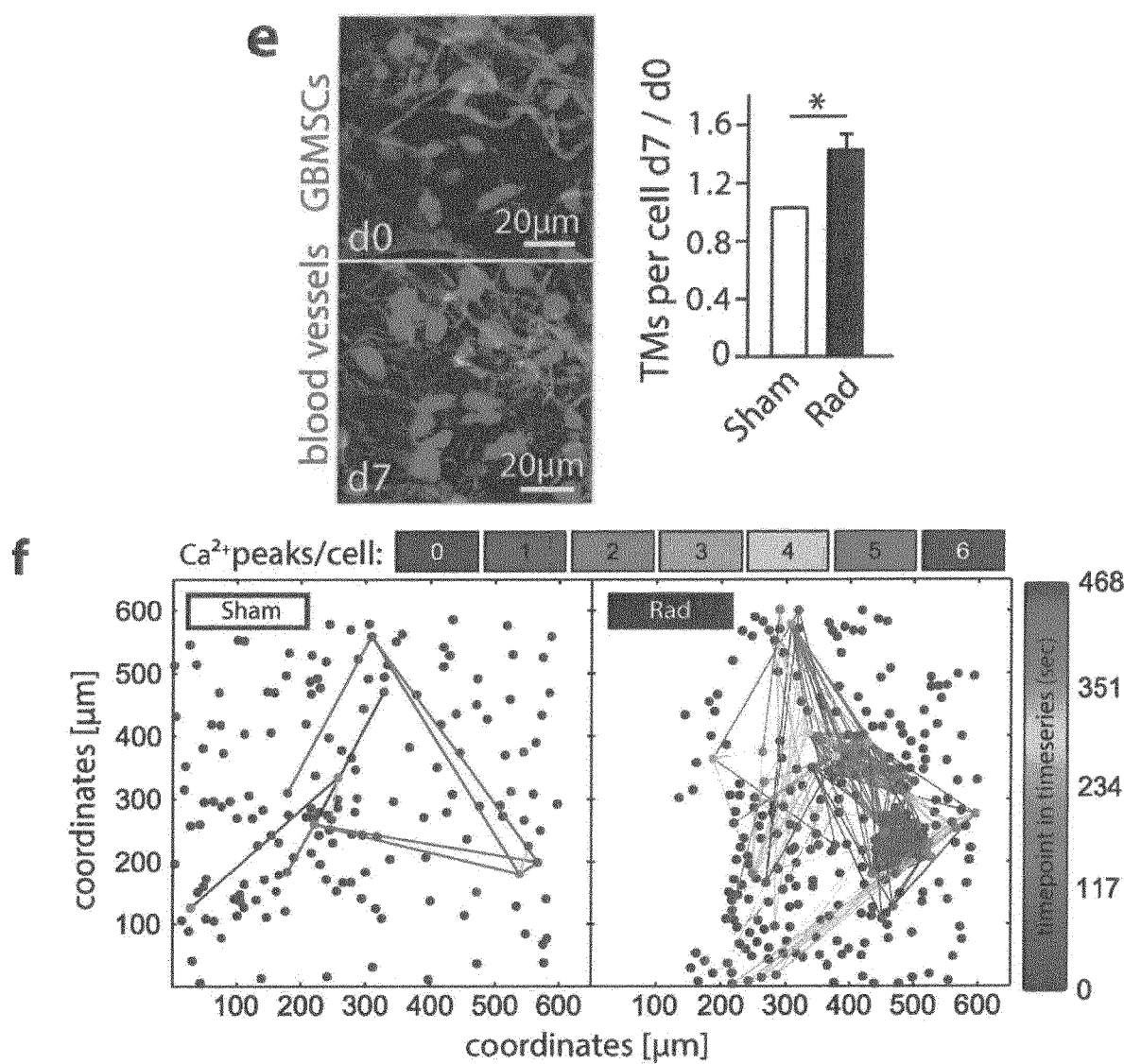
Figure 10 e, f

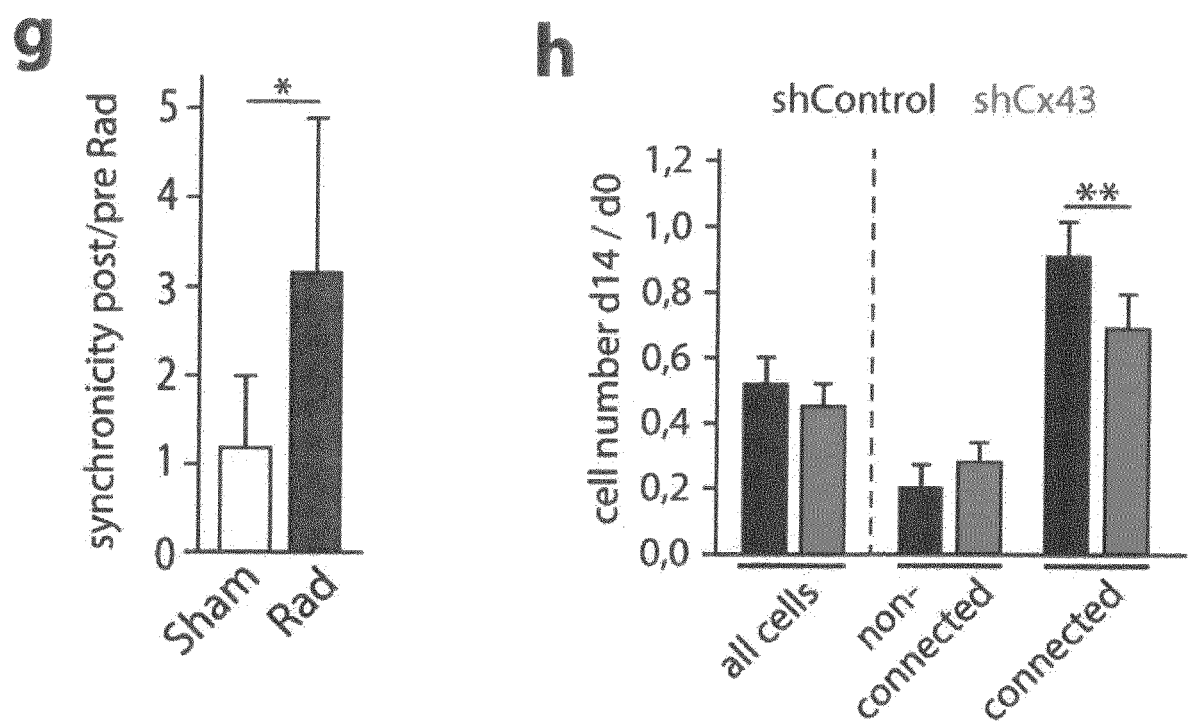
Figure 10 g, h

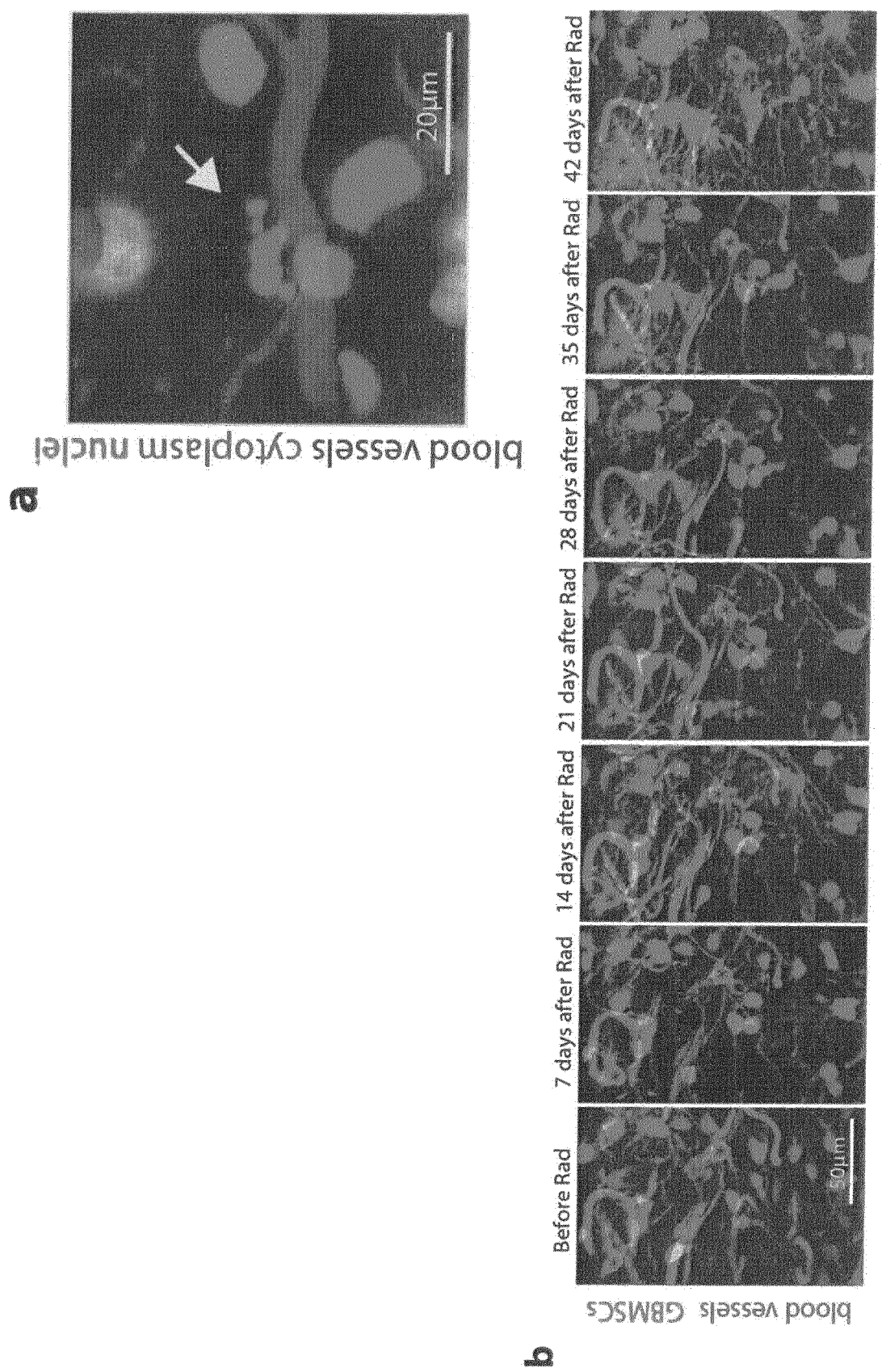
Figure 11 a, b

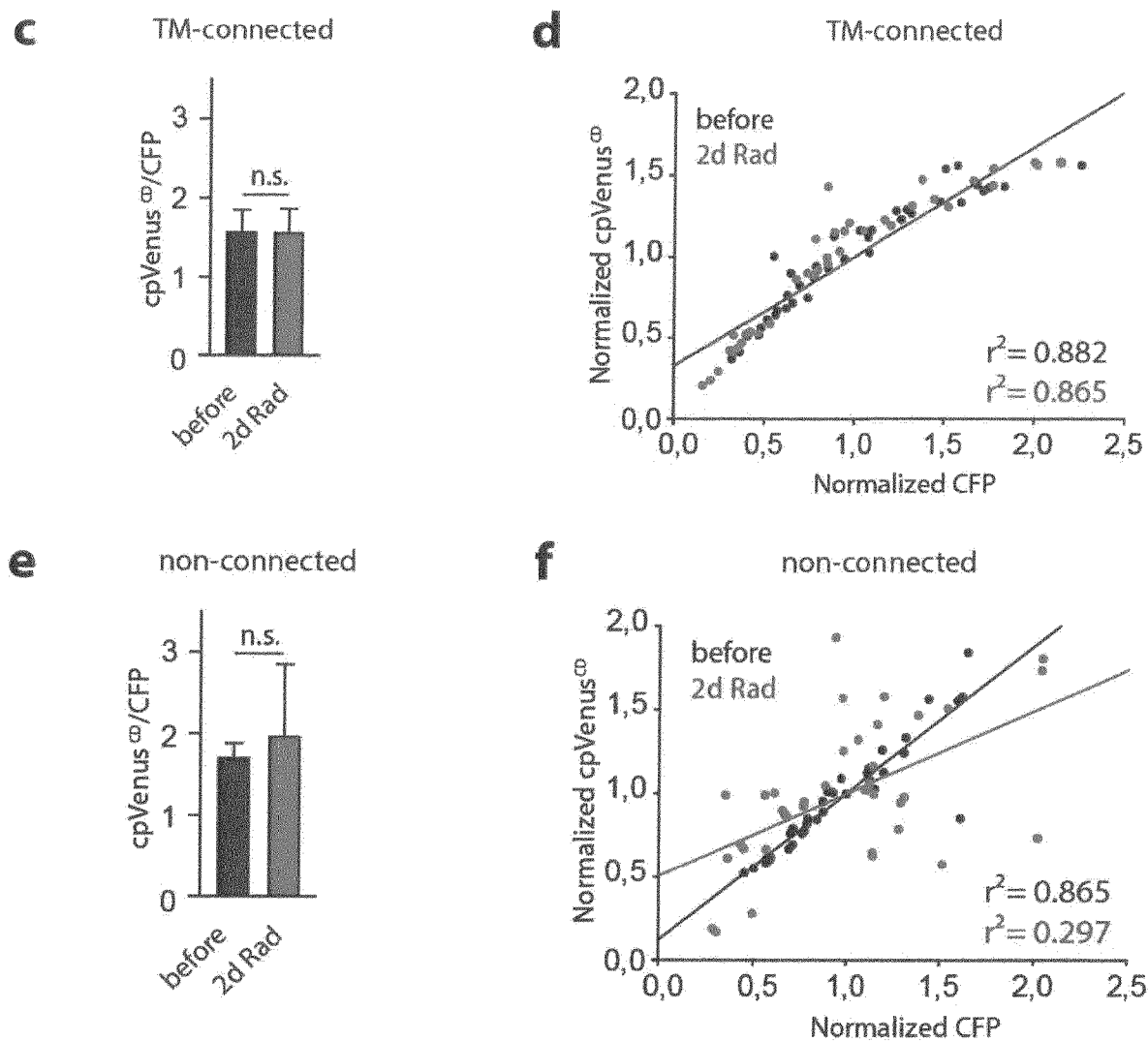
Figure 11 c, d, e, f

Figure 12 c

Figure 13:
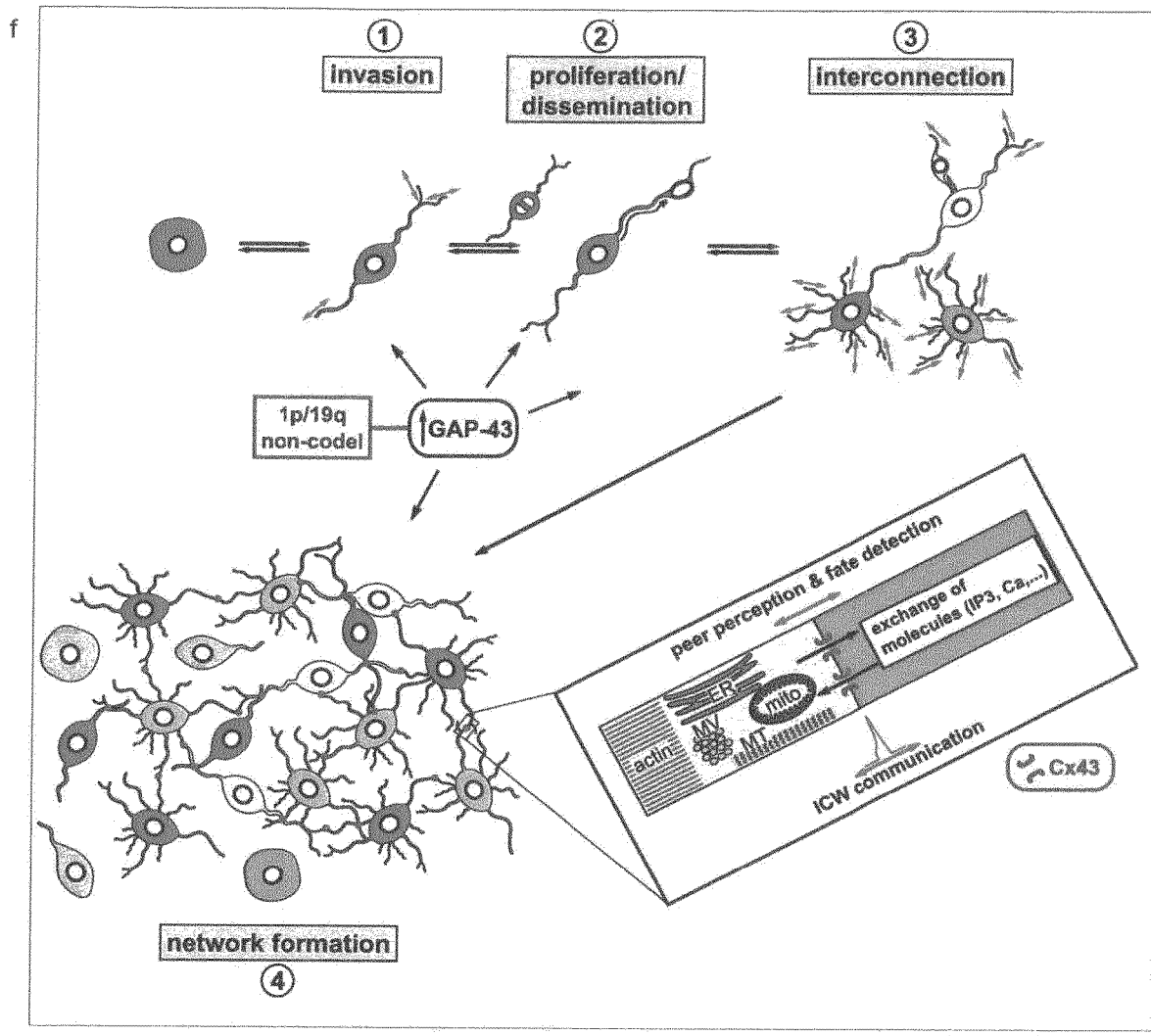

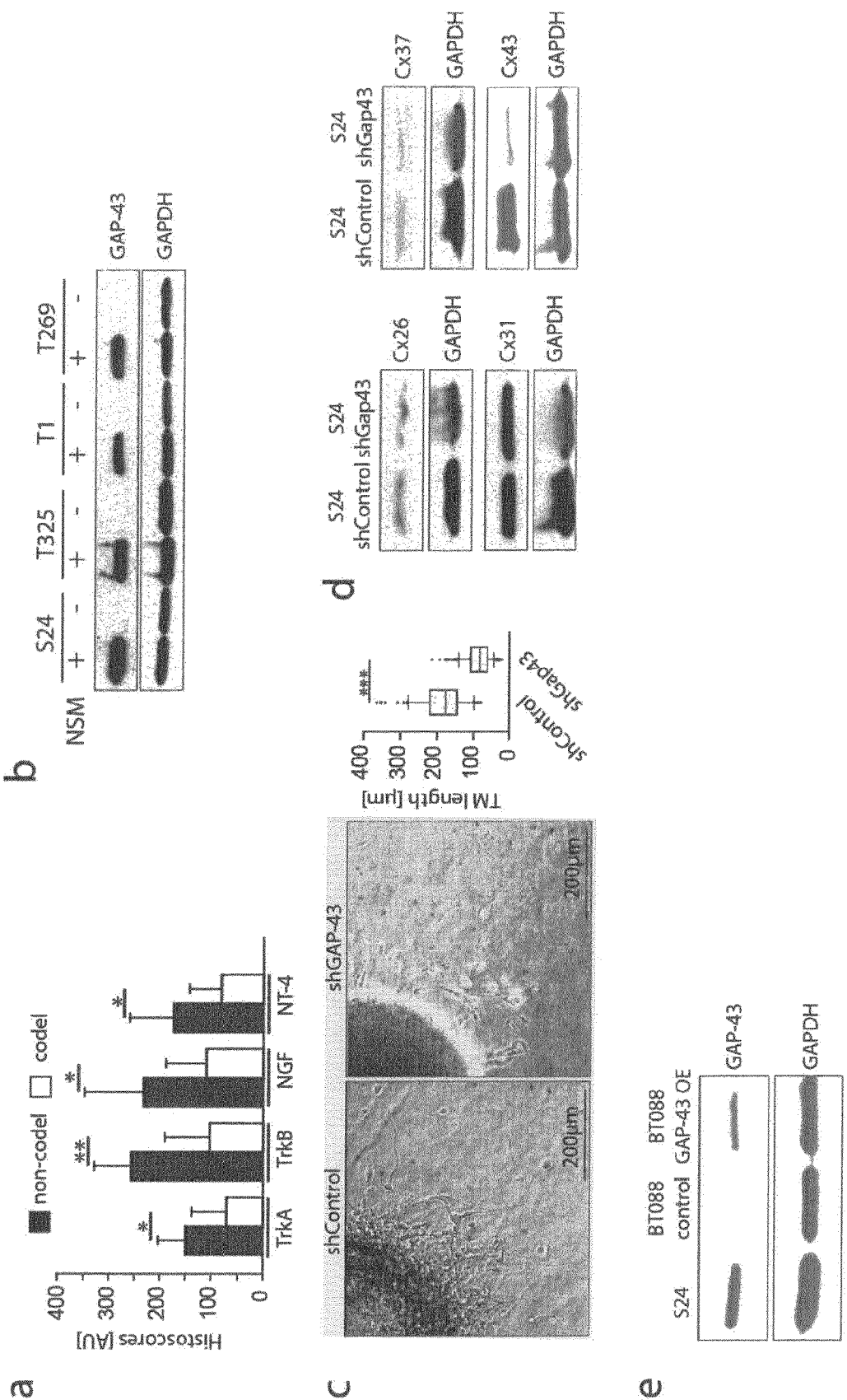
Figure 13 a, b, c, d, e

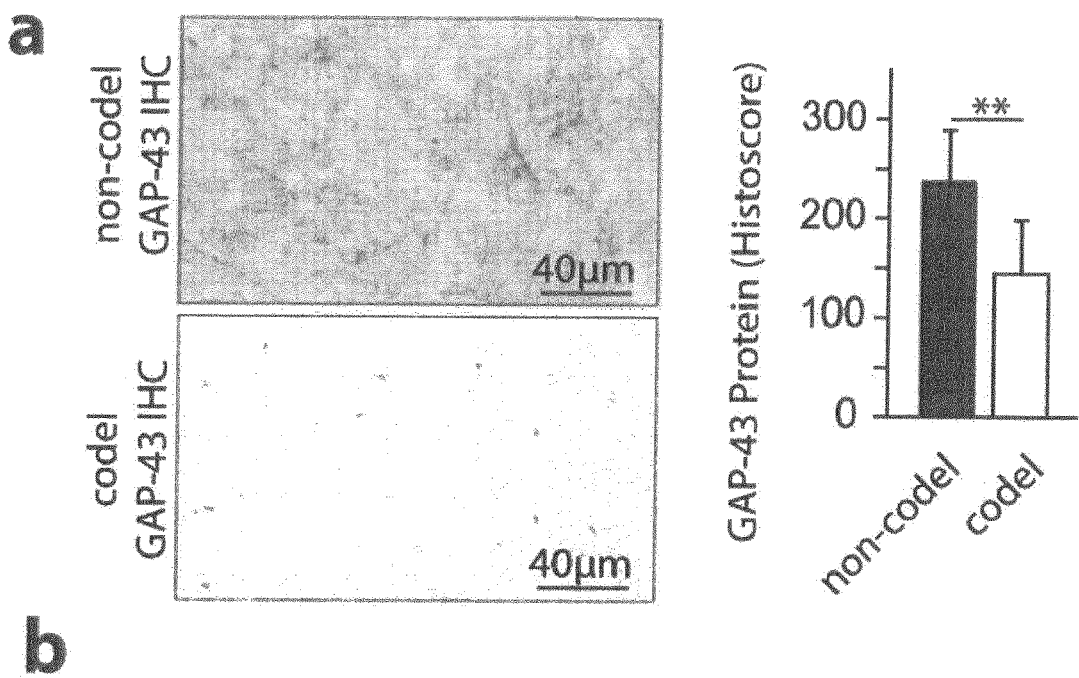
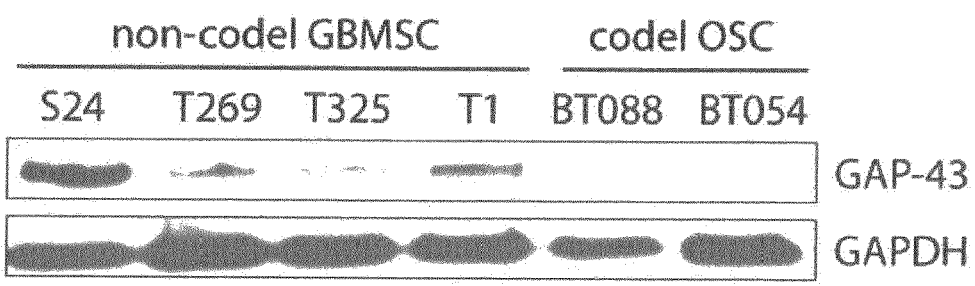
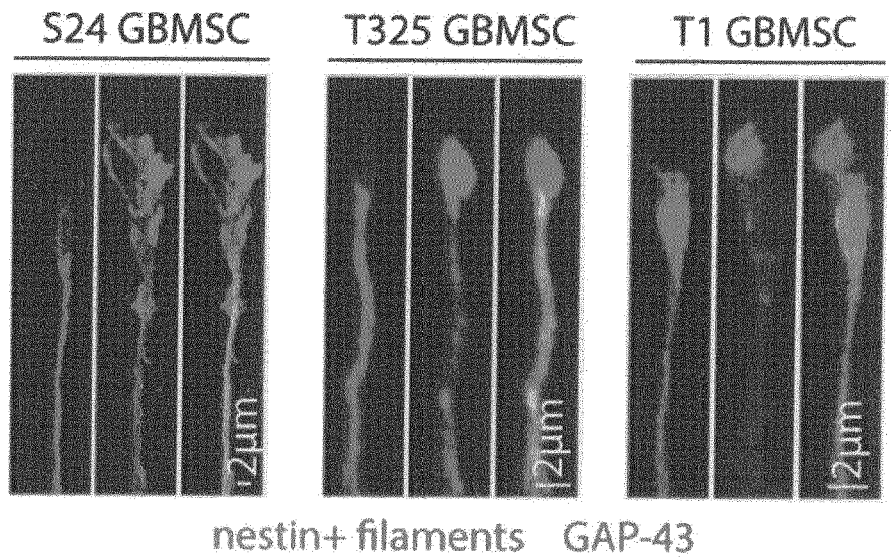
Figure 14 a, b, c

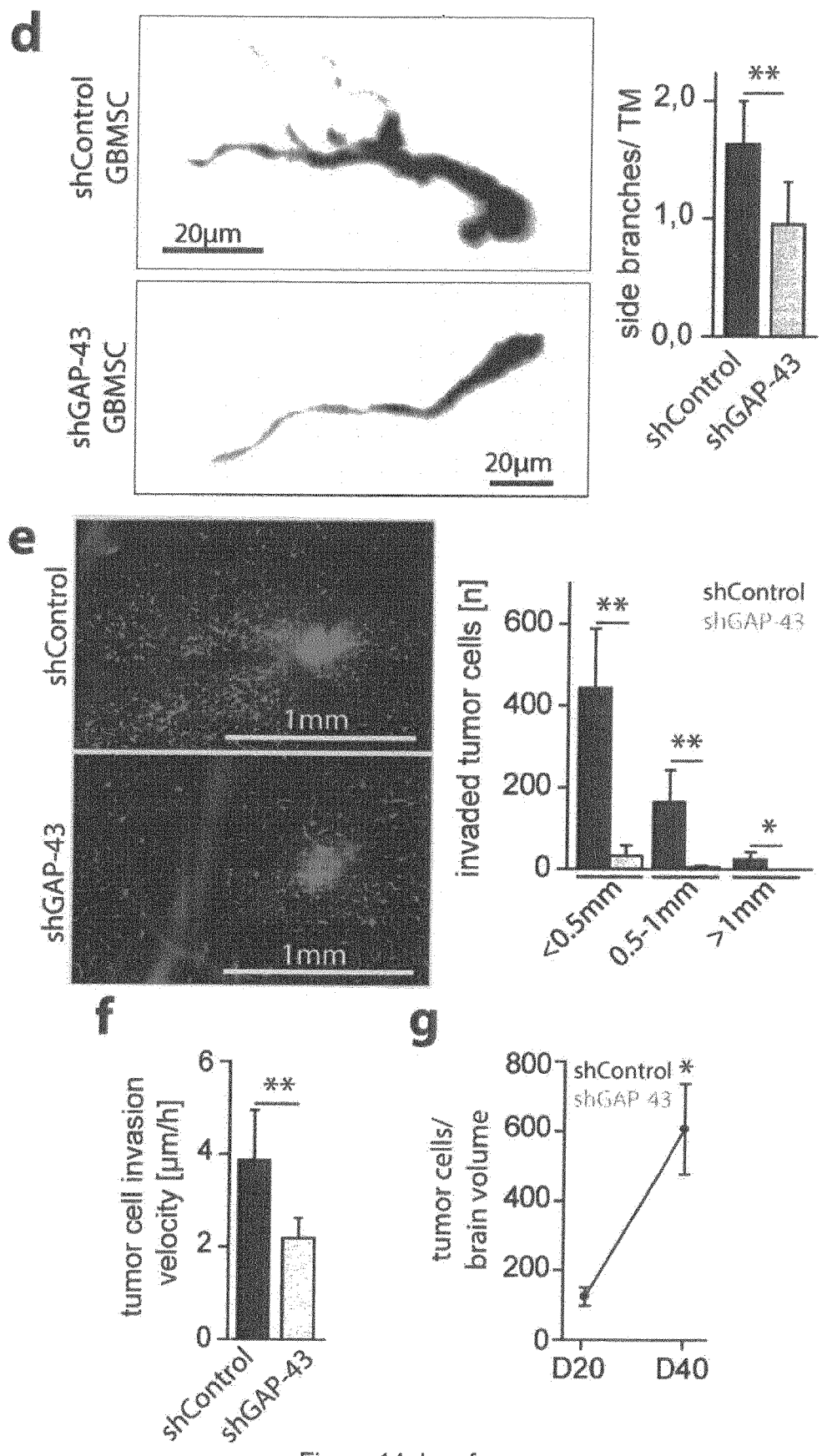
Figure 14 d, e, f, g h 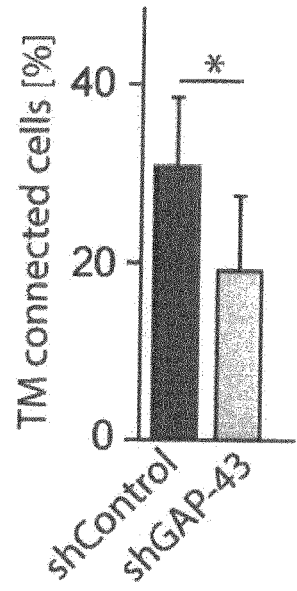 i 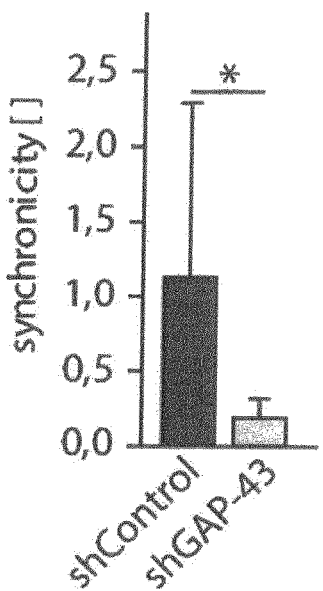
j 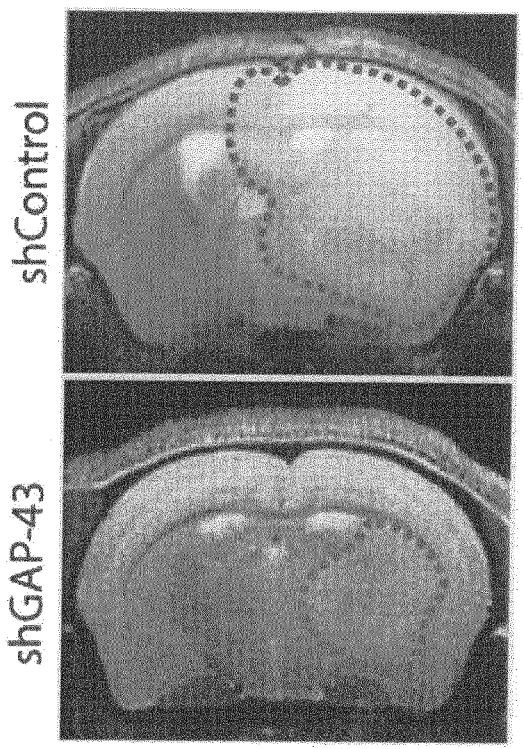 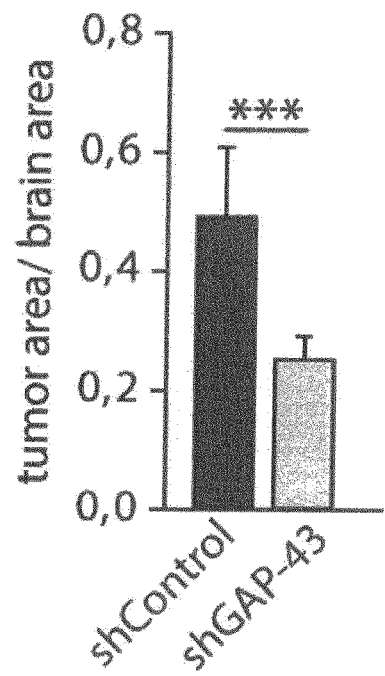
Figure 14 h, i, j

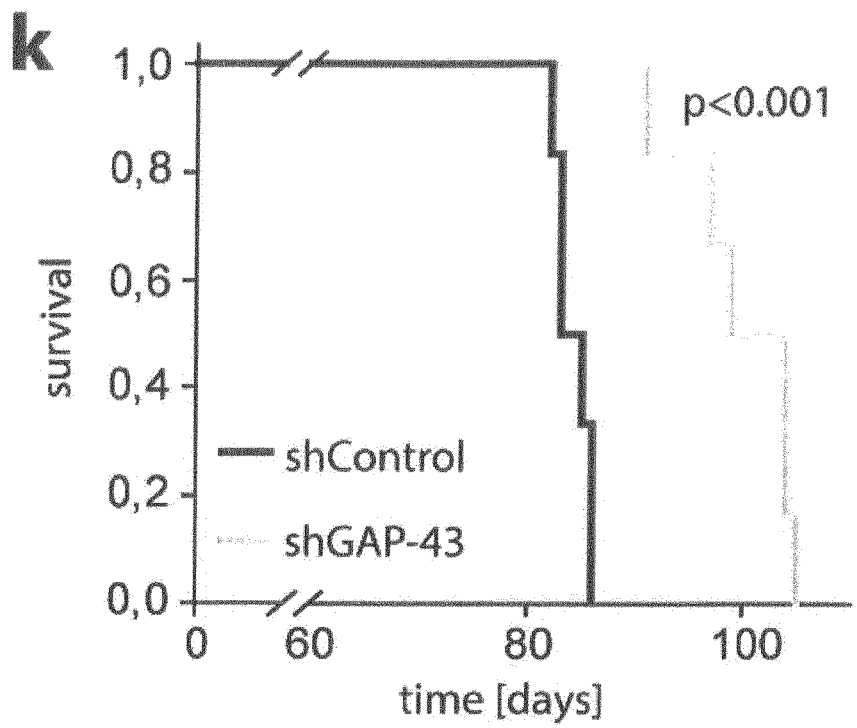
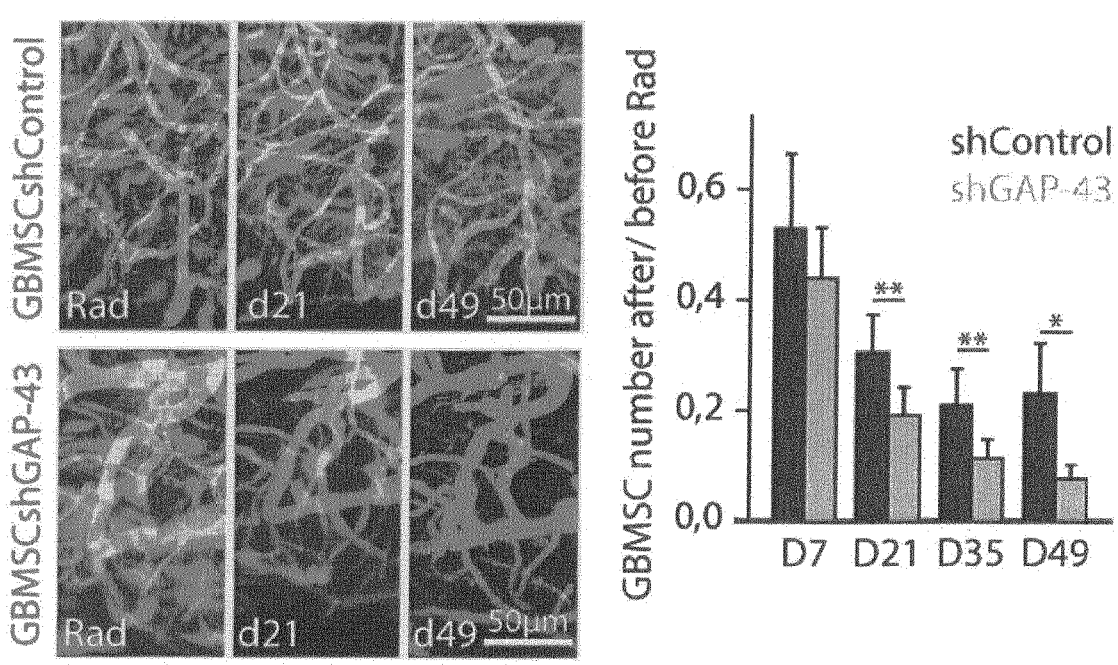
Figure 14 k, l

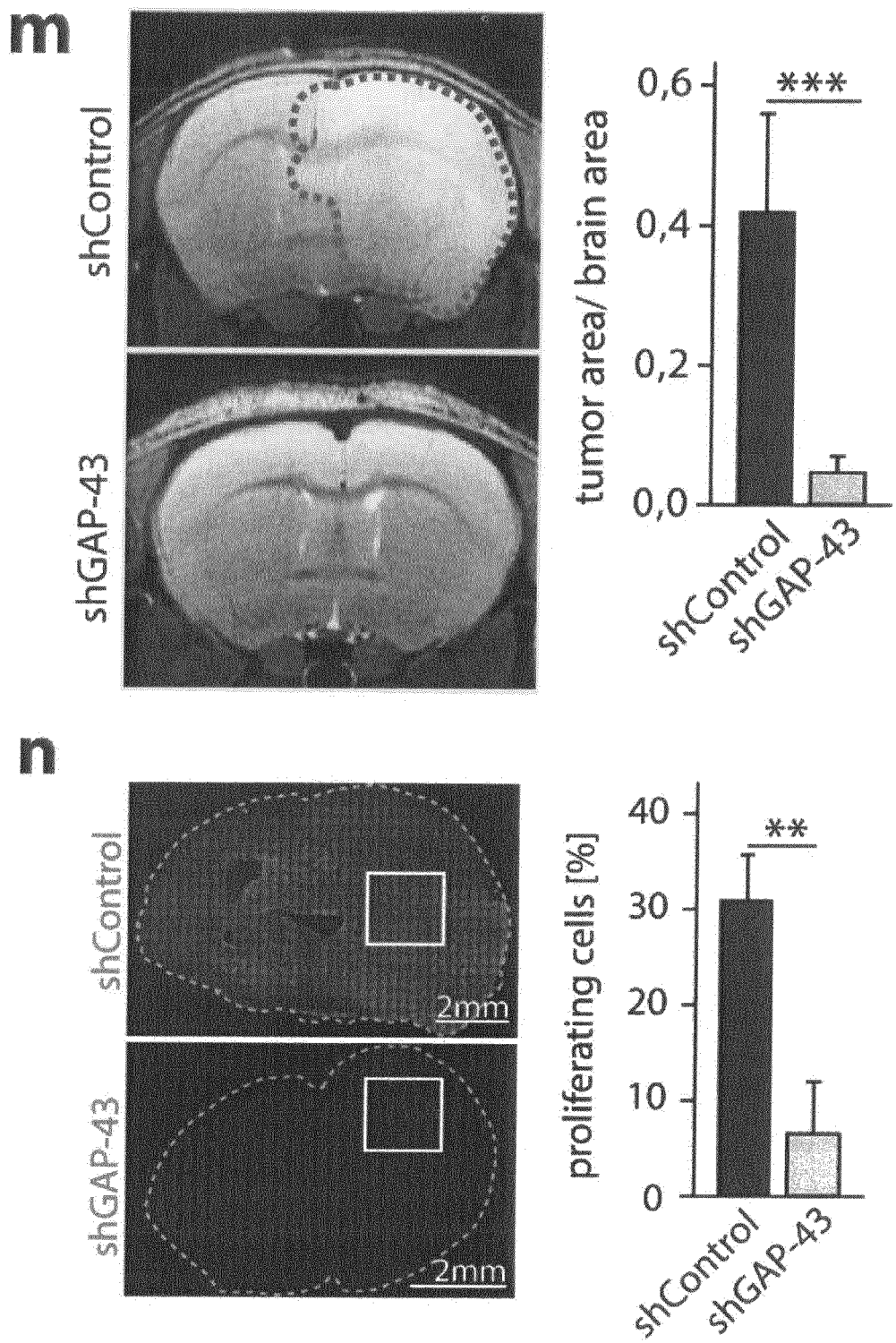
Figure 14 m, n

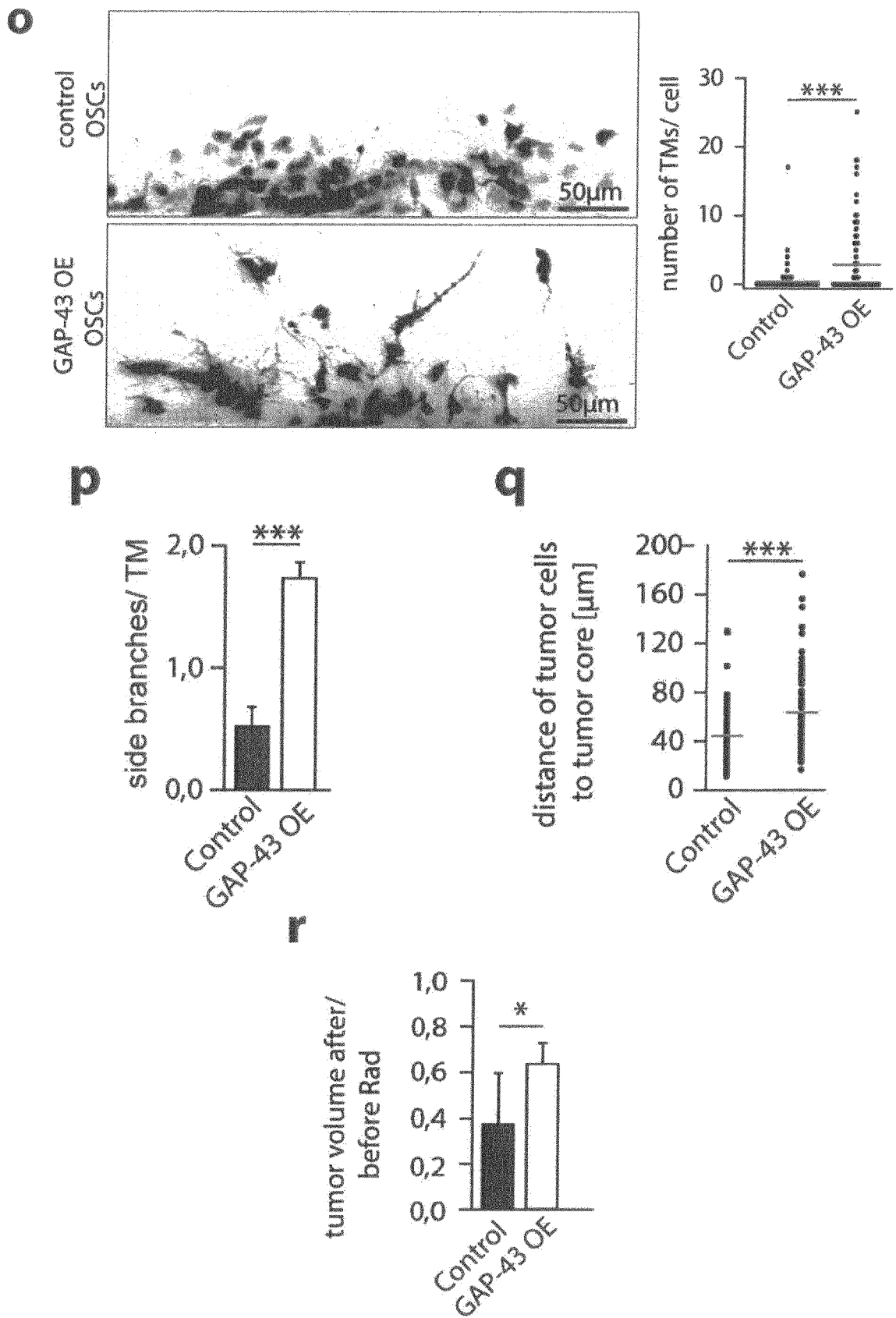
Figure 14 o, p, q, r

Figure 16:
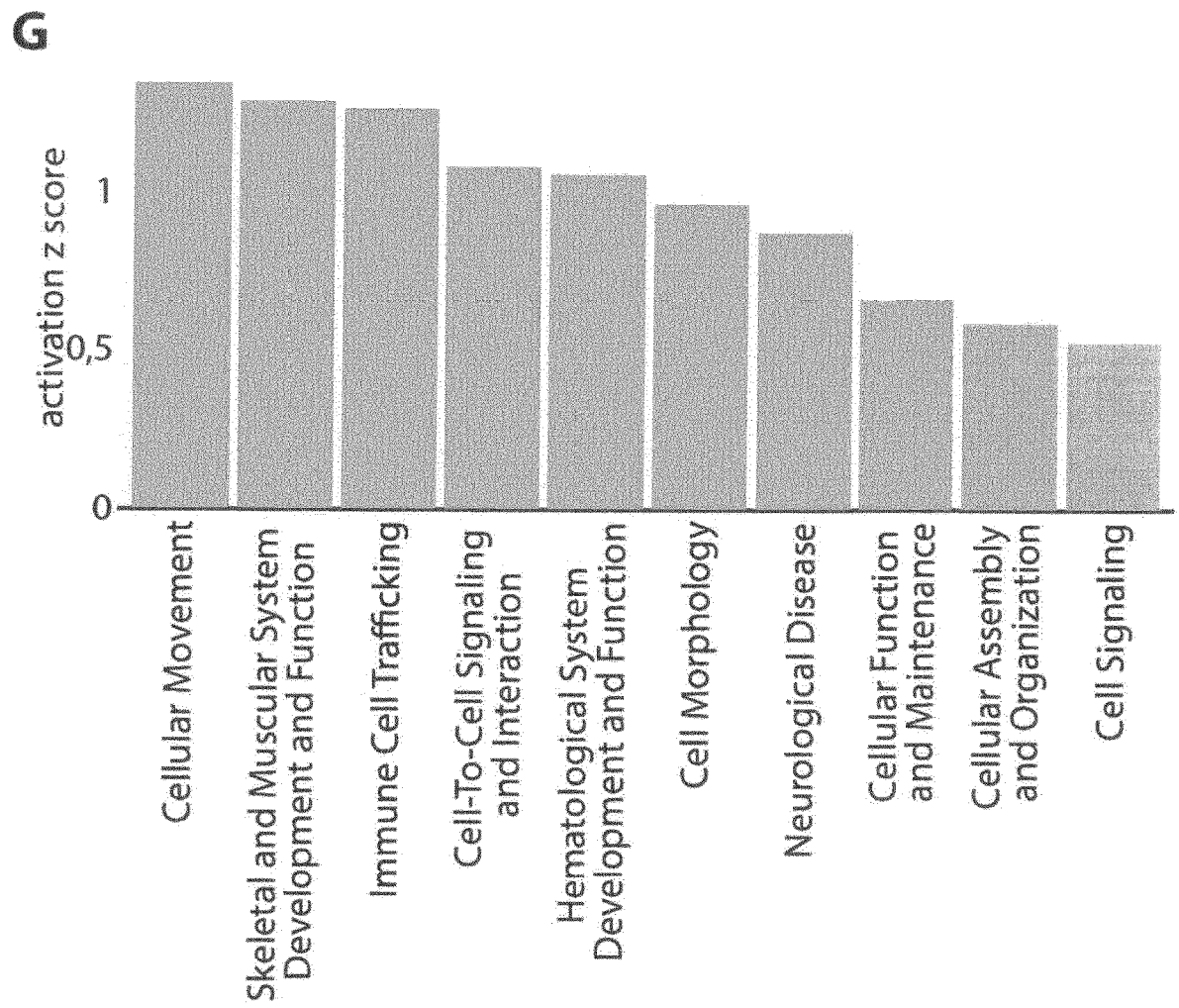

A
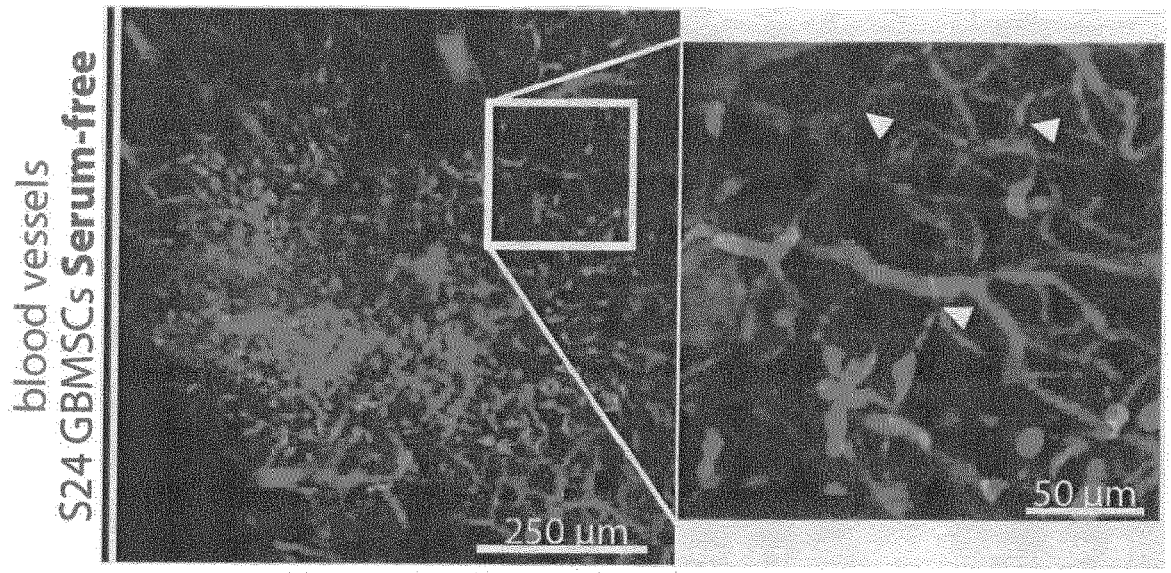
B
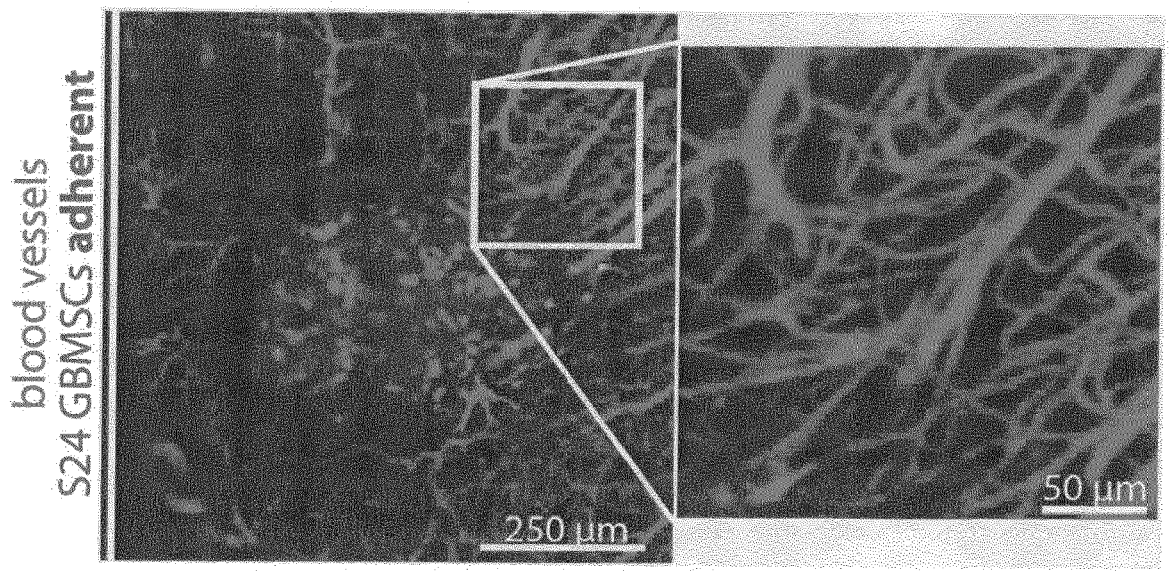
Figure 16 A, B

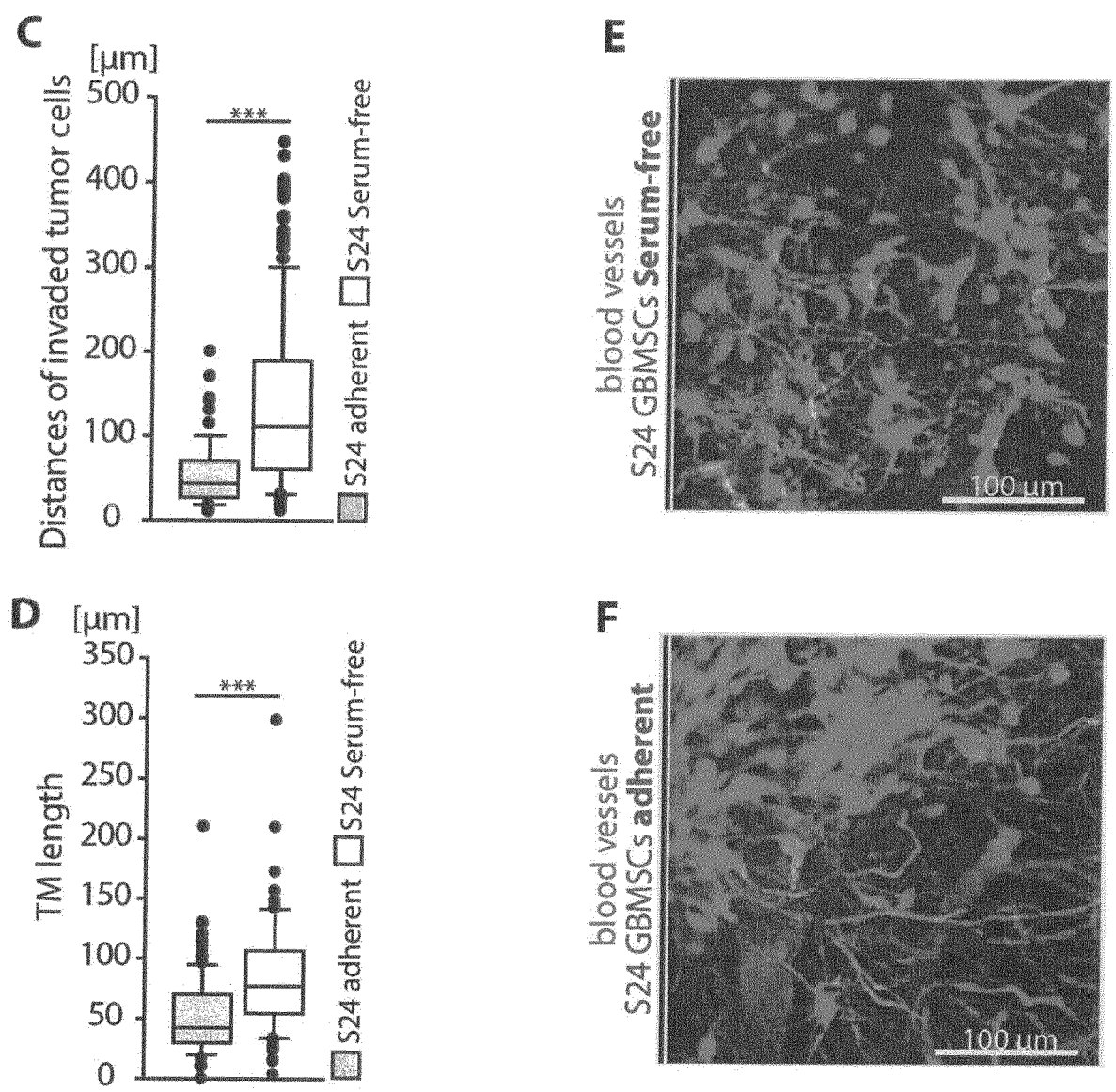
Figure 16 C-F

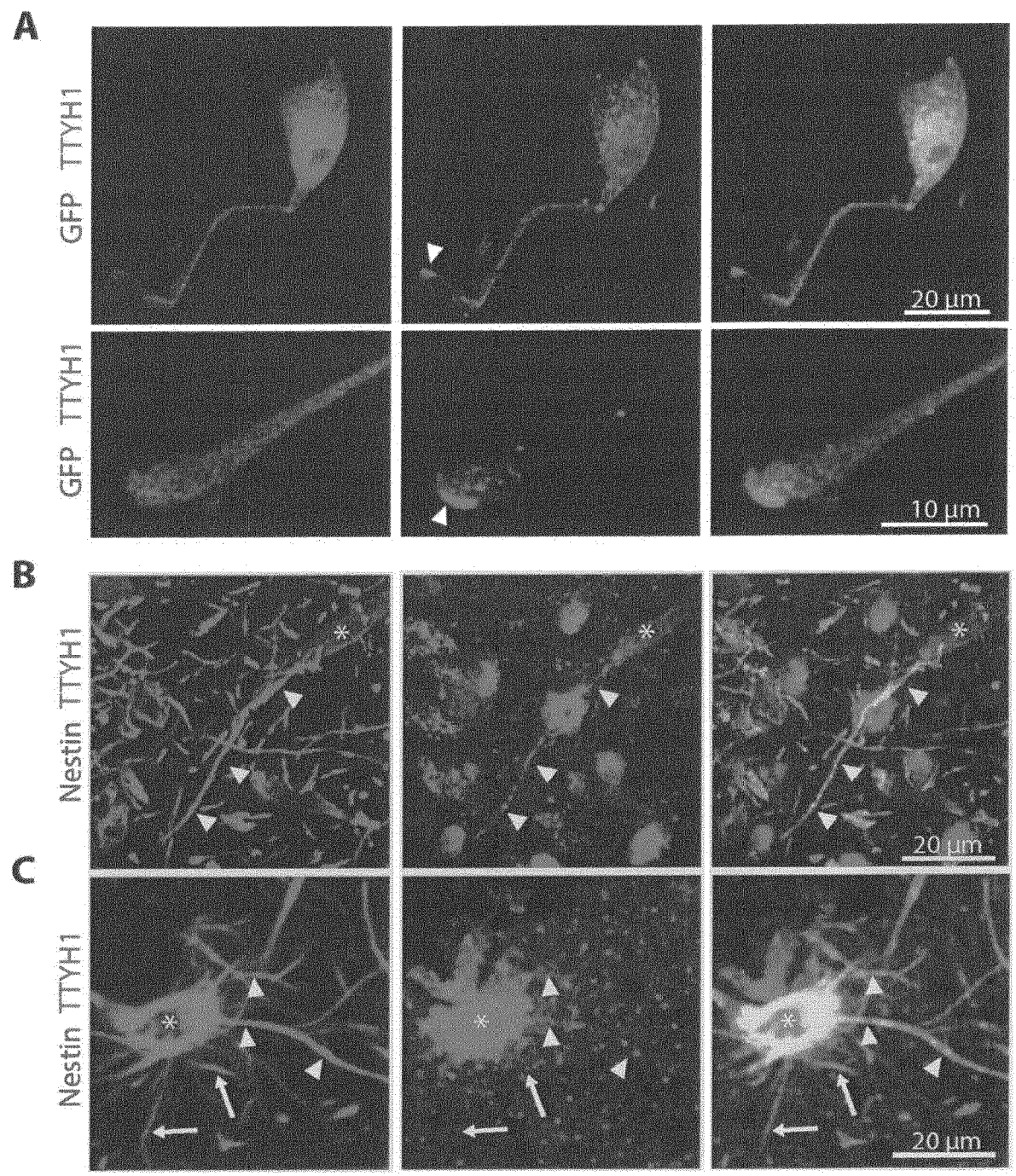
Figure 19 A-C

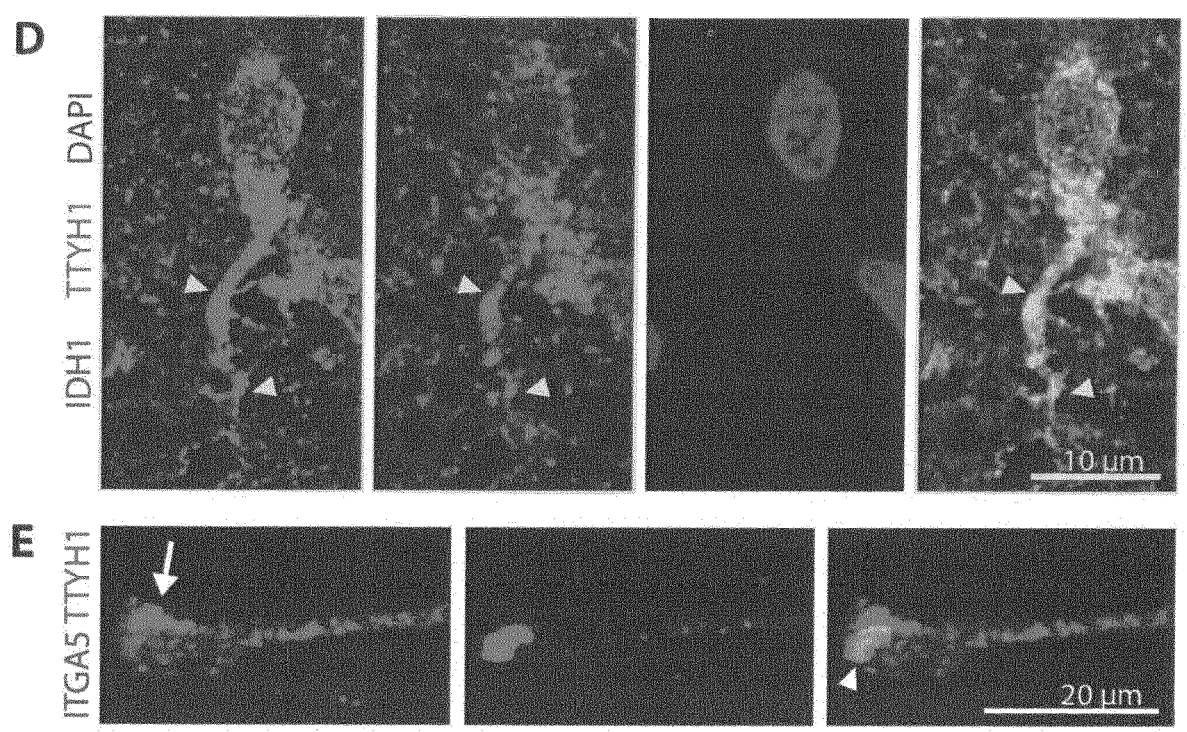
Figure 19 D, E

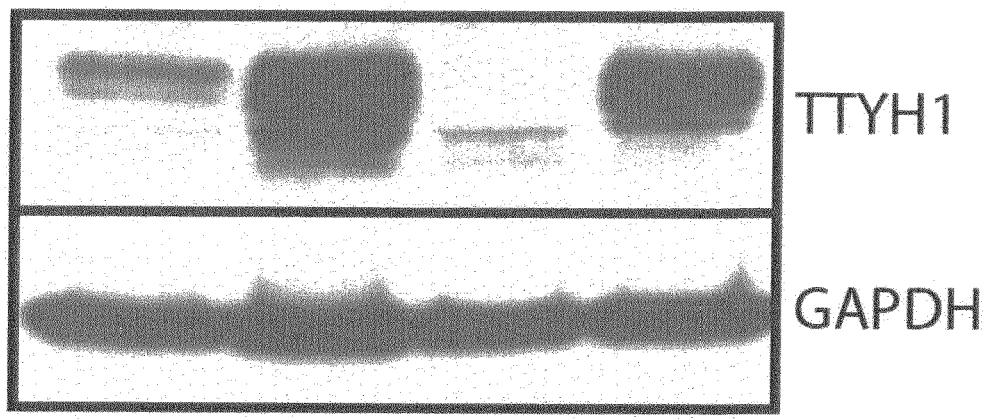
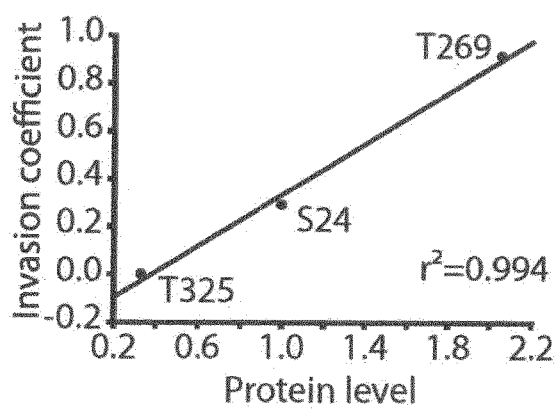
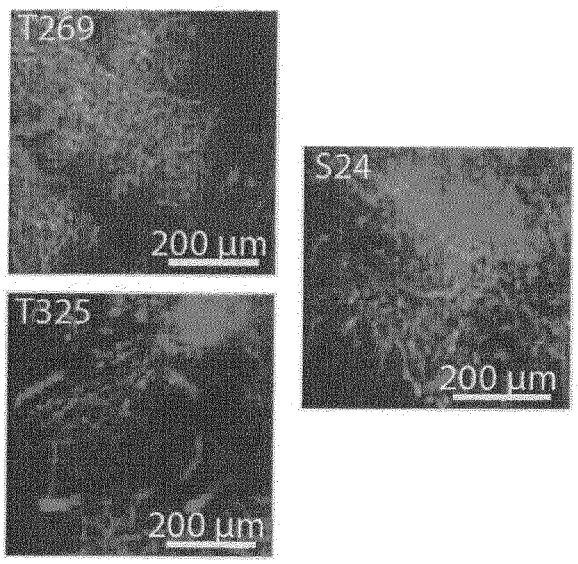
Figure 20 A, B

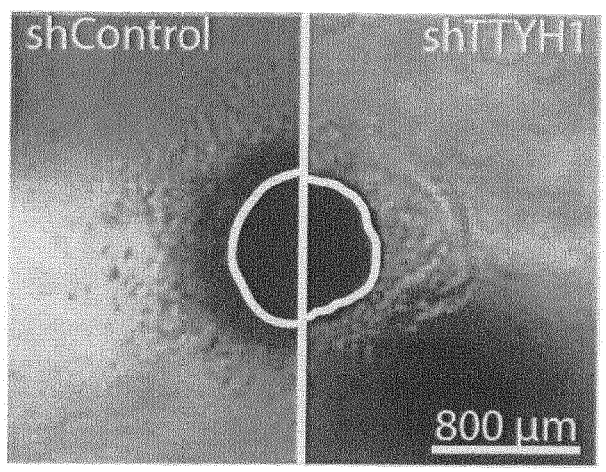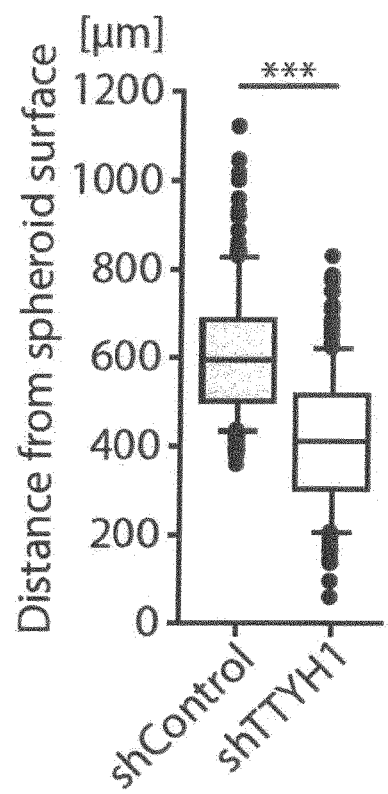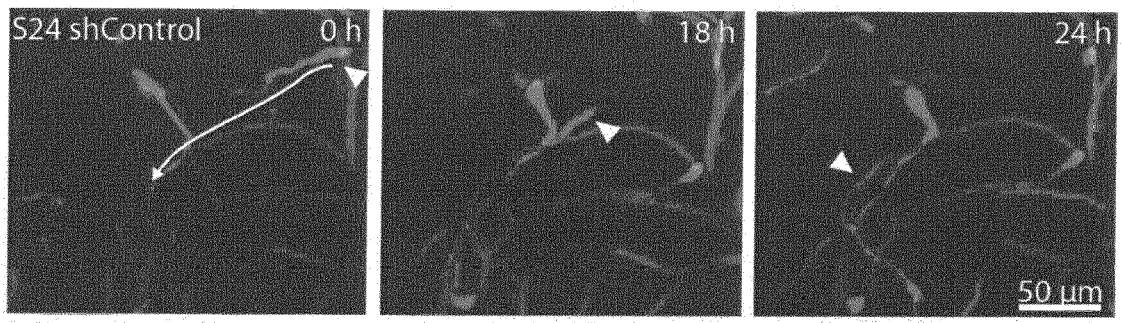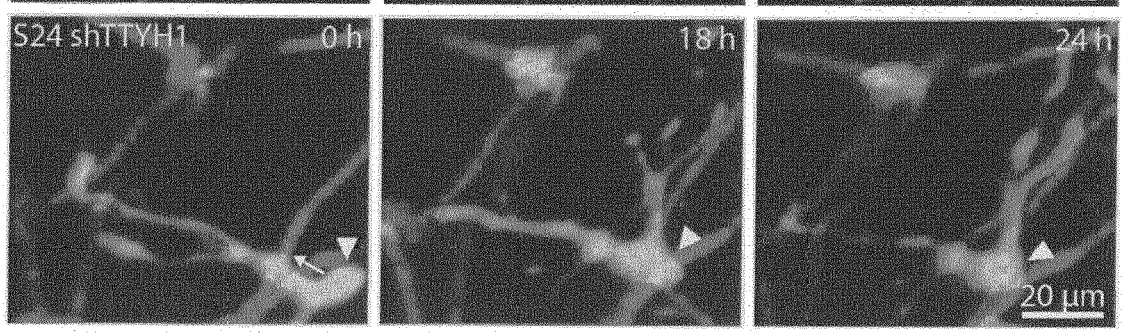
Figure 20 C-E

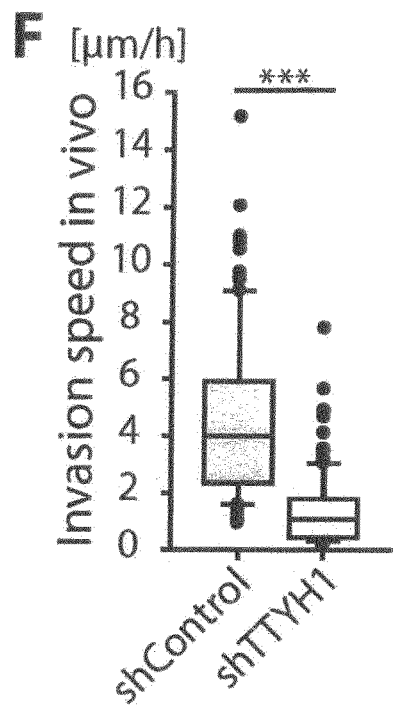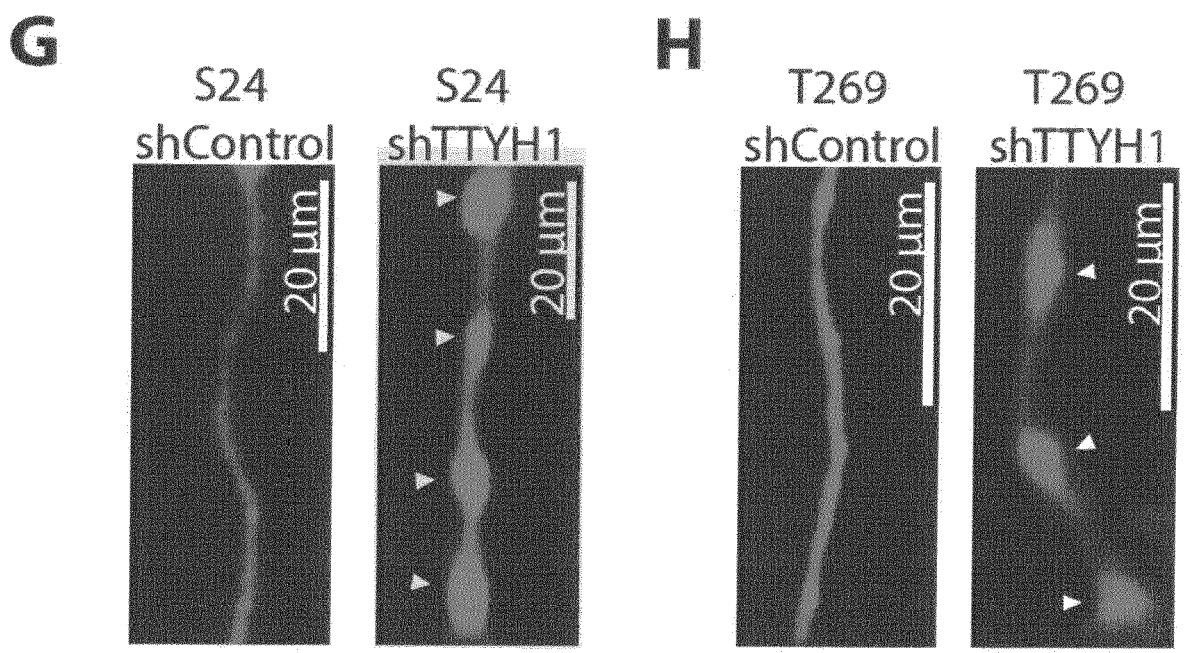
Figure 20 F-H

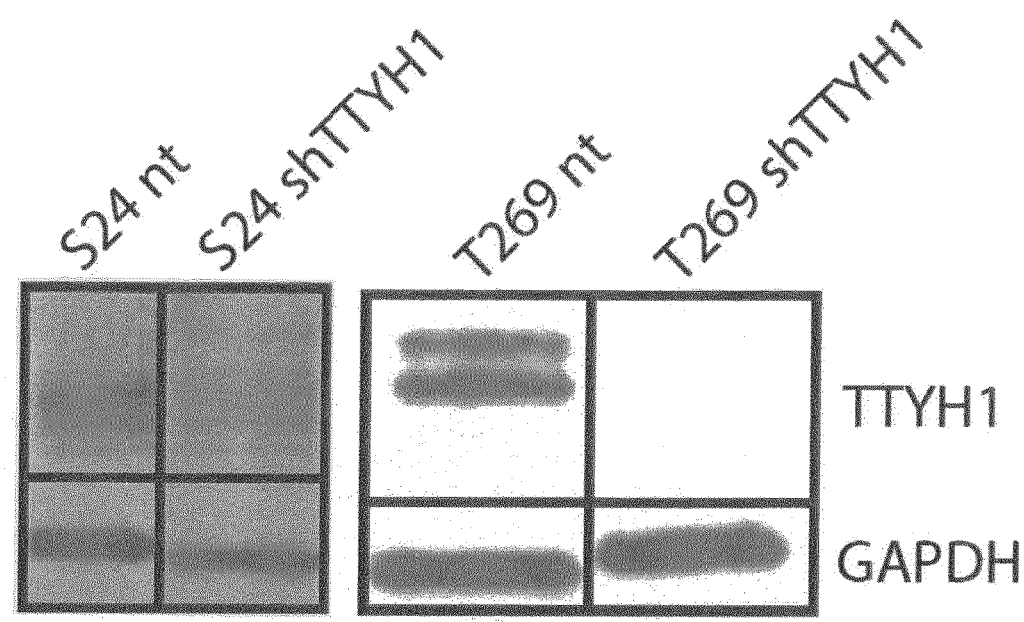
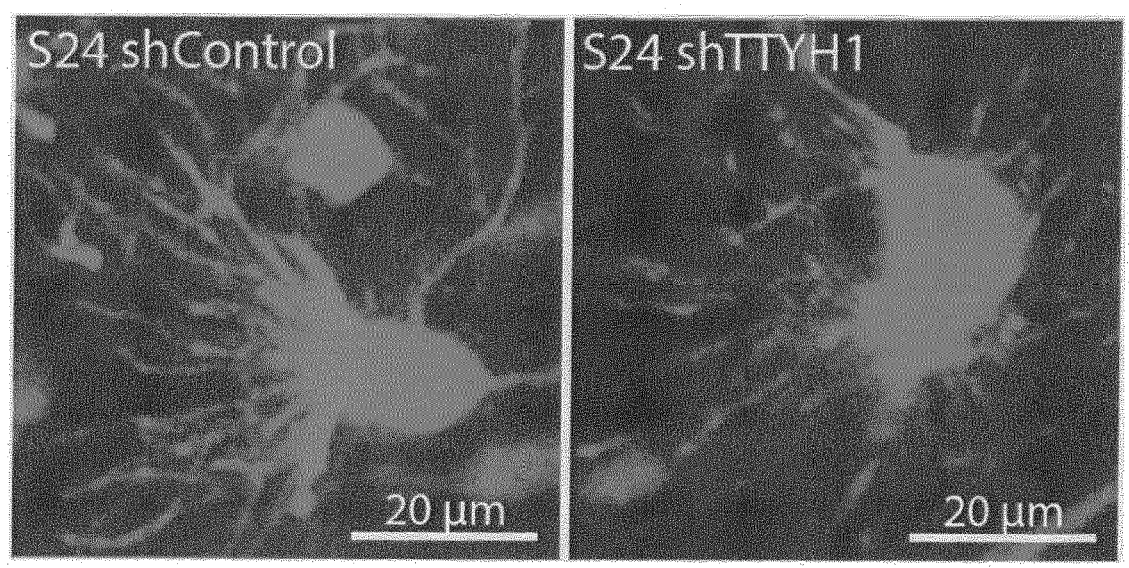
Figure 21 A, B

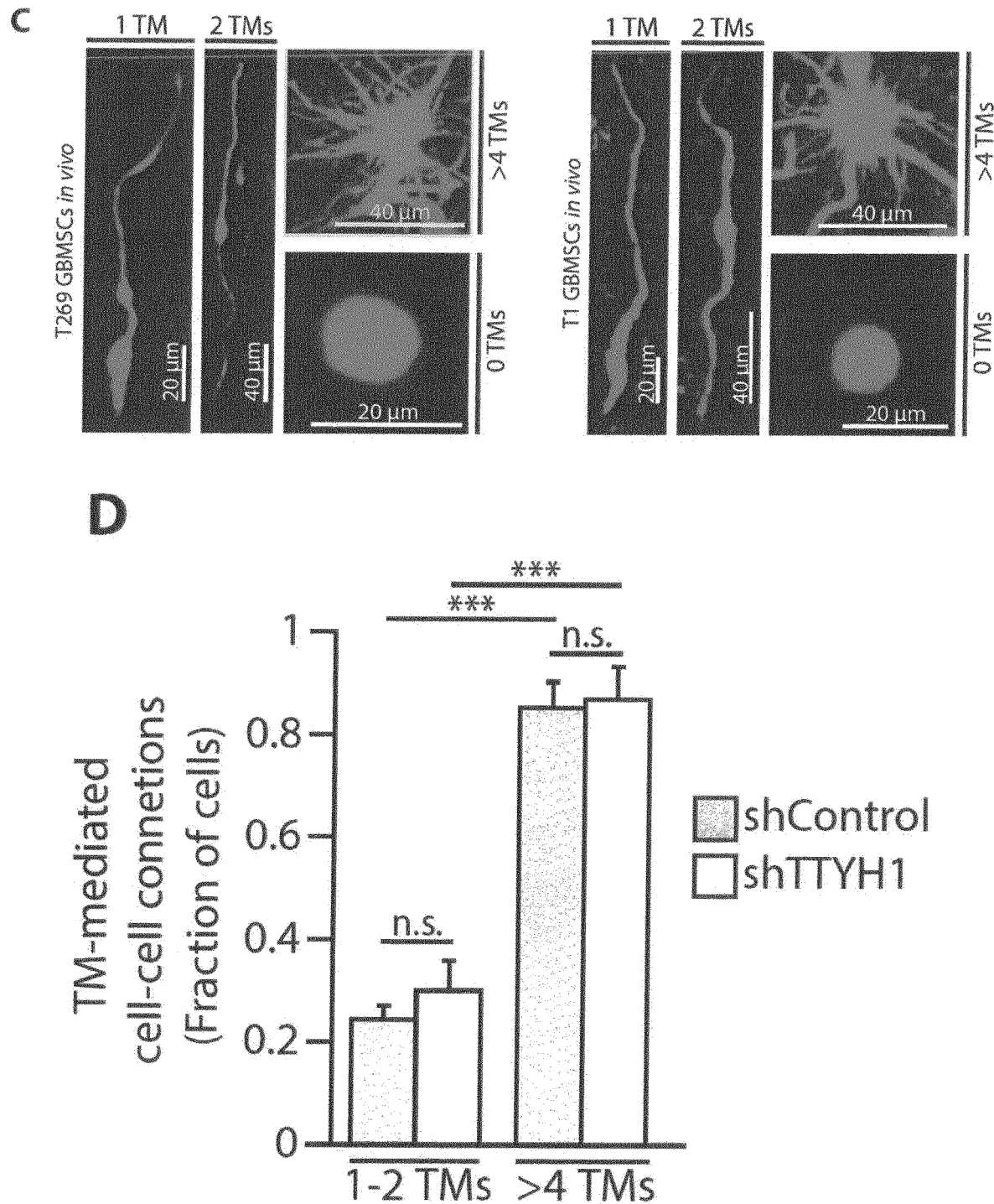
Figure 21 C, D

Figure 22:
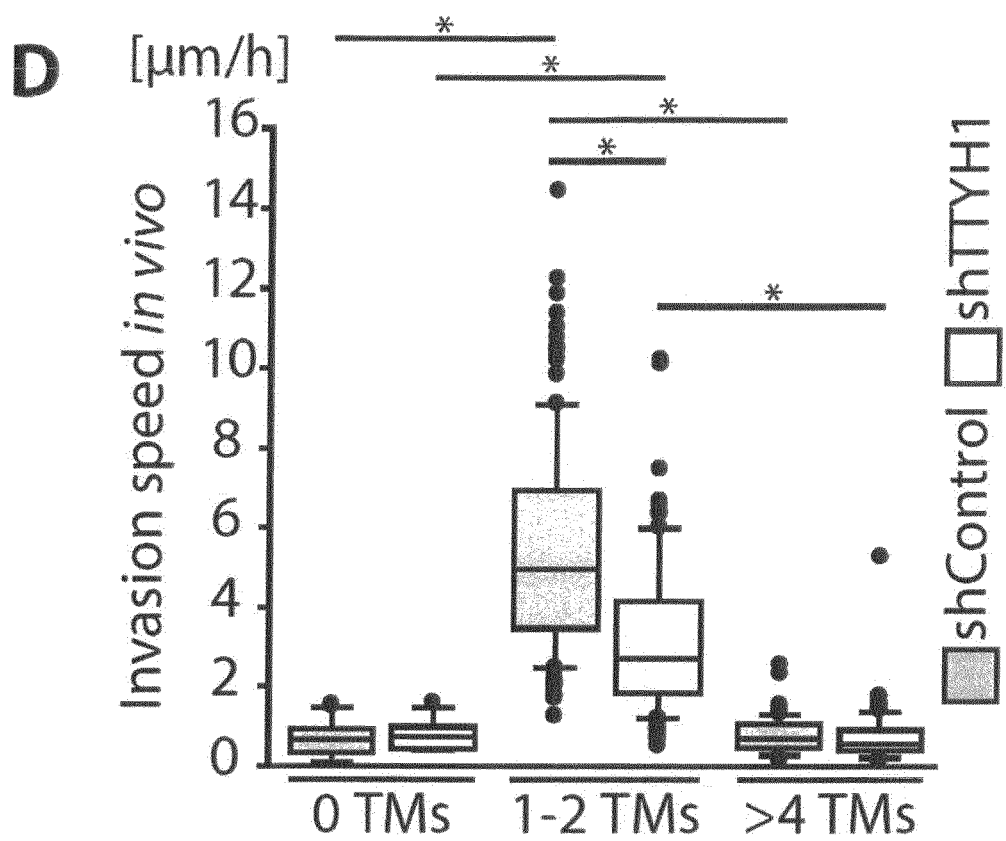

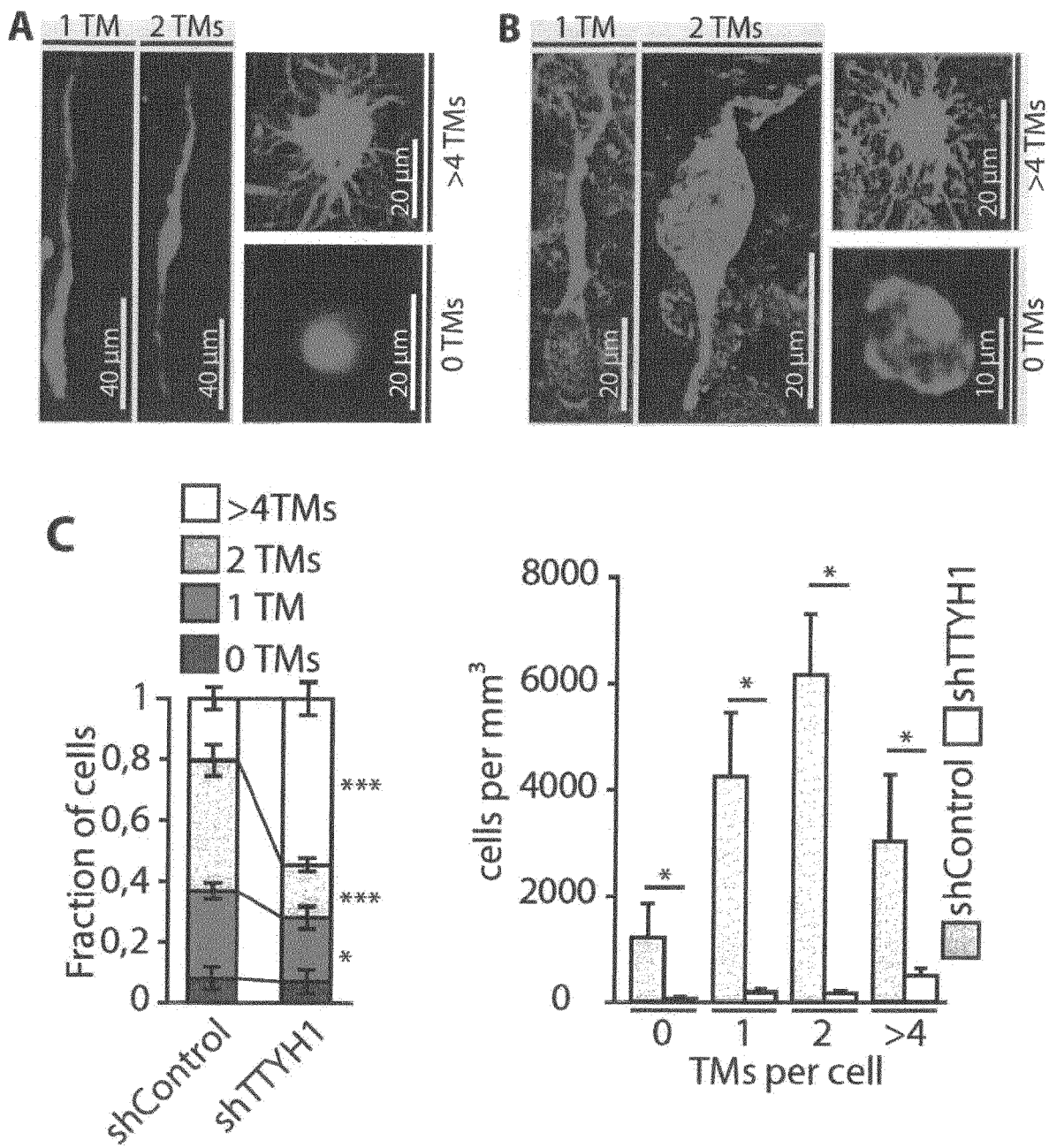
Figure 22 A-C

Figure 23:
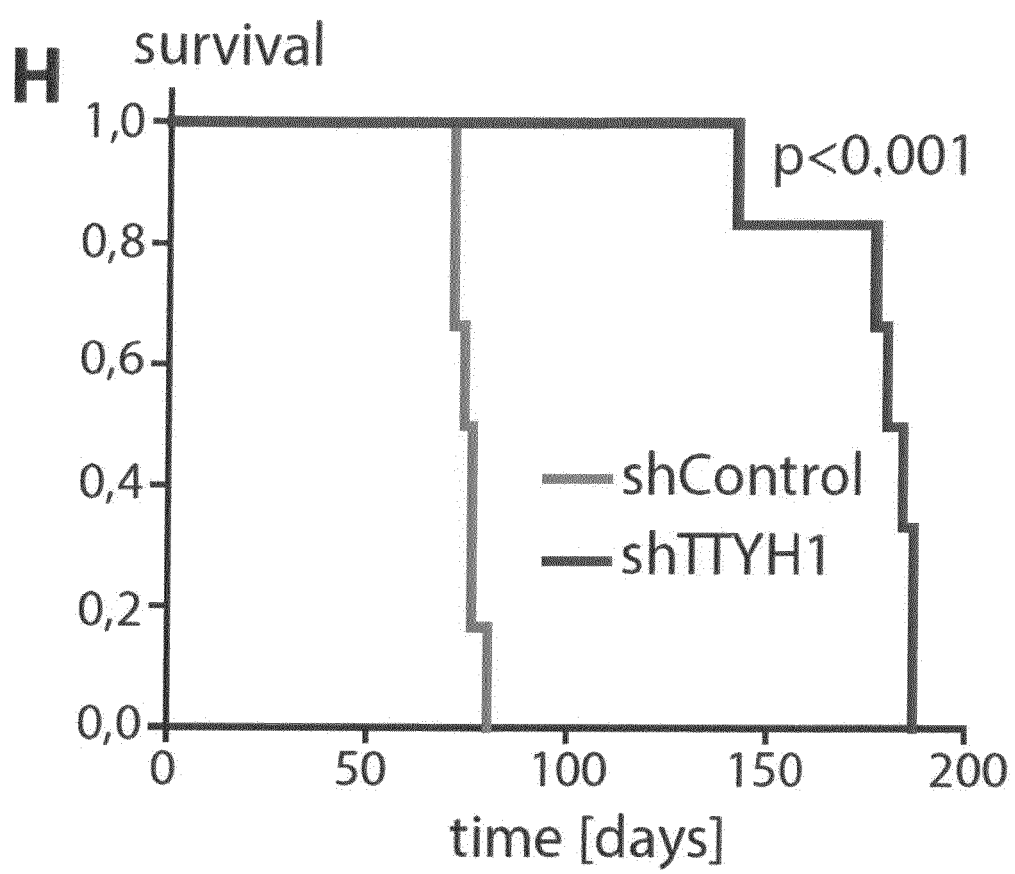

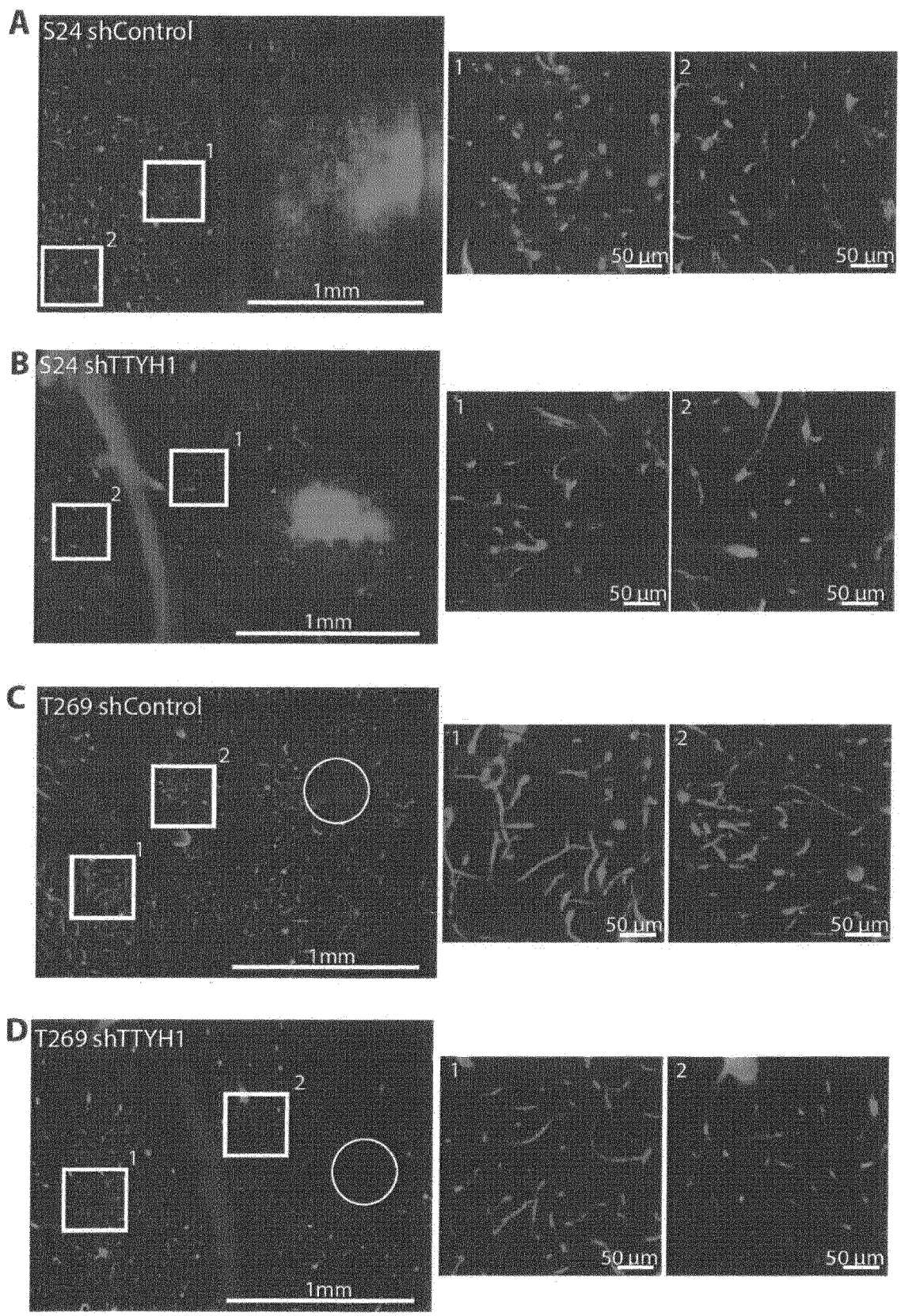
Figure 23 A-D

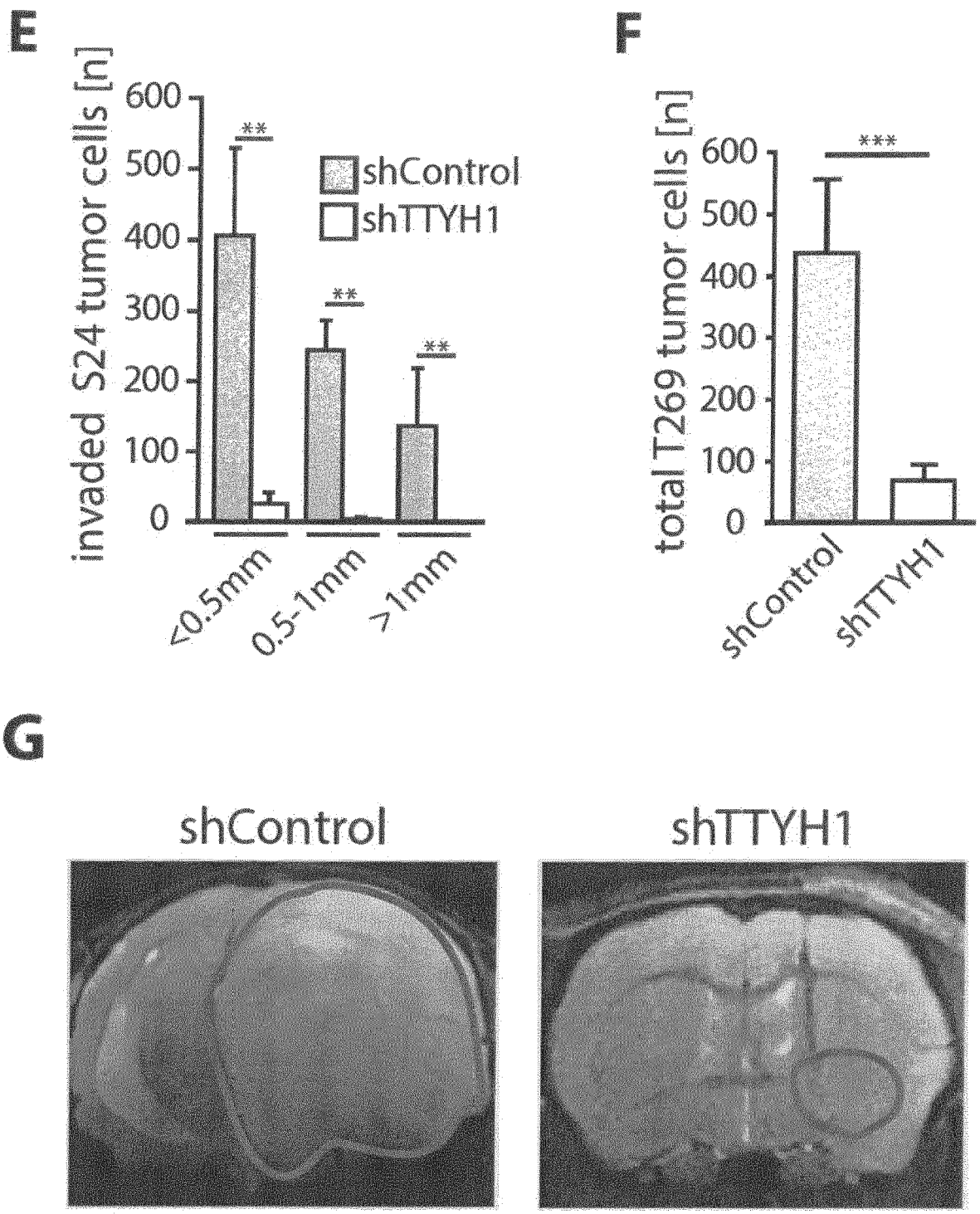
Figure 23 E-G

Figure 24:
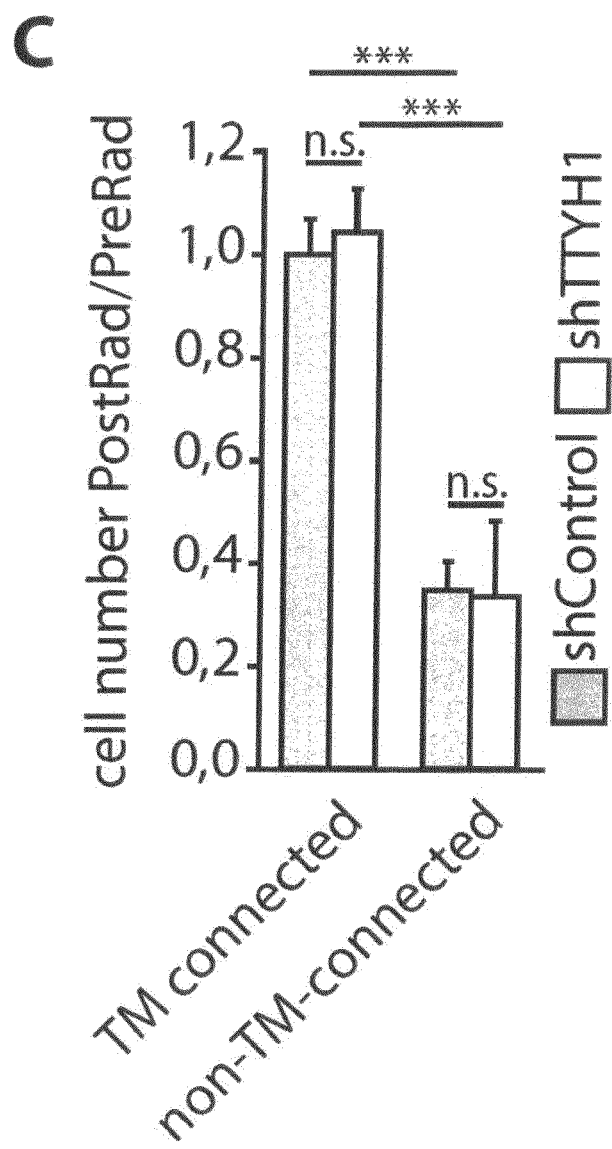

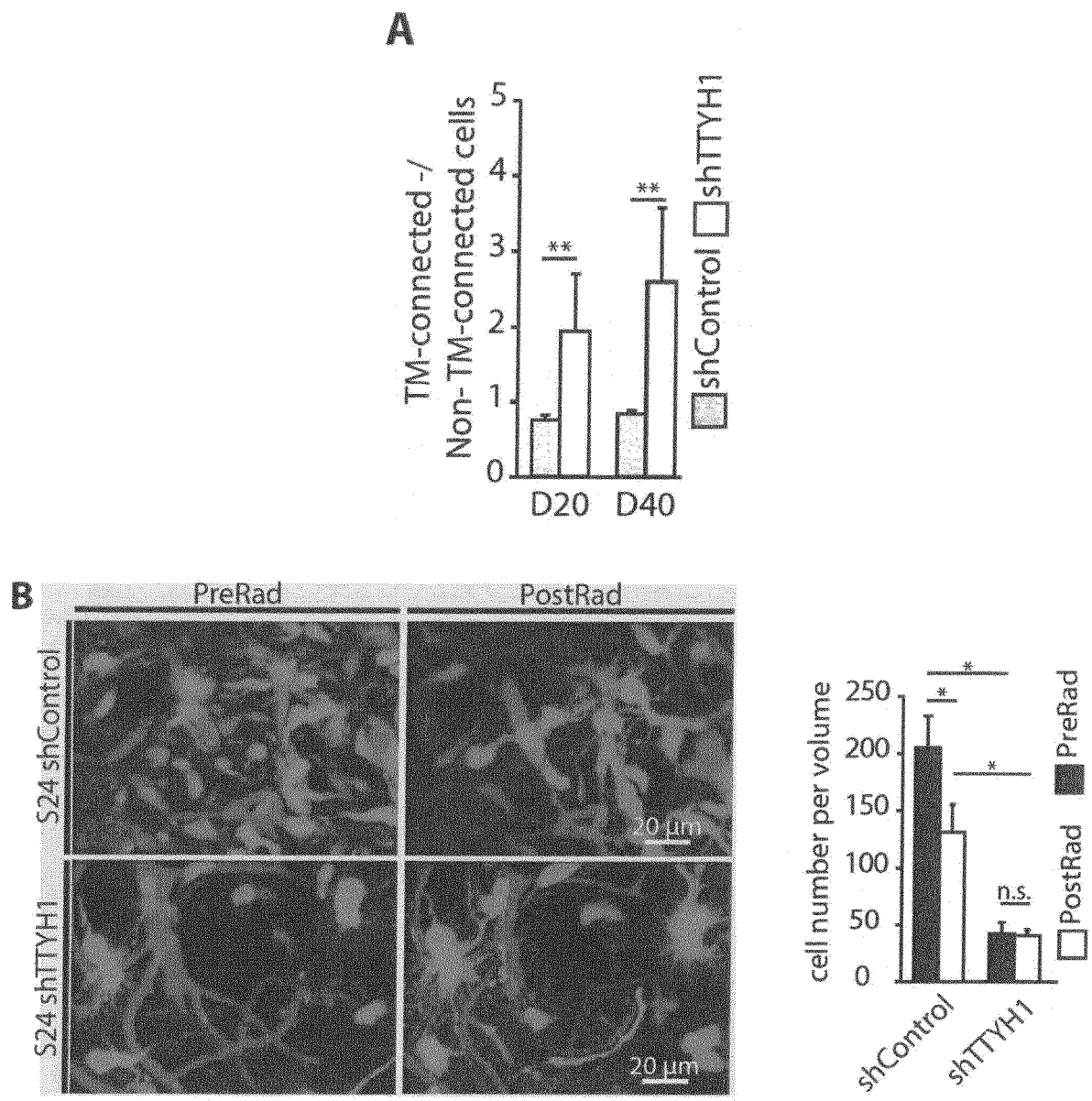
Figure 24 A, B

SEQUENCE LISTING

```
<160> NUMBER OF SEQ ID NOS: 20

<210> SEQ ID NO 1
<211> LENGTH: 21
<212> TYPE: DNA
<213> ORGANISM: Homo sapiens

<400> SEQUENCE: 1
cgtggacaca taacaaggaa a                                              21

<210> SEQ ID NO 2
<211> LENGTH: 19
<212> TYPE: DNA
<213> ORGANISM: Homo sapiens

<400> SEQUENCE: 2
ctgaagctaa taagaagga                                                 19

<210> SEQ ID NO 3
<211> LENGTH: 21
<212> TYPE: DNA
```

```
<213> ORGANISM: Homo sapiens

<400> SEQUENCE: 3
tgtagatgaa accaaaccta a                                              21

<210> SEQ ID NO 4
<211> LENGTH: 21
<212> TYPE: DNA
<213> ORGANISM: Homo sapiens

<400> SEQUENCE: 4
ccactaaagc ttccactgat a                                              21

<210> SEQ ID NO 5
<211> LENGTH: 20
<212> TYPE: DNA
<213> ORGANISM: Homo sapiens

<400> SEQUENCE: 5
tcaaacagtg tggcttaaac                                                20

<210> SEQ ID NO 6
<211> LENGTH: 17
<212> TYPE: DNA
<213> ORGANISM: Artificial Sequence
<220> FEATURE:
<223> OTHER INFORMATION: GAP43 antisense oligonucleotide

<400> SEQUENCE: 6
gcacagcatg atcgtat                                                   17

<210> SEQ ID NO 7
<211> LENGTH: 18
<212> TYPE: DNA
<213> ORGANISM: Artificial Sequence
<220> FEATURE:
<223> OTHER INFORMATION: GAP43 antisense oligonucleotide

<400> SEQUENCE: 7
tttgttcttc tcatacag                                                  18

<210> SEQ ID NO 8
<211> LENGTH: 17
<212> TYPE: DNA
<213> ORGANISM: Artificial Sequence
<220> FEATURE:
<223> OTHER INFORMATION: GAP43 antisense oligonucleotide

<400> SEQUENCE: 8
acagcatctg tcttctc                                                   17

<210> SEQ ID NO 9
<211> LENGTH: 17
<212> TYPE: RNA
<213> ORGANISM: Artificial Sequence
<220> FEATURE:
<223> OTHER INFORMATION: GAP43 asRNA

<400> SEQUENCE: 9
gcacagcaug aucguau                                                   17

<210> SEQ ID NO 10
<211> LENGTH: 18
<212> TYPE: RNA
<213> ORGANISM: Artificial Sequence
```

```
<220> FEATURE:
<223> OTHER INFORMATION: GAP43 asRNA

<400> SEQUENCE: 10
uuuguucuuc ucauacag                                                    18

<210> SEQ ID NO 11
<211> LENGTH: 17
<212> TYPE: RNA
<213> ORGANISM: Artificial Sequence
<220> FEATURE:
<223> OTHER INFORMATION: GAP43 asRNA

<400> SEQUENCE: 11
acagcaucug ucuucuc                                                     17

<210> SEQ ID NO 12
<211> LENGTH: 21
<212> TYPE: DNA
<213> ORGANISM: Homo sapiens

<400> SEQUENCE: 12
tcagacatcc tgagctatta t                                                21

<210> SEQ ID NO 13
<211> LENGTH: 21
<212> TYPE: DNA
<213> ORGANISM: Homo sapiens

<400> SEQUENCE: 13
cttggaggag actctgaatg t                                                21

<210> SEQ ID NO 14
<211> LENGTH: 21
<212> TYPE: DNA
<213> ORGANISM: Homo sapiens

<400> SEQUENCE: 14
ctccaatcca gacccttatg t                                                21

<210> SEQ ID NO 15
<211> LENGTH: 21
<212> TYPE: DNA
<213> ORGANISM: Homo sapiens

<400> SEQUENCE: 15
atcggtttct atggcaacag t                                                21

<210> SEQ ID NO 16
<211> LENGTH: 21
<212> TYPE: DNA
<213> ORGANISM: Homo sapiens

<400> SEQUENCE: 16
gctctgacca ctaacactct t                                                21

<210> SEQ ID NO 17
<211> LENGTH: 13
<212> TYPE: PRT
<213> ORGANISM: Artificial Sequence
<220> FEATURE:
<223> OTHER INFORMATION: gap junction blocking peptide Gap 26
```

```
<400> SEQUENCE: 17

Val Cys Tyr Asp Lys Ser Phe Pro Ile Ser His Val Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: gap junction blocking peptide Gap 27

<400> SEQUENCE: 18

Ser Arg Pro Thr Glu Lys Thr Ile Phe Ile Ile
1               5                   10

<210> SEQ ID NO 19
<211> LENGTH: 21
<212> TYPE: DNA
<213> ORGANISM: Homo sapiens

<400> SEQUENCE: 19
ccgggacatc acggatcata t                                     21

<210> SEQ ID NO 20
<211> LENGTH: 21
<212> TYPE: DNA
<213> ORGANISM: Homo sapiens

<400> SEQUENCE: 20
gcccaaactg atggtgtcaa t                                     21
```

AGENTS FOR USE IN THE TREATMENT OF GLIOMA

The present invention relates to agents for use in the treatment of glioma, in particular astrocytoma WHO II° and III°, as well as IV° (glioblastoma), in a subject.

INCORPORATION BY REFERENCE OF SEQUENCE LISTING

The Sequence Listing in the ASCII text file, named as 37496_SubstituteSequenceListing.txt of 4 KB, created on Dec. 17, 2020, and submitted to the United States Patent and Trademark Office via EFS-Web, is incorporated herein by reference.

Gliomas such as astrocytic brain tumors, including glioblastomas, are incurable neoplasms characterized by diffusely infiltrative growth. Astrocytomas (WHO II°, III°, IV°=glioblastomas) are prototypical examples for highly invasive tumors that diffusely colonize their host organ, which ultimately leads to neurological dysfunction and death despite intensive radio- and chemotherapy. The cellular and/or molecular mechanisms of invasiveness and resistance to therapy are so far not well understood. Classical therapy of astrocytoma including glioblastoma includes surgical resection of the solid part of the tumor, radiotherapy and chemotherapy. However, these therapies can so far only delay disease progression. There are no cases known in which astrocytoma or glioblastoma could be cured.

Oligodendrogliomas share the infiltrative growth pattern in the brain, but are far more vulnerable to therapeutic intervention than astrocytomas. The presence of their characteristic 1p/19q codeletion is associated with a high responsiveness to combined radio- and chemotherapy in oligodendrogliomas, and makes them prone to apoptosis even without therapy. The reason for that remains unclear, just as the specific mechanism(s) of resistance in astrocytomas.

Accordingly, the technical problem underlying the present invention is to provide novel agents for use in the treatment of glioma, in particular astrocytoma and glioblastoma, in a subject.

The solution to the above technical problem is achieved by the embodiments characterized in the claims.

In particular, in a first aspect, the present invention relates to an agent for use in the treatment of glioma in a subject, wherein said agent is capable of interfering with tumor microtube (TM)-mediated (a) invasion and/or (b) proliferation and/or (c) intracellular communication and/or (d) resistance to conventional cytotoxic therapies such as radiotherapy and/or chemotherapy of glioma cells.

Preferably, said agent is selected from the group consisting of (a) an agent that is capable of mediating RNA interference (RNAi) for the specific knockdown of the growth associated protein 43 (GAP43) gene,
(b) a compound that is capable of inhibiting the biological activity of GAP43 protein,
(c) a xanthine derivative,
(d) a small molecule inhibitor of nitric oxide synthase 2 (NOS2),
(e) a small molecule inhibitor of transforming growth factor beta (TGF-beta),
(f) a small molecule inhibitor of caspase 3,
(g) a compound that is capable of blocking the N-methyl-D-aspartate (NMDA) receptor,
(h) an agent that is capable of mediating RNAi for the specific knockdown of the human tweety homologue 1 (Ttyh1) gene,
(i) a compound that is capable of inhibiting the biological activity of TTYH-1 protein,
(j) an agent that is capable of mediating RNA interference (RNAi) for the specific knockdown of the connexin 43 (Cx43) gene,
(k) a compound that is capable of blocking gap junctions, in particular that is capable of inhibiting the biological activity of connexin 43 (Cx43).

The present invention is based on the finding that many tumor cells in gliomas, in particular in astrocytomas and glioblastomas, extend ultra-long membrane protrusions, both in brains of living mice and in patient samples. These protrusions, for which the term tumor microtubes (TMs) is proposed, have distinct anatomical and functional features. Astrocytoma cells use TMs as routes for brain invasion, proliferation, and to interconnect with other infiltrating cells over long distances. The resulting TM-linked cellular network allows intercellular exchange of molecules through connexin 43 (Cx43) gap junctions, including communication by intercellular calcium waves (ICWs). TMs are used to sense injury to network members, and to execute a damage repair. Moreover, the TM-connected astrocytoma cells, but not those remaining unconnected throughout tumor progression, are protected from cell death inflicted by radiotherapy. Retention of chromosomes 1p and 19q was required for intercellular TM formation, and for high expression of the neuronal growth-associated proteins GAP43 and Ttyh1. Knockdown of GAP43 inhibited TM formation and TM-driven tumor cell interconnection, which resulted in markedly reduced astrocytoma progression and radioresistance. Knockdown of Ttyh1 dramatically inhibited TM-driven astrocytoma growth and invasion, making tumors unable to grow to a relevant size in the brain. In summary, invading astrocytoma cells connect by TMs to one functional cellular network. Disconnection of tumor cells by targeting TMs emerges as a new paradigm to reduce the notorious treatment resistance of this disease.

In preferred embodiments, the glioma to be treated is selected from the group consisting of TM-rich brain tumors, in particular recurring oligodendroglioma, and primary and recurrent astrocytoma WHO II° and WHO III°, and glioblastoma (=astrocytoma WHO ° IV). Further, the subject to be treated is preferably human.

According to a first embodiment, the agent for use according to the present invention is an agent that is capable of mediating RNA interference (RNAi) for the specific knockdown of the growth associated protein 43 (GAP43) gene.

GAP43 has been identified in the present invention as an important factor for the development of TMs and the function thereof. Generally, GAP43 is a factor for the outgrowth of connections between nerve cells during embryonic development, and is down-regulated in the adult central nervous system (CNS). Further, it is connected to cellular calcium homeostasis. Overexpression of GAP43 in neuronal and non-neuronal cells leads to formation of filamentous membrane protrusions. Taken together, GAP43 is a necessary and sufficient factor for the formation of axons and other structures that link cells via membrane tubes such as TMs.

GAP43 is highly expressed in astrocytoma cell lines, where it is enriched at the growth cone-like TM tip. Lentiviral knockdown of the GAP43 gene in primary glioblastoma cells led to a drastic reduction of TM-mediated invasion, proliferation and dissemination. In an in vivo animal model, respective tumors could barely be identified at day 70 post-implantation, whereas control tumors had spread through the entire brain, leading to lethal neurological complications only a few days later. At the same time, GAP43 knockdown animals did not display any clinical deficits. Consequently, GAP43 knockdown in glioblastoma cells resulted in significantly improved survival of mice, when compared to control tumors.

In further studies, GAP43 has been identified as a decisive factor for the TM-mediated formation of the above functional cellular network. Finally, GAP43 knockdown tumors displayed a strong increase in radiation-induced degeneration of tumor cells, resulting in a strong degeneration of the entire tumor cell population six weeks after radiation. In contrast, control tumor cells were highly resistant to radiation and began to regrow as early as six weeks after radiation.

Thus, GAP43 has been identified in the present invention as a mediator of all TM-related functions such as invasion, tumor dissemination, interconnection, stable network formation, and therapy resistance.

Agents that are capable of mediating RNA interference (RNAi) for the specific knockdown of a gene of interest are not particularly limited and are known in the art. They include small inhibitory RNAs (siRNAs), microRNAs (miRNAs), small hairpin RNAs (shRNAs), and antisense oligonucleotides/antisense RNA (asRNA) as known in the art. Briefly, siRNAs are short (usually 20 to 24-bp) double-stranded RNAs (dsRNAs) with phosphorylated 5' ends and hydroxylated 3' ends with two overhanging nucleotides. Physiologically, the Dicer enzyme catalyzes production of siRNAs from long dsRNAs and shRNAs. SiRNAs are incorporated into the RNA-induced silencing complex (RISC) and act by interfering with the expression of specific genes with complementary nucleotide sequences by causing mRNA to be broken down after transcription, resulting in no translation. ShRNAs are RNAs that make a tight hairpin turn and can be cleaved by the enzyme Dicer, resulting in an siRNA that is incorporated into the RISC. MiRNAs are RNA constructs that can be processed intracellularly and are finally also cleaved by Dicer, resulting in an siRNA, and incorporated into the RISC. Finally, as-oligonucleotides/asRNAs are single-stranded oligonucleotides/RNAs that are complementary to a messenger RNA (mRNA) strand transcribed within a cell, and can inhibit translation of a complementary mRNA by base pairing to it and physically obstructing the translation machinery.

Methods for the generation and use of siRNAs, shRNAs, miRNAs, and as-oligonucleotides/asRNAs for the knockdown of a particular gene of interest are not particularly limited and are known in the art. Suitable target sequences for the knockdown of the GAP43 can be easily identified by the person skilled in the art and include the following sequences:

```
CGTGGACACATAACAAGGAAA
(TRCN0000047323-NM_002045.2-212s1c1; SEQ ID NO: 1);

CTGAAGCTAATAAGAAGGA
(TRCN0000047324-NM_002045.2-275s1c1; SEQ ID NO: 2);

TGTAGATGAAACCAAACCTAA
(TRCN0000047325-NM_002045.2-718s1c1; SEQ ID NO: 3);

CCACTAAAGCTTCCACTGATA
(TRCN0000047326-NM_002045.2-513s1c1; SEQ ID NO: 4);
```

-continued
```
TCAAACAGTGTGGCTTAAAC
(TRCN0000421227-NM_002045.3-1302s21c1;
SEQ ID NO: 5).
```

In a particular embodiment, agents that are capable of mediating RNA interference (RNAi) for the specific knockdown of the GAP43 gene are DNA antisense oligonucleotides comprising or consisting of one of the sequences GCACAGCATGATCGTAT (SEQ ID NO: 6), TTTGTTCTTCTCATACAG (SEQ ID NO: 7), and ACAGCATCTGTCTTCTC (SEQ ID NO: 8). In a related embodiment, said agents are asRNAs comprising or consisting of one of the respective sequences GCACAGCAUGAUCGUAU (SEQ ID NO: 9), UUUGUUCUUCUCAUACAG (SEQ ID NO: 10), and ACAGCAUCUGUCUUCUC (SEQ ID NO: 11).

In a further particular embodiment, agents that are capable of mediating RNA interference (RNAi) for the specific knockdown of the GAP43 gene are agents that make use of CRISPR/Cas technology as known in the art. In this context, the gene-editing CRISPR technology is an RNA-guided gene-editing platform that makes use of a bacterially derived protein (Cas9) and a synthetic guide RNA to introduce a double strand break at a specific location within the genome. Editing is achieved by transfecting a cell with the Cas9 protein along with a specially designed guide RNA (gRNA) that directs the cut through hybridization with its matching genomic sequence. By making use of this technology, it is possible to introduce specific genetic alterations in tumor cells, specifically those that knock-out the expression of GAP-43, Ttyh1, and/or Cx43.

In a second embodiment, the agent for use according to the present invention is a compound that is capable of inhibiting the biological activity of GAP43 protein.

Respective compounds can be antibodies, antibody fragments and antibody mimetics specifically binding to GAP43 protein. In this context, antibody fragments include Fab fragments, $F(ab')_2$ fragments, and Fab' fragments. Antibody mimetics include single-chain variable fragments (scFv), single-domain antibodies, affibodies, anticalins, DARPins, monobodies, peptide aptamers, affilins, affimers, and affitins as known in the art. In this context, the term "antibody specifically binding to GAP43 protein" is used synonymously with the term "anti-GAP43 antibody".

Further, respective compounds according to the above second embodiment can be small molecule drugs that are capable of inhibiting the phosphorylation of GAP43 protein, and/or small molecule drugs that are capable of inhibiting the expression of GAP43.

In a third embodiment, the agent for use according to the present invention is a xanthine derivative, preferably propentofylline which is known to down-regulate expression of GAP43.

In a fourth embodiment, the agent for use according to the present invention is a small molecule drug (small molecule inhibitor) that is capable of inhibiting nitric oxide synthase 2 (NOS2). In this context, it is known that down-regulation of NOS2 inhibits GAP43-dependent processes. Small molecule drugs (small molecule inhibitors) that are capable of inhibiting NOS2 are known in the art and include aminoguanidine and 1400W (N-(3-(aminomethyl)benzyl)acetamidine; CAS No: 214358-33-5).

In a fifth embodiment, the agent for use according to the present invention is a small molecule drug (small molecule inhibitor) that is capable of inhibiting transforming growth factor beta (TGF-beta). In this context, it is known that activation of the TGF-beta pathway up-regulates GAP43 expression. Small molecule drugs (small molecule inhibitors) that are capable of inhibiting TGF-beta are known in the art and include SD208 (2-(5-Chloro-2-fluorophenyl)-4-[(4-pyridyl)amino]pteridine; CAS No: 627536-09-8) and LY2109761 (7-(2-Morpholinoethoxy)-4-(2-(pyridin-2-yl)-5,6-dihydro-4H-pyrrolo[1,2-b]pyrazol-3-yl)quinolone; CAS No: 700874-71-1).

In a sixth embodiment, the agent for use according to the present invention is a small molecule drug (small molecule inhibitor) that is capable of inhibiting caspase 3. In this context, it is known that caspase 3 inhibitors down-regulate GAP43 expression. Small molecule drugs (small molecule inhibitors) that are capable of inhibiting caspase 3 are known in the art and include M826 (3-({(2S)-2-[5-tert-butyl-3-{[(4-methyl-1,2,5-oxadiazol-3-yl)methyl]amino}-2-oxopyrazin-1(2H)-yl]butanoyl}amino)-5-[hexyl(methyl)amino]-4-oxopentanoic acid; CAS No: 147-14-8) and z-DEVD-fmk (Z-Asp(OMe)-Glu(OMe)-Val-Asp(OMe)-fluoromethylketone; Methyl (4S)-5-[[(2S)-1-[[(3S)-5-fluoro-1-methoxy-1,4-dioxopentan-3-yl]amino]-3-methyl-1-oxobutan-2-yl]amino]-4-[[(2S)-4-methoxy-4-oxo-2-(phenylmethoxycarbonyl-amino)butanoyl]amino]-5-oxopentanoate; CAS No: 210344-95-9).

In a seventh embodiment, the agent for use according to the present invention is a compound that is capable of blocking the N-methyl-D-aspartate (NMDA) receptor. In this context, it is known that inhibition of NMDA prevents induction of GAP43. Compounds that are capable of blocking the NMDA receptor are known in the art and include amantadine, MK801 (Dizocilpine; [5R,10S]-[+]-5-methyl-10,11-dihydro-5H-dibenzo[a,d]cyclohepten-5,10-imine; CAS No:77086-21-6), and pentobarbital.

In an eighth embodiment, the agent for use according to the present invention is an agent that is capable of mediating RNAi for the specific knockdown of the human tweety homologue 1 (Ttyh1) gene.

Ttyh1 has been identified in the present invention as an important factor for the development of TMs and the function thereof. Generally, Ttyh1 is specifically expressed in the brain, required for neuritogenesis and early brain development, and is (like GAP43) down-regulated in the adult central nervous system (CNS). Further, it is connected to cellular calcium homeostasis. It has been also shown to be expressed in astrocytes, with increased expression after injury/activation.

Ttyh1 is enriched along the membrane of TMs of invading astrocytoma cells. Lentiviral knockdown of the Ttyh1 gene in primary glioblastoma cells led to a drastic reduction of TM-mediated invasion, proliferation and dissemination. In an in vivo animal model, respective tumors could no longer be identified by MRI at day 70 post-implantation, whereas control tumors had spread through the entire brain with large and space-occupying lesions seen in MRI, leading to lethal neurological complications only a few days later. At the same time, Ttyh1 knockdown animals did not display any clinical deficits.

Thus, Ttyh1 has been identified in the present invention as mediator of TM-dependent invasion and dissemination.

Agents that are capable of mediating RNA interference (RNAi) and agents for use in CRISPR/Cas technology according to the eighth embodiment of the present invention are as defined above for the first embodiment of the present invention. The same applies to methods for the generation and use of respective agents.

Suitable target sequences for the knockdown of the Ttyh1 gene are can be identified by the person skilled in the art and include the following sequences, wherein SEQ ID NOs: 12 and 16 are particularly preferred:

```
                         (ORF 880-900; SEQ ID NO: 12)
     TCAGACATCCTGAGCTATTAT;

(ORF 1047-1067; SEQ ID NO: 13)
     CTTGGAGGAGACTCTGAATGT;

(ORF 825-845; SEQ ID NO: 14)
     CTCCAATCCAGACCCTTATGT;

(ORF 319-339; SEQ ID NO: 15)
     ATCGGTTTCTATGGCAACAGT;
     and (3'UTR 91-111; SEQ ID NO: 16)
     GCTCTGACCACTAACACTCTT.
```

In a ninth embodiment, the agent for use according to the present invention is a compound that is capable of inhibiting the biological activity of TTYH-1 protein.

Respective compounds can be antibodies, antibody fragments and antibody mimetics specifically binding to TTYH-1 protein. In this context, antibody fragments and antibody mimetics are as defined above for the second embodiment of the present invention. Further, the term "antibody specifically binding to TTYH-1 protein" is used synonymously with the term "anti-TTYH-1 antibody".

In a tenth embodiment, the agent for use according to the present invention is an agent that is capable of mediating RNA interference (RNAi) for the specific knockdown of the connexin 43 (Cx43) gene. Connexin 43 (Cx43) is the most important gap junction protein for TM-mediated functionality. Cx43 gap junctions are regularly found at the contact points of TMs: they are obligatory channels necessary for the function of the TM-mediated tumor cell network in primary brain tumors, thus driving their progression and therapy resistance. Specifically, Cx43 gap junctions are necessary for the exchange of molecules between tumor cells via TMs, and are necessary for cell-cell-communications in the glioma via intercellular calcium waves (ICWs). Of 22 known gap junction proteins, Cx43 is the only one that is differentially regulated in 1p/19q codeleted versus intact human gliomas, making it a prime candidate for mediation of treatment resistance. Consequently, shRNA knockdown of Cx43 led to a decrease in glioma growth, and prolongation of survival of brain tumor-bearing mice.

Respective agents are as defined above for the first embodiment of the present invention, including agents for use in CRISPR/Cas technology. The same applies to methods for the generation and use of respective agents. A suitable target sequences for the knockdown of the Cx43 gene is the sequence GCCCAAACTGATGGTGTCAAT (SEQ ID NO: 20).

In an eleventh embodiment, the agent for use according to the present invention is a compound that is capable of blocking gap junctions, in particular that is capable of inhibiting the biological activity of Cx43.

Respective compounds can be antibodies, antibody fragments and antibody mimetics specifically binding to and/or functionally blocking Cx43. In this context, antibody fragments and antibody mimetics are as defined above for the second embodiment of the present invention. Further, the term "antibody specifically binding to Cx43" is used synonymously with the term "anti-Cx43 antibody".

Further, respective compounds can be gap junction blocking peptides such as peptides Gap 26 (VCYDKSFPISHVR; SEQ ID NO: 17) and Gap 27 (SRPTEKTIFII; SEQ ID NO: 18).

Furthermore, compounds according to the above eleventh embodiment of the present invention are preferably selected from the group consisting of glycyrrhetinic acid and derivatives thereof, in particular carbenoxolone; quinine and derivatives thereof, in particular quinidine and mefloquine; anandamide; octanol; heptanol; anthranilic acid and derivatives thereof, in particular fenamic acid and derivatives thereof such as meclofenamic acid; anesthetics, in particular isoflurane and ketamine; retinoic acid; tonabersat.

In a preferred embodiment, treatment of glioma in a subject according to the present invention comprises in addition to the use of the agents of the present invention an additional tumor therapy, in particular chemotherapy and/or radiotherapy.

In a second aspect, the present invention relates to a method for the treatment of glioma in a subject, comprising the step of administering an agent, selected from the group consisting of
(a) an agent that is capable of mediating RNA interference (RNAi) for the specific knockdown of the growth associated protein 43 (GAP43) gene,
(b) a compound that is capable of inhibiting the biological activity of GAP43 protein,
(c) a xanthine derivative,
(d) a small molecule inhibitor of nitric oxide synthase 2 (NOS2),
(e) a small molecule inhibitor of transforming growth factor beta (TGF-beta),
(f) a small molecule inhibitor of caspase 3,
(g) a compound that is capable of blocking the N-methyl-D-aspartate (NMDA) receptor,
(h) an agent that is capable of mediating RNAi for the specific knockdown of the human tweety homologue 1 (Ttyh1) gene,
(i) a compound that is capable of inhibiting the biological activity of TTYH-1 protein,
(j) an agent that is capable of mediating RNA interference (RNAi) for the specific knockdown of the connexin 43 (Cx43) gene,
(k) a compound that is capable of blocking gap junctions, in particular that is capable of inhibiting the biological activity of connexin 43 (Cx43), to a subject in need thereof.

According to this second aspect of the present invention, all relevant definitions and embodiments as defined for the first aspect of the present invention apply in an analogous manner. In particular, the glioma, the subject, and the compounds/agents according to subordinate points (a) to (k) are as defined above.

In a third aspect, the present invention relates to a method for assessing the malignancy of glioma in a subject, comprising the steps of (i) determining the number and/or length of tumor microtubes (TMs) of a given tumor, and/or (ii) determining the amount of connexin 43 (Cx43) and/or GAP-43 and/or Ttyh1 expression in a given tumor, wherein a higher number and/or a greater length of TMS, and/or a higher amount of Cx43 and/or GAP-43 and/or Ttyh1 expression as compared to a control sample correlates with higher malignancy of said tumor, including its resistance to radiotherapy.

Figure 5:
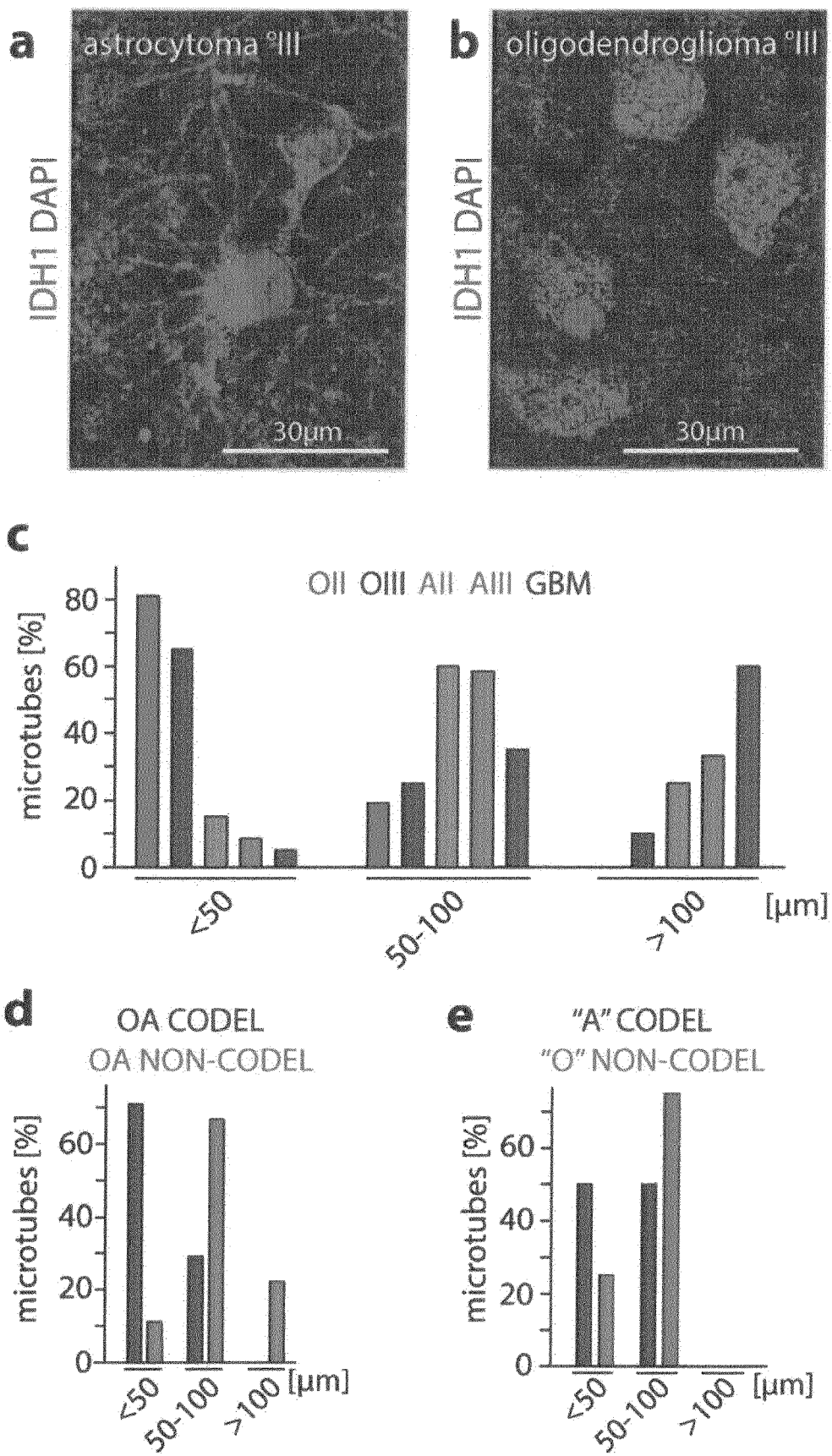

Respective methods for determining the number and/or length of tumor microtubes (TMs) of a given tumor, and/or determining the amount of connexin 43 (Cx43) and/or GAP-43 and/or Ttyh1 expression in a given tumor are not particularly limited and are known in the art. In particular, methods for determining the number and/or length of tumor microtubes (TMs) of a given tumor have been established by the present inventors, and require a tumor-cell specific immunohistological staining. One example is immunohistochemical staining of the IDH1-R132H mutation (present in >70% of WHO II° and WHO III° gliomas) in human astrocytomas (cf. FIG. 5).

The present invention provides for the first time therapeutic approaches for the treatment of glioma, in particular astrocytoma and glioblastoma, that are characterized by reduction of the tumor's therapy resistance, high efficiency, low morbidity and mortality, prolonged survival and low therapy-related toxicity.

The figures show:

FIG. 1:

Distinct Membrane Microtubes Contribute to Brain Tumor Dissemination, and Connect Single Tumor Cells.

a, In vivo MPLSM of S24 GBMSCs growing in the mouse brain over 60 days (D). Arrows: thin cellular protrusions extending into the normal brain at the tumor border, arrowheads: long intratumoral protrusions. Maximum intensity projections (MIPs), 300-357 μm depth. b, Number and length of protrusions at the same time points (S24 tumors; n=77-120 cells in n=3 mice). c, Travel of two nuclei (arrows, arrowheads) after nuclear division (at start, and at 103 hours) along cellular protrusions of S24 GBMSCs. Speed of travelling nuclei: 66,42±36,25 μm/day, n=16 nuclei in n=6 mice. 3D images, z-dimension 63 μm. d, Protrusions are actin-rich, and arborize (S24 Lifeact-YFP, MIP, z-dimension 15 μm). e, 3D reconstruction of membrane microtubes in a T325 astrocytoma over 3 days (in vivo MPLSM). Arrowheads: stable main tube; arrows: dynamic side tubes. f, Scanning electron microscopy (SEM) images of a S24 GBMSC membrane microtube (arrow, identified by GFP photooxidation) in the mouse brain parenchyma, containing a mitochondrium and microvesicles. Asterisks: axons. g, 3D rendering of membrane tubes interconnecting single S24 GBMSCs to a dense multicellular network in an exemplary brain volume of 238×192×90 μm. Intercellular (connecting) and non-connecting tubes, and connected and unconnected tumor cells are shown color-coded. Tubes were also classified as connecting when the connected cell was outside this volume. h, Number of membrane tubes per S24 tumor cell that connect this cell to another tumor cell in the same microregion over time (n=141-437 cells in n=3 mice). Error bars show standard deviations.

FIG. 2:

Different Primary Glioblastoma Cell Lines (GBMSCs) Growing to Astrocytic Tumors in the Mouse Brain.

a-f: In vivo microscopy (3D) of 6 different GBMSC lines reveals abundant formation of ultra-long membrane protrusions in the mouse brain: a T1, b T269, c T325, d S24, e WJ, and f P3 (z-dimensions from 200-500 μm depth). Insets show the boxed areas in the corresponding images in higher magnification, covering a proportion of the z-dimension. Per cell line, two time points are shown, adapted to their growth speed in vivo (T269, P3 fast; T1, S24 intermediate, T325 and WJ slow). g, 3D image of a S24 astrocytoma (injection of a 50:50 mixture of either GFP- or RFP-positive cells), revealing multiple ultra-long and very thin membrane protrusions (arrows) in the live mouse brain. Note that membrane tubes partly run in parallel. h, CGH-profile of the S24 GBMSC line demonstrating chromosomal alterations typical for GBM (chromosome 7 gain, 10 loss). i, Chromosome 7 FISH analysis of one S24 GBMSC in the main tumor area demonstrates polyploidy: 90% of n=100 analyzed cells in the main tumor area were clearly polyploid for Chromosome 7, indicating that implanted S24 GBMSCs give rise to tumors genetically identifiable as glioblastomas. j, Whole mouse brain coronar sections at day 171 after S24 injection showing two main features of glioblastoma growth: diffuse brain invasion in a typical dissemination pattern (left image), and a solid, angiogenic core identified by hemorrhagic changes of the main tumor area (right brightfield image). k, Increasing angiogenesis in this tumor is further demonstrated by dynamic in vivo MPLSM. l, Actin-rich S24 GBMSC tip, invading into the brain (single plane images; schematic drawing below). In vivo MPLSM: a-g; k,l.

FIG. 3:

Characterization of Membrane Microtubes in Astrocytoma Mouse Models.

a, Confocal immunohistochemistries (maximum intensity projections) of human nestin (green, allows specific detection of S24 GBMSC-related structures in the mouse brain), and different other cellular and molecular factors (red, co-stainings). The degree of expression of the different factor in tumor cell-derived membrane tubes is indicated in the right lane: −=no signal in membrane tubes, (−)=only weak signal in a small subset of membrane tubes, (+)=positive signal in some membrane tubes, +=positive signal in all membrane tubes. b, In vivo images of S24 GBMSCs genetically expressing green fluorescent protein (GFP, green) linked to different cellular/molecular components. c, Example of a very stable T325 GBMSC membrane microtube (arrowheads), followed over 126 days in vivo; MIP, z-dimension 48 µm. d, SEM image of two photoconverted membrane microtubes (arrows) and a nucleus of a non-photoconverted brain cell (N). e, 3D reconstruction of serial SEM-images (22,29 µm (xy)*4,62 µm (z)=102,9 µm$^3$) illustrate the membrane contours. f, Maximum speed of mitochondria in S24 membrane tubes vs. tumor cell soma in vivo (n=10 per group, t-test, red lines show means). g, 3D reconstruction of serial SEM sections of the membrane microtube (red) and the two axons (green), which are shown in FIG. 1f. h, in vivo MPLSM 3D image of the genetic Tlx mouse glioma model, with abundant membrane microtubes connecting single stem-like astrocytoma cells (z-dimension 83 µm). $*p<0.05$.

FIG. 4:

Origin of TM-Connections Between Astrocytoma Cells, and Long-Time Dynamics of TM-Extending Cells.

a, Graphs illustrating two theoretically possible ways of intercellular connections by membrane tubes in a model of two tumor cell populations marked with 2 different fluorescent proteins: (1) tumor cells remain connected after cell division with their ancestors. In this case, only connections between cells of the same color are expected [GFP-GFP (green) or RFP-RFP (red)]; (2) tumor cells only connect to unrelated glioma cells. Here, 50% of connections would be between cells of different color [GFP-RFP or RFP-GFP (grey)], and 25% of the same color [GFP-GFP (green) and RFP-RFP (red)], respectively. b, Quantification of the real dataset, where a 1:1 mixture of either GFP or RFP expressing S24 GBMSCs (S24GFP/S24RFP) was co-injected into the mouse brain, revealing that both potential mechanisms are in place (n=164 connections in n=3 mice). c, 3D image (70 days after injection) of a co-implantation of GFP- and RFP-expressing S24 GBMSCs. Quantification revealed that both large fluorophores (which cannot pass gap junctions) did never colocalize in cell somata or in TMs (n=>2500 astrocytoma cells analyzed). d, e, Examples of 3D images of membrane tube connections between individual, non-related astrocytoma cells that differently express GFP or RFP (arrows in d and e). f, Example of a 3D image of same-color connections between two RFP-positive cells (arrows). g, SEM image of a S24 spheroid, left panel: yellow color marks cell bodies, arrowheads point to membrane microtubes; right panel: high magnification of tubes with direct membrane contact (arrow). h, 3D images of a perivascular T325 astrocytoma cell (arrows), which first utilizes a TM to explore the perivascular niche (D45-D73) until it moves to the explored region, and remains in a strict perivascular position until day 255. A second cell (arrowhead) is quiescent until D129 and is embedded into a vascular loop formation, which persists after disappearance of the main cell soma. i, MIP of a TM-containing S24 GFP astrocytoma cell which enters a perivascular position over time (arrow), and another one which remains in its non-vascular (parenchymal) position over 105 days (arrowhead). All images were acquired by in vivo MPLSM, 50-650 µm deep in the brain.

FIG. 5:

Tumor Microtubes (TMs) are Characteristic for 1p/19g Non-Codeleted Human Gliomas.

a,b, Representative IDH1 R132H immunofluorescence images of an 1p/19q non-codeleted astrocytoma (a), and 1p/19g codeleted oligodendroglioma (b). c, Proportion of patient gliomas with a maximum length of IDH1 R132H—positive microtubular structures in standard 3 µm thin sections. Oligodendroglioma (O, 1p/19q codeleted) grade II, III; and astrocytoma (A, 1p/19q non-codeleted) grade II, III, and IV (glioblastoma, GBM); n=20-24 patients per tumor entity, n=105 total. d, Maximum microtube length of oligoastrocytomas with 1p/19q codeletion (OA CODEL; n=31 patients) and without (OA NON-CODEL; n=9 patients). e, Maximum microtube length of tumors morphologically classified as astrocytomas but with 1p/19q codeletion ("A" CODEL; n=6 patients), and tumors morphologically classified as oligodendrogliomas but without 1p/19q codeletion ("O" NON-CODEL; n=9 patients).

FIG. 6:

1p/19q Codeleted Gliomas do not Show Relevant TMs, While Non-Codeleted Ones Show TMs Even in the Contralateral Hemisphere in Patients.

a, 3D image of a BT088 oligodendroglioma xenograft tumor growing in the mouse brain, inset shows the boxed area in a higher magnification. Cells are roundish, TMs are scarce. b, Quantification of TM lengths of BT088 oligodendroglioma cells (left), and S24 astrocytoma cells (right), at day 60 after tumor implantation. n=3 animals per entity. c, IDH1 R132H immunohistochemistry of the contralateral brain hemisphere (macroscopically tumor-free) of a patient deceased from a WHO ° III astrocytoma. d, Exemplary IDH1 immunohistochemistries of gliomas morphologically classified as oligoastrocytomas, with (left) or without (right) 1p/19q codeletion.

FIG. 7:

TM-Connections Allow Communication in Multicellular Networks.

a, Representative time-lapse image of calcium waves (Rho2-AM) travelling along TMs of GBMSCs (bidirectional; arrows). Red arrows: crossing of two TMs, with simultaneous calcium peak. Right: 3D image of the GBMSC GFP signal of this region, and 3D rendering of the calcium-wave participating structures (green). Asterisk and dot mark two individual cells. b, Frequency and synchronicity (see Methods section) of calcium peaks in GBMSCs, shown for TM-connected vs. non-TM-connected tumor cells (n=40 vs. 43 cells in n=3 mice/cond.; t-tests). c, right: Calcium transients ($\Delta F/F0$, Rhod-2AM) of non-connected GMBSCs (grey) vs. TM-connected cells (blue); broken lines mark synchronous calcium transients; left: MIP (10 slices) of the corresponding region (red cells: astrocytes; green cells:

tumor cells without Rhod-2AM signal; yellow cells: tumor cells with Rhod-2AM signal). d, Representative heat map of calcium transients between GBMSCs. e, Frequency and synchronicity of calcium peaks recorded during brain superfusion with extracellular saline (ES-control) vs. 100 µM carbenoxolone (CBX) in GBMSCs (blue box) and normal brain astrocytes (red box); n=3 mice per group; t-tests. f, SR101 uptake in a non-TM-connected GBMSC (upper image) and a TM-connected one (lower image). Right, corresponding quantification (AU, arbitrary units); n=55 cells in n=3 mice/condition; Mann-Whitney test. g, 3D images (z-dimension 180 µm) of SR101 microinjected tumors, without (control, upper image) and with co-injected CBX (lower image; area of injection: circles) 120 min. after injection. Red cells: normal brain astrocytes. Graph: corresponding quantification of SR101-fluorescence (n=4962-5676 cells in n=3 mice per group; Mann-Whitney test). Images a,c,f and g are acquired by in vivo MPLSM. GBMSCs: S24 line. Error bars show standard deviations. *$p<0.05$, ***$p<0.001$.

FIG. 8:

Intercellular Communication Via Gap Junctions in TM-Connected Astrocytoma Cells.

a, Example of a calcium wave involving TMs of GBMSCs in a tumor region; measurement by the genetically-encoded sensor Twitch-3 that allows ratiometric calcium measurements via FRET. Shown is an overlay of cpVenusCD and CFP channels. Yellow color reflects low, red color high calcium concentrations. Right: ratios of single sections of one TM illustrating the propagation of a calcium wave along the TM. b, Exemplary heat map of intercellular calcium wave (ICW) communications between T325 astrocytoma cells transfected with the genetically-encoded calcium sensor GCaMP3. c, Exemplary heat map (small molecule calcium indicator Fluo-4 AM). d, Analysis of baseline-normalized synchronicity (see Methods for details) of calcium signals between S24 GBMSC glioma cells vs. normal brain astrocytes. Inositol triphosphate (IP3) was blocked by 2-APB, cellular ATP receptors by the nonselective purinergic 2 receptor antagonist suramine, and gap junctions were blocked by CBX (glioma cells: t-tests, astrocytes: Mann-Whitney tests). ES, extracellular saline used as control. e, 3D images of a non-TM-connected S24 tumor cell (S24tdtomato), loaded with the gap-junction permeable dye lucifer yellow via electroporation. f, 3D images of TM-connected S24 tumor cells (S24tdtomato) after dye transfer into one of the TM-connected cells. g, Quantification of lucifer yellow fluorescence intensity in the neighboring cells next to the electroporated cell (n=4 sections from n=2 mice; n=64 TM-connected vs. n=42 non-TM connected cells quantified; t-test). h, Western Blot analysis of Cx43 protein expression in 4 GBMSC and 2 oligodendroglioma cell lines. i, Immunohistochemistry demonstrating the localization of different connexins in S24 GBMSCs; no clear TM-related expression, and/or localization at TM crossings could be observed. a-d, acquired by in vivo MPLSM. e,f,i: confocal microscopy images. *$p<0.05$, ***$p<0.001$.

FIG. 9:

Connexin 43 Gap Junctions Connect TMs in Astrocytomas.

a, Quantification of Cx43 protein expression detected by immunohistochemistry in 1p/19 codeleted vs. non-codeleted human gliomas (n=8 each, t-test). b, Nestin and Cx43 double-immunofluorescence in S24 and T1 GBMSC tumors (arrows point to Cx43-positive TM-interconnections, arrowheads to Cx43-positive TMs). c, SEM image of a direct membrane contact of 2 TMs in the mouse brain (identified by photooxidation). d, Synchronicity of calcium peaks in S24 shControl vs. shCx43 cells (n=3 mice/condition; Mann-Whitney test). e, Proportion of TM-devoid (0 TMs) vs. TM-rich (>4 TMs) cells in these tumors 20 and 40 days after tumor implantation (n=3 mice per group, ANOVA, Tukey's post-hoc test). f, High-field T2 MRI images of shControl vs. shCx43 tumors, 72 days after tumor implantation. Quantifications of n=6 animals per group (t-test). g, Kaplan-Meier survival plot of these groups (log rank test). Error bars show standard deviations. *$p<0.05$; ***$p<0.001$.

FIG. 10:

TM-Connected Astrocytoma Cell Networks Can Repair Themselves, and Resist Radiotherapy.

a, Time series of exemplary 3D images (54 µm thickness) of a tumor region after laser-induced killing of a GMBSC (circle). Over time a TM (arrowheads) is extended, and a nucleus (star) translocates via that TM to the very place the killed cell has been located at before. b, 3D images (51 µm thickness) of a brain tumor region directly before photodamage to a larger area (dotted boxes), and 2 days afterwards. Right image: single plane of the damaged region. c, Time course of a region next to a larger photodamage (dotted area), arrows: GBMSC TMs extending into the photodamaged region. MIP of 21 µm, n=3 mice. d, Examples of GBMSC tumor microregions (3D images, 20 µm depth) before start of radiation (d0), and 7 days later (d7). Stars: non-TM-connected GBMSCs; arrow: one exemplary cell with many TMs. Graph: Relative change of cellular subtypes under sham radiation (Sham) or radiation (Rad) (n=3 mice per group, t-tests). e, Number of TMs per cell in these tumors (3D images left side, n=50 cells/time point in n=3 mice per group, Mann-Whitney test). f, Exemplary heat maps of calcium transients (Rhod-2AM) of a sham treated (left) and radiated GBMSC tumor region (right). g, Synchronicity of calcium transients after sham treatment or radiotherapy in individual GBMSC tumor regions (Fluo-4AM, n=3 mice per group, Mann-Whitney test). h, Relative changes of all cells (left) and subgroups of TM-connected vs. non-connected GBMSCs of shControl vs. shCx43 tumors after sham/ radiotherapy (n=3 mice per group, t-tests). All images are acquired by in vivo MPLSM. GBMSCs: S24 line. Error bars show standard deviations. *$p<0.05$, "$p<0.01$, ***$p<0.001$

FIG. 11:

Effects of Radiotherapy on Cellular Morphology, Long-Term Survival, and Calcium Homeostasis in Astrocytomas.

a, 5 days after initiation of radiotherapy (3×7 Gy), nuclear fragmentation characteristic for apoptosis (arrow) can be detected in a proportion of cells at this time point. Green, nuclear staining by H2B-GFP transduction; red, S24 cell cytoplasm. b, Representative 42 day time course of a distinct tumor microregion, followed after start of radiotherapy (day 0). TM-connected cells (two examples are marked with black stars) show long-term survival; note that surviving cells show an increase in the number of their TMs. n=3 mice per group. All images were acquired by in vivo MPLSM, 50-650 µm deep in the brain. c-f, Ratiometric measurements of basal calcium levels. c, Mean ratios of fluorescence intensities of the FRET partners cpVenusCD and CFP, before, and after two days of radiation (2×7Gy) in TM-connected cells (n=3 mice per group; Mann-Whitney test). d, Fluorescence intensities (normalized by the mean intensities of the corresponding datasets) in TM-connected cells for the two FRET partners illustrated by a scatter blot (black dots represent analyzed cells at the day before radiotherapy, red dots 2 days after initiation of radiotherapy); linear regression revealed similar correlation strengths at the two time points (n=3 mice), reflecting very homogenous calcium levels in the astrocytoma cells before and after radiotherapy. e, Mean ratios of fluorescence intensities of the FRET partners before and after two days of radiation (2×7Gy) in non-connected cells, n=3 mice; Mann-Whitney test. f, Normalized fluorescence intensities in non-connected cells for the two FRET partners. Here, linear regression revealed highly homogeneous basal calcium levels only before radiotherapy, while during radiotherapy the linear correlation was lost, illustrating heterogeneous calcium levels in the analyzed cells. (n=3 mice per group). GBMSCs, S24 cell line.

FIG. 12:

In Silico Analysis of 1p/19q Codeleted vs. Non-Codeleted Gliomas.

Biological function analysis was performed using Ingenuity Pathway Analysis. a, Barplot of the top differentially regulated downstream biological functions. b, Heat map of downstream biological functions. The map is color coded: more intense orange means more activation in 1p/19q non-codeleted tumors (compared to codeleted tumors), blue the other way round. Note the activation of "Cellular movement" and "Cell-to-cell signaling" in non-codeleted tumors. c, Results of the analysis of canonical pathways in 1p/19q non-codeleted vs. codeleted gliomas. Higher positive z-Score: upregulated in 1p/19q non-codeleted vs. codeleted gliomas; Higher negative z-Score: upregulated in 1p/19q codeleted gliomas vs. non-codeleted gliomas.

FIG. 13:

Proficiency for GAP-43 Expression in 1p/19q Non-Codeleted Ggliomas; and Schematic Illustration of the Role of TMs in Brain Tumor Progression.

a, TrkA, TrkB, NGF and NT-4 protein expression detected by immunohistochemistry in 1p/19 codeleted vs. non-codeleted human gliomas (n=8 each, t-tests). b, Western Blot analysis of GAP-43 protein expression in 4 GBMSCs cultured under non-adherent neurosphere (NSM) vs. differentiating, serum-containing adherent condition. c, Spheroid invasion assay from S24 shControl vs. shGAP-43 cells in a gel matrix, and the corresponding quantification (t-test). d, Western Blot analysis of Cx26, C31, Cx37, and Cx43 protein expression in shGAP-43 GBMSCs vs. shControls. Of note, the GAP-43 knockdown leads to a Cx43 protein reduction of 89%, while expression of the other connexins was not reduced. e, Overexpression of GAP-43 in BT088 oligodendroglioma cells results in protein levels similar to that in GBMSCs. f, Anatomical and molecular mechanisms of TM-driven tumor dissemination and network function in astrocytomas. MV, microvesicles; mito, mitochondrium; ER, endoplasmatic reticulum (identified by PDI positivity); MT, microtubules. *p<0.05, p<0.01, *p<0.001.

FIG. 14:

GAP-43 is Required for TM Outgrowth and Function.

a, GAP-43 protein expression detected by immunohistochemistry in 1p/19 codeleted human astrocytomas vs. non-codeleted oligodendrogliomas (n=8 each), and corresponding quantification (Mann-Whitney test). b, GAP-43 Western blot of different glioma cell lines. c, Immunocytological images of GAP-43 protein, with preferential GAP-43 localization at the nestin-negative tip of TMs (arrows) in different GBMSC lines. d, 3D images of glioma cells (left, inverted) and quantification of TM side branches 20 days after implantation (n=60 cells in n=5/6 mice, t-test). e, Tile scan single plane images of control (upper image) and shGAP-knockdown GBMSC S24 tumors (lower image); right: corresponding quantification (n=3 mice/condition; Mann-Whitney tests). f, In vivo tumor cell invasion distance within 24 hours (n=3 mice, Mann-Whitney test). g, In vivo proliferation of S24 GBMSCs (volume of 0.037 mm$^3$; n=4 mice, Mann-Whitney tests). h, Fraction of TM-connected cells at day 20 in S24 tumors (n=164 cells in n=6 mice, t-test). i, Synchronicity analysis of calcium peaks in S24 shControl vs. shGAP-43 cells in vivo (n=3 mice; Mann-Whitney test). j, T2 MRI images of S24 shControl vs. shGAP-43 tumors, 72d after tumor implantation. Quantifications of n=6 animals per group (t-test). k, Kaplan-Meier survival plot of these groups (log rank test). l, time course after irradiation with 3x7 Gy in S24 shControl vs. shGAP-43 astrocytoma cells, corresponding quantifications (n=3 mice/group; t-tests). m, MRI images of S24 shControl vs. shGAP-43 tumors, 60 days after radiation (115 days after tumor implantation); right: quantifications of 5-6 animals per group (t-test). n, Exemplary brain sections of Nestin IHCs of these mice; regions with highest tumor cell densities (boxes) were quantified for proliferation index (Ki-67-positive cells/all cells; n=3 animals; t-test). o-q, GAP-43 overexpression in BT088 oligodendroglioma cells leads to an increase in TM numbers (o, left: inverted 3D images and quantifications, n=80 cells in n=3 mice/group), more TM branches (p, n=40 cells in n=3 mice/group), and a higher invasion capacity (q, n=75 cells in n=3 mice/group; red lines show means; t-tests) 14 days after injection. r, relative change of tumor volumes 21 days after radiotherapy in BT088 vector-control vs. GAP-43 overexpression tumors (n=3 mice/group; t-test). in vivo MPLSM: images d,e,l and o, and quantifications d-i, l, m, o-r. Error bars show standard deviations. *p<0.05, p<0.01, *p<0.001.

FIG. 15:

a, S24 shControl GBMSCs show regular thin and regularly branched TMs in vivo, whereas S24 shTTYH1 cells develop aberrant TMs. Note the abnormal morphology of TMs, which are short, show reduced branchings, and frequent beadings. b, Distance of individual tumor cells from the main tumor (tumor core was defined as 500 μm), measured after growth in vivo on day 20 (n=3 mice per group). Mean numbers of invaded tumor cells are shown for each range. In contrast to S24 shControl tumors, S24 shTTYH1 tumors are less infiltrative, and just very few cells were detectable beyond the tumor core. [Range <500 μm: 395 vs. 19.5 cells [Median] (p=0,004; Mann-Whitney U-test), range 500-1000 μm 260 vs. 1,5 cells (P=0,004; Mann-Whitney U-test) and range >1000 μm: 138 vs. 0 cells (p=0,004; Mann-Whitney U-test).] c, The tumor area/brain area ratio was measured on day 75 on 9.4 tesla MRI scans (n=6 animals per group). On average 62.90% of the brain area was visibly infiltrated by S24 shControl tumor cells whereas just 5.82% of the whole brain area was visibly infiltrated by S24 shTTYH1 cells (p=<0,001; Two-tailed t-test). d, Kaplan-Meier Survival Analysis was performed with 6 animals per group. The mean survival time of animals of the S24 shControl group was 74.67 days compared to 176.17 days in the S24 shTTYH1 group (P=<0,001; Log Rank Test).

FIG. 16:

New Molecular Candidates for TM Formation (A, B) Glioma growing in the live mouse brain after implantation of S24 GBMSCs cultured under stem-like spheroid conditions (A), and serum-containing, adherent conditions (B) (z=180 μm; representative images 12 days after implantation). (C) Distance of invaded tumor cells from the surface of the main tumor 14 days after implantation of S24 cells cultured under serum-containing-(adherent-) versus serum-free-(GBMSC-) conditions (20-115 cells in n=3 mice per group; Mann-Whitney test). (D) Quantification of TM-length of S24 tumor cells cultured under adherent-versus GBMSC-conditions 14 days after implantation (20-52 TMs in n=3 mice per group; Mann-Whitney test). (E) Representative image of S24 glioma on day 104, when GBMSCs were cultured under stem-like conditions before (z=165 µm). (F) Representative image of S24 glioma on day 101, when GBMSCs were cultured under serum-containing conditions before (z=165 µm). (G) Ingenuity pathway analysis of microarray data from the comparison of GBMSCs cultivated under stem-like spheroid conditions vs. serum-containing, adherent conditions showing the 10 most activated categories (for in-depth data, see FIG. 17). A high positive activation z score indicates an upregulation under stem-like conditions. A-F: data obtained by in vivo MPLSM, A, B, E, F: 3D images.

FIG. 17:

(A) Heat map of biological functions from Ingenuity Pathway Analysis (IPA) comparing the expression in GBMSCs cultured under stem-like vs. serum-containing adherent conditions (RNA microarray data). (B) IPA heat map of the Cellular Movement category. The heat maps are color coded: more intense orange indicates upregulation under stem-like conditions. Categories are sized by log(p-value).

FIG. 18:

(A) Western blot analysis of TTYH1 and VGF protein expression levels of S24 and T1 GBMSCs cultured under serum-free, non-adherent conditions and serum-containing, adherent conditions for 7 days, demonstrating a downregulation on the protein level under adherent conditions. (B) Maximum intensity projection images of immunohistochemical stainings of human nestin (green) and VGF (red) acquired by confocal microscopy (S24 GBMSC tumors); arrowheads: VGF-positive TMs. (C) Verification of shRNA knockdown of VGF in S24 GBMSC by western blot analysis (95% reduction in protein level). (D) In vivo 3D MPLSM images of S24 shControl and shVGF GBMSCs on day 40 (z=45 µm) demonstrating no obvious phenotypical aberration and no apparent difference in tumor invasion and growth; GBMSCs (green) and blood vessels (blue).

FIG. 19:

TTYH1 Protein Locates at Distinct Parts of Glioma Cells and their TMs (A) Maximum intensity projection images (MIPs) of immunocytochemical stainings of TTYH1 (red) in S24 GFP cells (green) revealing a preferential localization of TTYH1 protein along the protrusion membrane and at the growth cone-like tip of these TM-like structures (arrowheads; higher magnification of a tip is shown in the lower panel). (B, C) MIPs of immunohistochemical double-stainings of human nestin (green), which specifically labels GBMSCs and their TMs, and TTYH1 (red) in S24 GBMSC tumors. (B) demonstrates a tumor cell (cell body: asterisk) and its TTYH1-positive TM (arrowheads) within many TTYH1-negative TMs; (C) shows a tumor cell (cell body: asterisk) with both TTYH1-positive (arrowheads) and negative (arrows) TMs. (D) Immunohistochemical staining of IDH1 (unequivocal identification of tumor cells with IDH1 R132H-mutation specific antibody) and TTYH1 of a human astrocytoma specimen also demonstrates a TTYH1-positive glioma cell and its TM (arrowhead) in human brain tumors. (E) 3D image of animmunocytochemical staining of Integrin-α5 (ITGA5; green) and TTYH1 (red) in S24 cells (arrow: ITGA5 enrichment at the growth cone-like tip; arrowhead: co-localization of ITGA5 and TTYH1 at the tip of the TM). A-E: Confocal microscopy.

FIG. 20:

TTYH1 Drives Glioma Cell Invasion (A) Western blot analysis of TTYH1 protein levels in different glioma cell lines. (B) Left side: Linear regression revealed a correlation between mean TTYH1 protein level assessed with western blot analysis and diffuse infiltration capacity of three different glioma cell lines in vivo. The invasion coefficient was defined as mean cell number further than 1500 µm from the center of tumor bulk in relation to the tumor bulk area to describe the degree of diffuse infiltration capacity of each GBMSC line (n=3 mice per cell line). Right side: Representative in vivo 3D MPLSM images of S24, T269 and T325 tumors demonstrating the different degrees of diffuse infiltration on day 39 (+/−5 days). (C) Spheroid invasion assay from S24 shControl versus shTTYH1 cells in a collagen matrix 48 hours after seeding. The surface borders of the spheroids directly after seeding are marked as white lines (n=3 spheroids per group; Mann-Whitney test). (D, E) Time series of 3D images of S24 shControl GBMSCs (z=36 µm) (D) and S24 shTTYH1 GBMSCs (z=69 µm) (E) reveal the impaired invasion capacity induced by TTYH1 knockdown. Arrows in the left panel indicate the subsequent invasion route; arrowheads label the cell bodies of the invading GBMSCs (green), blood vessels (red). (F) Measurements of the invasion speed of single S24 shControl versus shTTYH1 GBMSCs in vivo over 24 hours (n=3 mice per group; Mann-Whitney test). (G, H) Exemplary in vivo 3D MPLSM images of S24 shControl and shTTYH1 GBMSC TMs (G) as well as T269 shControl and shTTYH1 GBMSC TMs (H). Note that shTTYH1 knockdown cells show morphologically altered TMs with filament beading (arrowheads). B, D-H: data obtained by in vivo MPLSM.

FIG. 21:

(A) Verification of shRNA knockdown of TTYH1 in S24 (left) and T269 (right) GBMSCs by western blot analysis (30% reduction in protein level in S24 and 96%) reduction in T269, respectively). (B) Exemplary in vivo MPLSM images of TM-rich tumor cells in S24 shControl and S24 shTTYH1 tumors showing no phenotypic changes in this cellular subtype. (C) Different cellular subtypes with 0, 1, 2 and more than 4 TMs are also present in T269 and T1 GBMSC lines. (D) Quantification of the fractions of TM-connected GBMSCs in the cellular subgroups with 1-2 TMs versus more than 4 TMs, demonstrating that the majority of cells with more than 4 TMs are connected, whereas the cells with 1-2 TMs are mainly unconnected to other tumor cells in this glioma via their TMs. B-D: data obtained by in vivo MPLSM.

FIG. 22:

TM-Related Glioma Cell Heterogeneity and invasiveness (A) Representative in vivo 3D MPLSM images of cellular subtypes with 0, 1, 2 and more than 4 TMs (S24). (B) Demonstration of cellular subtypes in human astrocytomas (IDH1 R132H mutation specific antibody). (C) Left side: Relative fractions of GBMSCs with 0, 1 or 2, and more than 4 TMs in S24 shControl versus shTTYH1 tumors (20-25 days after implantation) (n=3 mice per group; Two-tailed t-tests). Right side: Absolute number of tumor cells per mm$^3$ categorized regarding these cellular subtypes (n=3 mice per group; ANOVA on ranks). (D) Measurements of the invasion speed of S24 shControl versus shTTYH1 GBMSCs in vivo over 24 hours subcategorized regarding their number of TMs (n=3 mice per group; ANOVA on ranks). A-D: data obtained by in vivo MPLSM.

FIG. 23:

Brain Colonization and Glioma Growth are Strongly Reduced by TTYH1 Deficiency (A-D) Representative single-plane images of S24 shControl (A) and shTTYH1 (B) as well as T269 shControl (C) and shTTYH1 (D) tumors 20 days after implantation demonstrating the reduced invasion caused by the TTYH1 knockdown; middle and right images show higher magnifications of the corresponding regions in the overview (left); GBMSCs (red), blood vessels (turquoise), circle: tumor injection site. Note that tumorigenicity is massively reduced in the highly diffuse infiltrating T269 cell line. (E) Corresponding quantification of invaded S24 tumor cells per range from the main tumor, which was defined as the area with a radial width of 500 µm (n=3 mice per group; Mann-Whitney tests). (F) Absolute number of tumor cells in T269 shControl versus shTTYH1 measured on a single plane image of the whole hemisphere on day 20 (n=3 mice per group; Two-tailed t-test). (G) 9.4 tesla T2 MRI images of S24 shControl (day 72) versus shTTYH1 tumors (day 75 after implantation), and corresponding quantification of tumor area/brain area ratio (n=6 animals per group; Two-tailed t-test); green line: tumor area. (H) Kaplan-Meier-survival plot of S24 shControl versus shTTYH1 tumor-bearing mice (n=6 animals per group; Log Rank test). A-F: data obtained by in vivo MPLSM.

FIG. 24:

TM-Mediated Tumor Cell Interconnections and Radioresistance (A) Ratio of TM-connected/non-TM-connected S24 shControl and shTTYH1 GBMSCs 20 and 40 days after implantation (n=3 mice per group; Mann-Whitney tests). (B) Left side: representative 3D MPLSM images of S24 shControl and shTTYH1 tumors before and 7 days after irradiation (z=51 µm). Right side: corresponding quantification shows absolute cell numbers in a volume of $276*10^3$ µm$^3$ before and 7 days after irradiation (n=3 animals per group; ANOVA on ranks). (C) Ratio of cell number 7 days after/before irradiation with respect to TM connectivity (n=3 mice per group; ANOVA). A-C: data obtained by in vivo MPLSM. The present invention will be further illustrated by the following examples without being limited thereto.

EXAMPLES

Experimental Procedures:

Animals, and Surgical Procedures.

8-10 weeks old NMRI nude mice were used for all studies with human primary brain tumor cells. To investigate the formation of TMs in a syngeneic astrocytoma mouse model, Nestin-Tv-a;Tlx-GFP mice were used in combination with RCAS-PDGFB/AKT vectors. All animal procedures were performed in accordance with the institutional laboratory animal research guidelines after approval of the Regierungspräsidium Karlsruhe, Germany (governmental authority). All efforts were made to minimize animal suffering and to reduce the number of animals used. If mice showed neurological symptoms or a significant weight loss (>20%), experiments were terminated.

Cranial window implantation in mice was done as known in the art: After removal of the skin, the bone of anesthetized mice was drilled out and the meninges were removed. The hole was covered with a round 6 mm glass window, that was glued to the bone with dental cement, and a titan ring that fit into a customized holder was placed on top, to guarantee that no movement artefacts occur during imaging.

2-3 weeks after cranial window implantation, 30,000 tumor cells were stereotactically injected into the mouse brain into a depth of 500 µm, in an angle of 45%. For survival experiments, 50,000 tumor cells were injected. In a subgroup of mice, a short plastic tube was glued under the glass, with one end inside and one outside, which allowed topical application of different substances under the window without the need to re-open it (e.g. for calcium imaging).

For intratumoral microinjection of sulforhodamine 101 (SR101, Molecular Probes, S-359), 50 nl of 100 µM SR101 (with or without 100 µM CBX, Sigma-Aldrich, C4790) were injected with a very thin glass pipette into tumor regions of similar cellular densities, >90 days after tumor injection.

8-10 weeks old male NMRI nude mice (Charles River, Sulzfeld, Germany) were used for studying the growth of primary human brain tumor cell lines in vivo. Cranial window implantation was performed as described above. 2 weeks after cranial window implantation, GBMSC spheroids were split with accutase (A6964, Sigma Aldrich) to obtain a single-cell suspension and 40,000 tumor cells suspended in PBS were injected cortically at a depth of 500 µm. For survival and MRI studies, 50,000 cells (both Ttyh1-knockdown and adequate shRNA control GBMSCs) were injected, as part of a larger experimental approach where multiple gene knockdowns were investigated. Mice were scored clinically and rapidly sacrificed if they showed neurological symptoms or a weight loss >20%. Tumors were irradiated with 7 Gy on three consecutive days at day 57 (+/−8).

Radiation Treatment.

Animals were anesthetized with isoflurane, and established tumors were irradiated with 7 Gy on three consecutive days (total dose 21 Gy) in regions matching in tumor cell density using a 6 MV linear accelerator with a 6 mm collimator (adjusted to the window size) at a dose rate of 3 Gy/min (Artiste, Siemens, Erlangen, Germany)- or no radiation was applied (sham radiation). The time point of radiation was around day 60 (+/−10 days) after tumor implantation. For MRI studies, a total brain radiation with the same dose and a field size of 17 mm×250 mm (allowing the irradiation of several mice) was used with the same accelerator. The eyes and all extra-cranial organs were shielded from the radiation field. The used radiation schedule is clinically relevant: its biological activity is in the range of the commonly prescribed 60 Gy in 2 Gy fractions for malignant glioma patients, assuming an α/β of ~10 in the linear quadratic model and taking into account the short radiation time of 3 days.

In Vivo Multiphoton Laser Scanning Microscopy (MPLSM).

MPLSM imaging was done with a Zeiss 7MP microscope (Zeiss, Germany) equipped with a Coherent chameleon Ultrall laser (Coherent, Scotland). The following wavelengths were used for excitation: 750 nm (dsRed, FITC-dextrane, tdTomato), 840 nm (Fluo-4AM), 850 nm (GFP, TRITC-dextrane, Rhod-2AM), 860 nm (CFP, for FRET imaging) and 950 nm (tdTomato, YFP). Appropriate filter sets [BP 500-550/ BP 575-610 and BP 460-500/ BP 525-560 (for FRET)] were used. Standard settings for imaging were gains between 650 and 750 (depending on the depth, the fluorescence intensity of the fluorophore and the window quality), and a z-interval of 3 µm. Laser power was tuned as low as possible.

During the imaging procedure, body temperature of mice was kept constant using a rectal thermometer and a heating pad. Isoflurane concentration (in 100% $O_2$) was chosen as low as possible (0.5-1.5%) to avoid interference with the calcium communication between astrocytoma cells. Fluorescent dextranes [FITC (2M MW)—or TRITC (500.000 MW)—conjugated, 10 mg/ml, Sigma] were injected i.v. to obtain angiograms, which allowed to determine the relative position of the glioma cells over time.

For in vivo ablation of single astrocytoma cells, only the volume of the GFP-labelled cell nucleus was exposed to continuous scanning with a high power laser beam, and the laser was stopped when disintegration of the nucleus became visible. The region was imaged immediately after the laser-induced death and at 1.5 h, 12h, 24h, 40h, and 60h. To investigate the reaction of TMs after the photodamage of a wider brain region, a larger volume ($0.5-1\times10^6$ µm$^3$) was scanned repetitively for approx. 8 minutes with high power, resulting in a total photon dose that was >50 times higher than during "diagnostic" imaging.

For TTYH1 studies, a BP500-550/BP 575-610 filter and the following wavelengths were used: 850 nm (GFP, TRITC-dextran) and 950 nm (tdTomato). z-intervals of 3 µm and gains between 620 and 750 were used. Laser power was tuned as low as possible to avoid phototoxicity. For in vivo imaging, mice were narcotized with isoflurane (in 100% $O_2$). Mice were fixed using an implanted custom-made titan ring to ensure a stable and painless fixation during the repetitive imaging procedures. The ring also served as a water reservoir allowing longer image acquisition. A high molecular TRITC-Dextran (500 kDa; 52194, Sigma Aldrich; 10 µg ml$^{-1}$) was injected in the tail vein for angiography. Superficial angiograms made it possible to find the exact same region during repetitive imaging time points, and the architecture of the vasculature helped to identify the same cells over a long period of time. During the imaging procedure, body temperature was kept constant using a rectal thermometer and a heating pad.

In Vivo Calcium Imaging with MPLSM.

The following small molecule calcium indicators were used: for GFP-transfected tumor cells: 2 mM Rhod-2 AM (life technologies, R-1244); for RFP-transfected: 2 mM Fluo-4 AM (life technologies, F-14201). The dissolved dyes were applied to the brain surface for 45 min. Regions with a similar tumor cell density were used. For the combination of radiotherapy and calcium imaging, mice were pretreated with Fluo-4AM and imaged after awaking with low isoflurane (0.5%). One hour after radiotherapy, the same regions were imaged again to detect changes in calcium activity. Pharmacological gap junction inhibition was achieved by superfusion with the gap junction inhibitor CBX (100 µM; control substance: extracellular saline; n=3 mice per group). Other superfused substances were suramin (100 µM, ATP antagonist) and 2-aminoethoxydiphenyl borate (2-APB, 100 µM, inhibitor of IP3 receptors).

Two genetically-encoded calcium indicators were lentivirally transduced to GBMSCs: (A) The Lck-GCaMP3 sensor in the rrl-CAG-IGC3 vector (CAG promoter to control expression of DsRed and the Ca$^{2+}$ sensor that monitors near-membrane changes in $[Ca^{2+}]_i$). (B) The radiometric calcium sensor Twitch-3 was used to determine intracellular calcium concentrations by Förster Resonance Energy Transfer (FRET) as known in the art.

MRI Studies.

MRI images were obtained at day 72 after tumor implantation for non-irradiated animals, and at day 115 for irradiated mice (60 days after radiotherapy; timepoints were chosen when first control animals developed neurological symptoms and/or lost 20% weight, and had to be sacrificed). All scans were performed on a 9.4 T horizontal bore MR scanner (BioSpec 94/20 USR, Bruker BioSpin GmbH, Ettlingen, Germany) with a four channel phased array surface coil. The animals were under inhalation anesthesia. A T2-weighted Rapid Acquisition with Refocused Echoes (RARE) sequence was acquired to determine tumor volume.

MRI images were obtained at day 72 (S24 shControl) and day 75 (S24 shTTYH1) after tumor cell implantation on a 9.4 T horizontal bore MR scanner (BioSpec 94/20 USR, Bruker BioSpin GmbH) with a four channel phased array surface coil. To determine the tumor volume a T2-weighted rapid acquisition with refocused echoes (RARE) sequence was used.

Cell Lines and Cell Culture Experiments.

Tumor cell lines derived from resected glioblastomas were cultivated in DMEM-F12 under serum-free ("stem-like") conditions (GBMSCs; P3, S24, T1, T269, T325, WJ). These 6 GBMSC lines were selected because they were capable of growing to tumors in mouse brains. Two oligodendroglioma cell lines harboring the typical 1p/19q codeletion (BT088 and BT054) were kept under the same culture conditions; only BT088 was able to form tumors in mice. To ensure authenticity, typical genetic changes of glioblastoma were confirmed for S24 using comparative genomic hybridization (CGH, cf. FIG. 2i); the T1, T269, T325 and WJ lines had been characterized before, as wells as the P3 line. Cells were regularly checked for mycoplasm infections and authenticity.

Tumor cells were transduced with lentiviral vectors for multicolor imaging, and in vivo detection of different cell compartments. For cytosolic GFP expression, the pLKO.1-puro-CMV-TurboGFP_shnon-target-vector (SHC016 Sigma Aldrich), for cytosolic RFP (tdTomato) expression the LeGo-T2 vector (kind gift from A. Trumpp) were used, and nuclear GFP expression (H2B-GFP) was achieved by transduction with pLKO.1-LV-GFP (Addgene 25999, Elaine Fuchs). Transduction with pLenti6.2 hygro/V5-Lifeact-YFP (kind gift from P. Friedl) made it possible to image the in vivo dynamics of actin filaments, FUmGW (Addgene 22479, Connie Cepko) allowed in vivo illustration of cell membranes. Microtubuli were marked using the Lenti-Brite™ GFP-Tubulin Lentiviral Biosensor (17-10206, Merck Millipore). Lentiviral particles were produced as known in the art. For in vivo tracking of Myosin II, a plasmid transfection with FuGENE® HD (Promega) was performed with the Myosin-IIA-GFP vector (Addgene 38297, Matthew Krummel).

Production of lentiviral knockdowns of Cx43 (pLKO1.1-puro-CMV-tGFP-vector, Sigma Aldrich, target sequence: GCCCAAACTGATGGTGTCAAT; SEQ ID NO: 21) and GAP-43 (pLKO1.1-puro-CMV-vector, Sigma Aldrich, target sequence: TGTAGATGAAACCAAACCTAA; SEQ ID NO: 3) by shRNA technology was carried out as known in the art. Control cells were infected with the appropriate non_target shRNA-lentiviral particles (SHC016, Sigma Aldrich). For overexpression of GAP-43, the open reading frame of GAP-43 was cloned into the pCCL.PPT.SFFV.MC-S.IRES.eGFP.WPRE-vector backbone (kind gift of H. Glimm). Lentiviral particle production and transduction of target cells was done as known in the art.

Tumor cells were incubated with the harvested virus and 8 mg/ml polybrene (Merck Millipore, Darmstadt, Germany) for 24 h. For some purposes, cells were transduced sequentially with different vectors. Transduction efficiency was checked by GFP fluorescence intensity and Western Blot analysis. Quantification revealed a 80% protein knockdown for Cx43 and a 92.5% for GAP-43 (Western Blot analyses).

If necessary, tumor cells were selected for the fluorophores by FACS sorting (BD FACSAria™ II Cell Sorter) or antibiotics.

For tracking of mitochondria, the BacMam 2.0 technology was used (CellLight® Mitochondria-GFP, BacMam 2.0, C10600, Life technologies).

Human primary glioblastoma cell lines (GBMSCs: S24, T269, T325, T1) were cultivated in DMEM-F12 medium (31330-038, Gibco) under serum-free non-adherent conditions, including B27 supplement (12587-010, Gibco), 5 μg ml$^{-1}$ insulin (19278, Sigma Aldrich), 5 μg ml$^{-1}$ heparin (H4784, Sigma Aldrich), 20 μg ml$^{-1}$ epidermal growth factor (rhEGF, 236-EG, R&D Systems) and 20 μg ml$^{-1}$ basic fibroblast growth factor (bFGF, PHG0021, ThermoFisher Scientific). For adherent conditions, S24 glioma cells were cultured in DMEM (D6429, Sigma Aldrich) with 10% FBS (F7524, Sigma Aldrich).

GBMSCs were stably transduced with lentiviral vectors to track the cells during in vivo MPLSM. Cytosolic RFP (tdTomato) expression was achieved by transduction with the LeGo-T2 vector (gift from A. Trumpp). Lentiviral knockdown of TTYH1 (plKO.1-puro-CMV-vector, Sigma Aldrich, target sequence: TCAGACATCCTGAGCTATTAT (SEQ ID NO: 12; for knockdown in S24), GCTCTGAC-CACTAACACTCTT (SEQ ID NO: 16; for knockdown in T269)) and VGF (target sequence not shown) by shRNA technology was carried out as known in the art. ShRNA sequences were chosen from five different target sequences tested, according to their ability to produce a maximum reduction of protein expression while best preserving in vitro growth capabilities of the tumor cells. Control cells were transduced with appropriate pIKO.1-puro-CMV-TurboGFP_shnon-target-vector (SHC016, Sigma Aldrich) lentiviral particles. For transduction cells were incubated with lentiviral particles and 10 μg ml$^{-1}$ polybrene (TR-1003-G, Merck Millipore) for 24 hours.

Western blot analysis revealed a 95% knockdown for VGF and a 30% knockdown for TTYH1 in the S24 GBMSC cell line, and a 96% knockdown in the T269 GBMSC cell line. All cells were regularly tested for mycoplasma infections and species controls were performed for authenticity.

Immunohistochemistry (IHC) and Immunocytochemistry (ICC).

For IHCs and ICCs, standard protocols were used. For human brain analyses, thin (3 μm) formalin-fixed paraffin-embedded human tissue sections were obtained from the Dpt. of Neuropathology in Heidelberg in accordance with local ethical approval. Human sections were incubated with anti-IDH1 R132H (H09, Dianova), anti-Cx43 (C 6219, Sigma), anti-GAP-43 (8945, Cell Signaling), anti-NGF (ab52918, Abcam), anti-NT4 (ab150437, Abcam), anti-TrkA (ab76291, Abcam) and anti-TrkB (ab134155, Abcam) antibodies. If not explicitly stated, all oligodendrogliomas had a 1p/19q codeletion, and all astrocytomas were non-codeleted for 1p/19q. To detect contralateral tumor cells in human brains, large sections were analyzed as known in the art. For immunofluorescence detection of IDH1 R132H positive tumor cells in thick human brain tumor sections, paraformaldehyde (PFA) fixed human samples were cut in 100 μm sections and incubated for 24 hours with the IDH1 R132H antibody.

For mouse brain analyses, animals were transcardially perfused with PBS followed by 4.5% PFA. For ICCs, cells were grown on glass slides for 4 days and fixed with PFA. The following antibodies were used for 10 μm cryotome sections and ICCs: anti-nestin (ab6320, Abcam, specific staining of the human nestin intermediate filament, which is highly expressed in GBMSCs, but not detectable in normal mouse brain), in combination with anti-β-catenin (ab16051, Abcam), anti-β-parvin (sc-50775, Santa Cruz), anti-beta tubulin III (ab18207, Abcam), anti-Cx26 (ab59020, Abcam), anti-Cx31 (ab156582, Abcam), anti-Cx37 (ab185820, Abcam), anti-Cx43 (C6219, Sigma), anti-GAP-43 (8945, Cell Signaling), anti-GFAP (Z0334, Dako), anti-Ki-67 (M7240, Dako), anti-myosin IIa (ab24762, Abcam), anti-myosin X (22430002, Novus Bioscience), anti-N-Cadherin (ab18203, Abcam), and anti-PDI (ab3672, Abcam). Images were acquired using a Leica SP5 confocal microscope.

In TTYH1 studies, for immunohistochemistry, mice with fully established brain tumors were cardially perfused with PBS, followed by 4.5% phosphate-buffered formaldehyde solution (Roti-Histofix 4.5%, 2213, Carl Roth). Brains were incubated in 30% sucrose solution over night for cryoprotection and frozen afterwards. Heat-induced epitope retrieval with 0.01 M citrate buffer (pH=6.0) was performed prior to immunohistochemical staining. For immunocytochemistry, cells were grown on cover slips for 3 days and fixed with 4.5% formaldehyde solution (Roti-Histofix 4.5%, 2213, Carl Roth) or acetone afterwards. The following antibodies were used for the staining of 10 μm cryotome sections and ICCs: anti-nestin (ab6320, Abcam), anti-TTYH1 (HPA023617, Sigma Aldrich), anti-Integrin α5 (ab6131, Abcam), anti-VGF (PA5-20523, ThermoFisher Scientific). As secondary antibodies goat anti-mouse IgG, Alexa Fluor 488 conjugate (A-11029, ThermoFisher Scientific) and goat anti-rabbit IgG, Alexa Fluor 633 conjugate (A-21070, ThermoFisher Scientific) were used. For demonstration of cellular subtypes in human IDH1-mutated astrocytoma specimen, human brain tumor specimens were fixed in 4% PFA and 100 μm sections were cut on a vibratome. Heat-induced antigen retrieval was performed with Tris-EDTA buffer. Free floating sections were incubated with the primary antibody anti-IDH1 R132H (DIA H09; Dianova) for 24 hours. A AF488 conjugated anti-mouse secondary antibody (A11029; life technologies) was used. Sudan Black solution was used for reduction of auto-fluorescence. For IDH1/TTYH1 costainings of human astrocytoma specimen, 3 μm sections of paraffin-embedded tissue samples were deparafinized and heat-induced antigen retrieval was performed with Cell Conditioning Solution (pH=6.0) (CC2, #950-123, Ventana). Anti-IDH1 R132H (DIA H09; Dianova) and anti-TTYH1 (HPA023617, Sigma Aldrich) primanry antibodies were used.

Confocal immunohistochemical and immunocytochemical images were acquired using a Leica TCS SP5 microscope.

Photo-Oxidation of GFP, and Serial Section Scanning Electron Microscopy (SEM).

Ten S24 GBMSC brain tumor tissue blocks were prepared for photo-oxidation as known in the art. Serial 70 nm thick sections of photo-oxidated epon-embedded tissue were produced using 3D SEM as known in the art. A volume of 747 μm$^3$ was imaged, and 6 from 51 analyzed tumor filaments therein were reconstructed for analysis of the TM diameter. For illustration purposes, also axons were reconstructed. Specimens were imaged with a Zeiss 1530 scanning electron microscope. Images were aligned manually. The plasma membrane of the TMs and axons were manually traced in each section resulting in a set of contours.

For EM of spheroids, five day old spheroids were fixed with 4% PFA/0.5% GA, incubated in cacodylic acid and postfixed in 1.5% potassium ferrocyanide and 2% osmium tetroxide. Sections were dehydrated and stored in epoxy/propylenoxide (1:1) over night. The sections were embedded in epoxy resin. Serial sections were prepared and a volume of 2692 µm³ was analysed.

Western Blot.

Western blots were performed according to standard protocols. Total protein lysates (20-50 µg) were electrophoretically separated using a 10% SDS-PAGE. After blotting and blocking, the following antibodies were used over night at 4° C.: anti-Cx26 (ab59020, Abcam), anti-Cx31 (ab156582, Abcam), anti-Cx37 (ab185820, Abcam), anti-Cx43 (C 6219, Sigma), anti-GAP-43 (8945, Cell Signaling). As loading control, anti-GAPDH antibody (C4780, Linaris), or anti-alpha-tubulin antibody (T9026, Sigma) was used.

For TTYH1 studies, gels were incubated with anti-TTYH1 (HPA023617, Sigma Aldrich) and anti-VGF (PA5-20523, ThermoFisher Scientific) antibodies after blotting and blocking over night at 4° C. Blots were incubated with HRP-linked donkey anti-rabbit secondary antibody (NA9340-1 ml, GE Healthcare) at room temperature for 1 hour. As loading control anti-GAPDH (C4789, Linaris) and donkey anti-goat IgG-HRP (sc-2020, Santa Cruz Biotechnology) antibodies were used. Protein expression levels were measured with ImageJ (National Institutes of Health, Bethesda, Md.) after digitalization of Super RX-N films (Fujifilm).

Electroporation/Microinjection.

Horizontal acute brain slices were obtained from 2 NMRI nude mice with 131 days old S24 as known in the art. Patch electrodes with resistances of 5-10 MΩ were filled with lucifer yellow (5 mg/ml, L0259, Sigma Aldrich) and approached to identified tumor cells under visual control using a 63×, NA 1,0 dipping lens (Zeiss). The dye was transferred into tumor cells with an Axoporator 800A (Axon instruments) by 1 ms square voltage pulses at 50 Hz. Pulse amplitude was adjusted between −5V and −20V and train duration was adjusted up to 3 s to receive sufficient labelling of the target cell. Following electroporation, we obtained two color sequential confocal stacks (LSM 5, Zeiss).

Image Processing.

MPLSM images were acquired by the ZEISS ZEN Software (Zeiss, Germany). After primary image calculation (e.g. subtraction of different channels to remove unspecific background) images were transferred to Imaris (Bitplane, Switzerland) to allow 3D visualization, rendering and analysis of the data (for details see below). Here, a subset of images was filtered with a Gaussian filter after analysis and before extraction. For illustration of different aspects single planes, maximum intensity projections (MIPs) or 3D images were used. For exemplary illustration of tumor cell inter-connectivity and TM branches, z-stacks were rendered manually (tumor cell bodies: surface function; TMs: filament tracker function). When a TM started at one cell and ended at another, these cells were defined as connected. Serial electron micrographs were reconstructed using OpenCAR software. 3D analysis of EM images was done using the Amira 5.4.6 software (Visage Imaging, Richmond, Australia). Some of the data (e.g. calcium imaging) were transferred to the ImageJ software (Rasband, W.S., ImageJ, U.S. National Institutes of Health, Bethesda, Md., USA). Videos were extracted from ZEN or Imaris and edited in Adobe Premiere (Adobe Premiere Pro CS6, USA).

Quantification of Histology and MPLSM Imaging Data.

In patient tumor tissue (only from primary tumor resections), maximum TM length was measured in standard 3 µm thin IDH1-IHC sections. Here, TMs were divided into 3 groups: <50 µm (not qualifying as definite TM, because other cellular structures might still be confused with filamentous structures of this length); shorter TMs of 50-100 µm, and longer TMs of >100 µm length. Quantitative analysis of human IHCs was done by a Histo-Score (range 0-300) as known in the art.

For in vivo imaging data, TM numbers, branches/TM and connections/cell were counted manually, and TM lengths were measured manually in the slice mode in Imaris. For quantification and analysis of tumor cells/TMs before and after radiotherapy, cells were counted in the same regions before radiation or sham radiation, and at different time points afterwards. Cells without a TM-connection were defined as "non-connected" and cells with at least one TM-connection(s) as "connected". To analyze the number of TMs before and after irradiation, the TMs of individual, identical cells were counted at both time points. Ratios were calculated to determine the relative changes of cell and TM numbers over time. For the measurement of tumor volumes in BT088 tumors before and after radiotherapy, two regions were analyzed per animal using the surface function of Imaris. The mean speed of tumor cell invasion in S24 shControl vs. shGAP-43 tumors was determined by analysis of three consecutive imaging time points within a 24 hour time interval in vivo. Distances of tumor cells to the main tumor mass (defined as a radius of 0.5 mm around the middle of the main tumor) were analyzed and grouped, or displayed as individual distances to the main tumor core in tumors that were much less invasive (oligodendrogliomas). Nuclei and mitochondria (time-lapse imaging data) were marked using the spot function of Imaris. They were connected to tracks and the mean track speed was calculated. Mitochondria were classified as located in a TM ("TM") or soma of the tumor cells ("soma"). For quantification and analysis of fluorescence intensity after SR101 application, all GFP-expressing tumor cells in a volume were marked using the spot function of Imaris and then mean intensities of the SR101-channel of these spots were calculated and compared with each other. For analysis of lucifer yellow injected cells, these cells had been grouped as "connected" or "not-connected" depending on their ability to transfer the dye to neighboring cells before analysis of the mean fluorescence intensities for lucifer yellow in these cells.

Ki67-positive cells were counted in 2 regions (main tumor mass)/animal and divided by the total number of DAPI stained nuclei in these regions.

Quantification and Analysis of Calcium Imaging Data.

Tumor cells or non-malignant brain astrocytes were marked manually by the use of the ROI Manager of ImageJ. Mean gray values were measured over time. This data was processed by the program GNU Octave 3.8.1 (John W. Eaton, GPL): images were normalized to the background fluorescence utilizing a sliding interval of ±10 images. Local maxima of calcium signals were detected by the findpeaks function (signal package, Octave-Forge). Thus, the number of calcium peaks of each cell (N) could be determined and the frequency (f) was calculated. The frequency was standardized for the cell number of each region to ensure comparability. Synchronous cells, the number of synchronous communications, and the time point of the synchronous firing were determined. Due to the fact that the images were recorded via a line mode, which leads to a latency of signal detection, the analysis was done in a window of 2 frames around each peak. This allowed to assess the synchronicity S ($S \in R^+ \cup \{0\}$), which was defined as the fraction of the whole number of synchronous cells (N_Syn) divided by the number of calcium peaks for the given cell (N_Ca). In case the cells were not active, a synchronicity of zero was allotted.

$$\text{Synchronicity } S = \begin{cases} \dfrac{N_{Syn}}{N_{Ca}} & \text{for } N_{Ca} > 0 \\ 0 & \text{for } N_{Ca} = 0 \end{cases}$$

Hence, synchronicity states the average number of interactions at the same time point. For example, in a system with a synchronicity of 1, a firing cell interacts with a second one. For a synchronicity of 10, one active cell is communicating with 10 other cells.

For the comparison between different blockers in vivo, the synchronicity was normalized to the baseline level.

Finally, the results were summed up by a heat map. The number of calcium peaks of these cells were coded by a color map. Synchronic cells were connected by lines, whereat the color described the timepoint of the synchronic firing.

For measurement of relative changes in fluorescence intensity, tumor cells were again marked manually and relative changes were calculated (deltaF/F0). F0 was defined as the average intensity of the 20% lowest grey values in a ROI.

For quantification of intracellular calcium levels, the fluorescence intensities of cpVenusCD and CFP were measured in TM-connected and non-connected cells before and 2 days after radiotherapy using the spot function of Imaris. For each cell, these values were plotted and a linear regression analysis was performed. High $r^2$-values represented a homogenous calcium concentration in the different populations, whereas low $r^2$-values mirrored heterogeneous calcium levels in a population of cells.

Quantification and Analysis of MRI Images.

The slice with the largest tumor area per mouse was chosen, and both the tumor (hyperintense on T2-weighted images) and the whole brain were segmented manually. The ratio of these two areas were determined and compared between the different groups (n=6 mice per group, t-tests).

Functional Characterization of Differential mRNA Expression.

RNA sequencing raw data (mapped to genes) and curated IDH-1/2 mutation data were first downloaded from The Cancer Genome Atlas (TCGA) data portal on Jan. 30, 2015, and last updated on May 6, 2015. Additionally, copy-number calls (using GISTIC 2.0) from the cBioPortal64 and 450k- as well as CNV-NMF-clustering results from the Broad GDAC Firehose (http://gdac.broadinstitute.org/) were acquired. Only IDH mutant samples which clearly clustered to either the codeleted or non-codeleted group (and had the respective copy-number profile)—197 samples (127 non-codeleted, 70 codeleted) in total—were kept for further analysis. First, normalization and differential gene expression analysis of RNA sequencing counts was performed using the edgeR package65, which assumes a negative binomial distribution of count data, filtering lowly expressed transcripts. Differentially activated signaling pathways and downstream effects between codeleted and non-codeleted IDH mutant tumors were analyzed with the proprietary Ingenuity Pathway Analysis (QIAGEN, Redwood City, Calif., USA) using a fold change filter of |1.5| and FDR-q <0.0566 for the input list. Briefly, the software calculates both an overlap p value (based on Fisher's exact test) and an activation z score, which is based on the expression state of activating and inhibiting genes, for manually curated pathways and downstream biological functions. For this exploratory, hypothesis-generating study, results with both p<0.1 and a z score>|1.5| were kept.

Statistics.

The results of image analyses were transferred to the SigmaPlot Software (Systat Software, Inc., San Jose Calif., USA) to test the statistical significance with the appropriate tests (data were tested for Normality using the Shapiro-Wilk-Test and for equal variance). Quantifications were done blinded by two independent investigators. Statistical significance was assessed by the two-sided Student's t-test for normally distributed data. Otherwise a Mann-Whitney test was used for non-normal distributions. For more than two groups a one way ANOVA or an ANOVA on the ranks was performed. For Kaplan-Meier Survival analysis, a log rank test was performed. Results were considered statistically significant if the p-value was below 0.05. Animal group sizes were empirically chosen and longitudinal measurements allowed a reduction of animal numbers by maintaining an adequate power. If treatments were applied, animals were randomized to these procedures. Quantitative in vivo data are normally depicted as mean±standard deviation. The calculated calcium imaging frequency and synchronicity values were corrected for outliers using the Nalimov' test.

For TTYH1 studies, the obtained quantitative data was transferred to the SigmaPlot Software (Systat Software GmbH, Germany) to test for statistical significance with appropriate tests. Data sets were tested for normality with Shapiro-Wilk test. Statistical significance of normally distributed data was assessed by a two-sided Student's t-test. Non-normally distributed data was assessed with a Mann-Whitney Rank Sum test. For statistical analyses of data sets with more than two groups ANOVA or ANOVA on ranks with the appropriate post-hoc tests (Tukey's for ANOVA, Student-Newman-Keuls and Dunn's for ANOVA on ranks) were performed. For Kaplan-Meier survival analysis, a log rank test was performed. For the correlation between the TTYH1 protein level and the correlation coefficient a linear regression analysis was performed. Results were considered statistically significant if the p-value was <0.05.

Quantitative MPLSM in vivo data are depicted as mean, error bars show standard deviations. * P<0.05,  P<0.01, * P<0.001

Invasion Assay.

For studying the invasion capacity of human GBMSCs in vitro, single GBMSC spheroids were seeded into a Collagen I matrix gel (Collagen I, A1048301, ThermoFisher Scientific; MEM, 31095-029, Gibco; Fibronectin, F2006, Sigma Aldrich) and the spreading of single GBMSCs was monitored by light microscopic images after 0 and 48 hours. For quantification, the radial distance of the 60 furthest invaded glioma cells in the full circumference of the spheroid (approximately one cell per)6°) was measured and expressed as difference to the mean radial distance of the spheroid at 0 hours.

Quantification of MPLSM Imaging and MRI Data.

For TTYH1 studies, in vivo MPLSM data was analysed using Imaris (Bitplane, Switzerland) and ImageJ (National Institutes of Health, Bethesda, Md.). For measurements of TM length, TMs were measured manually in slice mode of Imaris. For the measurements of the invasion distance, the radial distance of all invaded tumor cells from the borders of the tumor bulk were measured in Imaris slice mode. The invasion speed of different subgroups of GBMSCs in vivo was determined by following single tumor cells over three time points within 24 hours on day 20 (+/−1) after tumor injection. The distance of tumor cells from the tumor bulk (defined as an area with a radial width of 500 μm) was measured in a single plane image. The number of TMs per cell, the connectivity and cell numbers before and after radiation therapy were counted manually in the same regions at different time points. A cell was classified as connected if at least one of its TMs connected two tumor cell bodies directly. For the invasion coefficient the number of cells more than 1500 µm from the tumor bulk center were set in proportion to the tumor bulk area.

For the quantification of the tumor/brain area ratio in MRIs, the tumor and the whole brain area were measured manually in the T2-weighted slide with the largest tumor expansion.

RNA Microarray and Ingenuity Pathway Analyses

For RNA microarray analysis, cells were either cultured under serum-free non-adherent or adherent conditions for 4 weeks. Biological triplicates were harvested and RNA was isolated using a RNeasy Mini kit (74104, Qiagen). RNA was eluted in TE/water. The quality of total RNA was checked by gel analysis using the total RNA Nano chip assay on an Agilent 2100 Bioanalyzer (Agilent Technologies GmbH, Berlin, Germany). Only samples with RNA index values greater than 8.5 were selected for expression profiling. Illumina Human Sentrix-12 BeadChip arrays (Illumina, Inc.) were prepared according to Illumina's recommended sample labeling procedure based on the modified Eberwine protocol. Microarray scanning was done using an iScan array scanner. Data extraction was done for all beads individually, and outliers were removed when the absolute difference to the median was greater than 2.5 times MAD (2.5 Hampel's method). All remaining bead level data points were then quantile normalized. To test for significance the student's t-test was used on the bead expression values of the two groups of interest. In the case of significance of expression against background we tested for greater than all negative beads for this sample and in the case of comparing separate groups we tested for inequality of the means of the groups. In both cases Benjamini-Hochberg correction was applied to the complete set of p-values of all ProbeIDs on the chip. The average expression value is calculated as mean of the measured expressions of beads together with the standard deviation of the beads.

The list of differentially expressed genes was input into Ingenuity Pathways Analysis (Qiagen, Redwood City, Calif., USA), using a fold change >12.51 & FDR-adjusted p-value <0.05 as inclusion criteria. Briefly, the software calculates both an overlap p value (based on Fisher's exact test) and an activation z score, which is based on the expression state of activating and inhibiting genes, for manually curated biological functions. To derive an activation score for function categories, we calculate a mean activation z score for all functions included in the respective category and in parallel generated a running sum statistic which was increased by 1 when a function was activated (z>0) and decreased by 1 when a function was inhibited (z<0) and finally divided by the number of functions in a category. The category activation score was calculated as mean z score * |running sum|, to highlight homogeneously activated categories.

Example 1

Membrane Tubes in Glioma Progression

To study the occurrence and dynamics of membrane tube protrusions in mammalian tumors, gliomas growing in the mouse brain were followed by in vivo multiphoton laser-scanning microscopy (MPLSM) in three dimensions up to a depth of 750 µm, for up to one year. After transplantation of patient-derived glioblastoma cell lines (n=6) that were kept under serum-free, stem-like conditions (GBMSCs; FIG. 2), many tumor cells formed ultra-long cellular protrusions. These protrusions infiltrated the normal brain at the invasive front (FIG. 1a), where astrocytoma cells extended and retracted them in a scanning mode. Analysis of protrusion tip dynamics revealed a high motility (FIG. 2I), similar to neuronal growth cones during development. When tumors progressed, the number of cellular protrusions increased further, some exceeding 500 µm in length (FIG. 1b). The resulting membrane tubes where used as tracks for travel of cell nuclei, e.g. after nuclear division (FIG. 1c). Taken together, these data suggest that membrane tube formation is an effective means of tumor dissemination, adding to the known strategies.

All membrane tubes were actin-rich (FIG. 1d), which is also typical for most membrane nanotubes (MNs). Moreover, immunohistochemistry and live imaging revealed that they were indeed enclosed by a continuous cell membrane, and positive for myosin IIa, microtubules, and protein disulfide isomerase; partly positive for β-catenin, β-parvin, and the astrocytic marker GFAP; but largely negative for N-cadherin, myosin X, and the neuronal marker β-tubulin III (FIG. 3a,b). Together this indicates that these membrane tubes have a unique composition and a potent motility machinery; the latter is shared with other cellular extensions like MNs, filopodia, and neurites. Dendritic arborization was frequent, with thin membrane tubes originating from thicker ones (FIG. 1d,e). While thicker tubes often remained stable over long periods of time, up to more than 100 days (FIG. 3c), smaller side branches were more dynamic (FIG. 1e). To allow ultrastructural analysis of these thin tumor cell-derived tubes in the mouse brain by electron microscopy (EM), photooxidation of brain sections was performed. This resulted in dark precipitates within the green fluorescent protein (GFP)-expressing astrocytoma cell tubes (FIG. 3d). Serial-section scanning electron microscopy (3D SEM) revealed that the cell membrane-enclosed tubes had a mean cross sectional area of 1.57±0.33 µm$^2$ (n=6, FIG. 3e), and contained mitochondria and vesicles (FIG. 1f), suggesting local ATP production and vesicle trafficking in the tubes. Interestingly, the mitochondria travelled more quickly in these membrane microtubes than in the cell soma (FIG. 3f). Furthermore, 3D SEM revealed that a relevant number of membrane microtubes were following axons in the brain (19.6% of n=51; FIG. 1f, FIG. 3g), which are known leading structures for tumor cell dissemination in astrocytomas.

In vivo imaging of membrane tube development over time revealed that an increasing number started at one and ended at another astrocytoma cell, creating a multicellular anatomical network (FIG. 1g,h). Abundant intercellular membrane tubes were also found in a genetic astrocytoma model where GFP expression is driven by the promoter of the nuclear receptor tailless (Tlx), marking a tumor cell subpopulation with stem cell properties (FIG. 3h). Intercellular membrane tubes were in part a result of cell division, with enduring stable contact of daughter cells over long distances (FIG. 1c), but also of mating of non-related astrocytoma cells (FIG. 4a-f). Membrane tube formation of tumor cells appeared to be an inherent feature of astrocytoma cells, not restricted to the brain microenvironment (FIG. 4g). A small proportion of membrane tube-bearing astrocytoma cells maintained quiescent for months, often in a perivascular niche that has been associated with glioma cell stemness (FIG. 4h,i).

The intercellular position of many astrocytoma membrane tubes, together with their high content of F-actin, is reminiscent of MNs; however, the MNs reported so far had a width of below one μm; a length of usually tens, rarely a few hundreds of μm; and documented life time of less than 60 minutes. These differences led to the proposal of the new term "tumor microtubes", or TMs, for the discovered ultra-long, long-lived, and thicker membrane extensions of astrocytoma cells. This does not exclude that tumor cell MNs in vitro might be a model for TMs in vivo, where much longer time intervals are available for growth of size, extent of intercellular connectivity, and increase in functionality.

Example 2

Tumor Microtubes Characterize Treatment-Resistant Gliomas

To investigate whether TMs are also characteristic for human brain tumors, resected WHO II°-IV° glioma tissue from patients were stained. To unambiguously detect tumor cell-derived structures within the filament-rich brain parenchyma, the mutation-specific antibody against IDH1-R132H was used. Like in the astrocytoma mouse models, TMs were abundant in human astrocytomas (FIG. 5a): 63% of astrocytoma cells had intercellular TMs (n=196 cells in 100 μm thick sections of n=8 WHO II°-III° tumors without 1p/19q codeletion). This number was particularly well reflected by the S24 GBMSC cell line at later time points of growth in mice brains (FIG. 1b,h; day 60), thus this model was chosen as the principle one for further in vivo studies.

Figure 6:
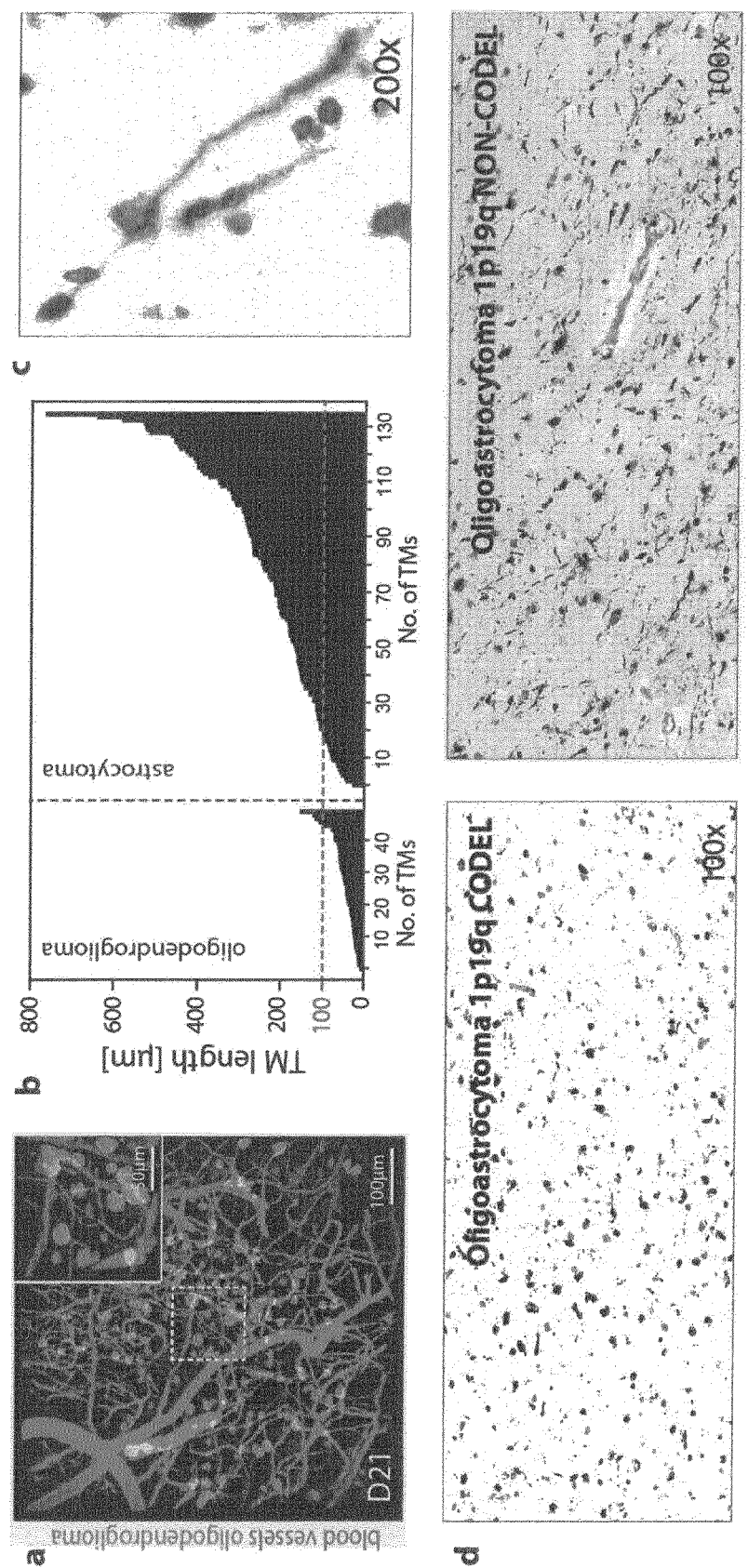

In contrast, only 0.7% of oligodendroglioma cells in human tumor samples had intercellular TMs (FIG. 5b; n=150 cells from n=3 oligodendrogliomas with 1p/19q codeletion), and also in patient-derived oligodendroglioma cells that formed tumors in mice (FIG. 6a,b). Further analysis of 105 human gliomas revealed that TM formation was highly influenced by tumor type and grade, with a striking positive correlation of TM length and unfavorable prognosis: e.g., bona-fide TMs of a minimum of 50 μm length in standard thin sections were detectable in only 19% of WHO II° oligodendrogliomas, but 93% of WHO IV° astrocytomas (=glioblastomas) (FIG. 5c). In astrocytomas, TMs were even detected in the contralateral brain hemisphere that was macroscopically tumor-free (FIG. 6c). In gliomas histologically classified as WHO oligoastrocytomas, the 1p/19q codeletion status strongly determined TM length in these otherwise morphologically similar tumors (FIG. 5d, FIG. 6d). Moreover, 1p/19q status better predicted TM occurrence than morphological glioma classification (FIG. 5e).

In summary, TMs are characteristic for 1p/19q non-codeleted gliomas, where they connect single tumor cells with each other, but are largely missing in 1p/19q codeleted tumors. This was a first indication that TMs might be involved in treatment resistance.

Example 3

A Communicating Network

Intercellular calcium waves (ICWs) can coordinate the activity of individual cells in a multicellular tissue, thus creating a communicating functional network, which includes astrocytes of the normal brain, neurons, and radial glia cells during CNS development. It was examined whether TM connections convey ICWs between disseminated, but TM-connected astrocytoma cells. Indeed, combining both small-molecule and genetically-encoded calcium sensors with in vivo MPLSM, extensive and long-range ICWs were observed, involving many astrocytoma cells in various tumor regions. ICWs were propagated along TMs in both directions (FIG. 7a, FIG. 8a). Further analysis confirmed that ICWs, measured by synchronicity of calcium fluctuations (see Methods for details), were largely restricted to astrocytoma cells with detectable TM-connections (FIG. 7b,c), allowing communication of individual cells in a reproducible pattern (FIG. 7c,d; FIG. 8b,c).

For MNs, intercellular connections have been reported in vitro to either be open ended, or separated by gap junctions. Interestingly, the latter appears to be a prerequisite for ICW propagation. Thus, the hypothesis that gap junctions, which allow for the exchange of small molecules between cells, were involved in TM-mediated ICWs was tested. Indeed, pharmacological gap junction blockade reduced the frequency and synchronicity of ICWs in GBMSC astrocytoma cells in vivo, but not in co-registered brain astrocytes of that tumor region (FIG. 7e). Inhibition of inositol triphosphate (IP3), which is gap junction-permeable and the effector of gap junction-mediated ICW propagation also reduced ICWs between astrocytoma cells (FIG. 8d). ATP receptors are another component of ICW propagation, and their blockade reduced ICWs both in malignant and normal astrocytic cells (FIG. 8d).

The functional connection of single astrocytoma cells via TM-associated gap junctions was verified by rapid distribution of the gap-junction permeable dye sulforhodamine 101 in the TM-connected cellular tumor cell network in vivo after local injection (FIG. 7f), which was inhibited by gap junction blockade (FIG. 7g). Further experiments confirmed that another gap-junction permeable molecule was transferred between TM-connected cells (FIG. 8e-g), while gap-junction impermeable large molecules were not (FIG. 4c).

In summary, these data demonstrate that TMs are substantial for connection of single astrocytoma cells to a functional network via gap junctions, involving both the solid and the invasive tumor areas.

Example 4

Connexin 43 Connects TMs

To identify which of the known 21 gap-junction forming human connexins is involved in TM-mediated cell-to-cell communication in astrocytomas, it was hypothesized that the deficiency of 1p/19q codeleted gliomas for intercellular TMs might also result in lower expression of the relevant TM-associated connexin(s). Up to today, conflicting results and multiple functions have been reported for the different connexins in glioma pathology. Analysis of 197 IDH mutant glioma samples of the TCGA dataset revealed a list of differentially expressed genes between 1p/19q non-codeleted vs. codeleted tumors (Table 1).

TABLE 1

Results of the differential gene expression analysis of 1p/19q non-codeleted (n = 127) vs. codeleted (n = 70) IDH-mutated grade II and III gliomas of the TCGA database.

| rank | RefName | EntrezID | logFC | logCPM | PValue | FDR |
|---|---|---|---|---|---|---|
| 1 | psiTPTE22 | 387590 | 4.419501199 | 5.584319239 | 1.23E−57 | 1.34E−55 |
| 2 | PI16 | 221476 | 2.856230506 | 5.43277481 | 4.10E−26 | 8.45E−25 |
| 3 | VCAM1 | 7412 | 2.844459103 | 6.22153792 | 2.21E−48 | 1.47E−46 |
| 4 | SULF1 | 23213 | 2.519045783 | 5.755388645 | 2.64E−31 | 7.29E−30 |
| 5 | GBP2 | 2634 | 2.504857232 | 6.075727092 | 7.05E−24 | 1.25E−22 |
| 6 | MSTN | 2660 | 2.393211231 | 5.073372267 | 3.17E−22 | 5.09E−21 |
| 7 | SCIN | 85477 | 2.37492593 | 5.352228617 | 1.20E−21 | 1.83E−20 |
| 8 | VIM | 7431 | 2.340787112 | 10.22775475 | 1.41E−38 | 5.87E−37 |
| 9 | ID3 | 3399 | 2.272133531 | 8.264480032 | 6.52E−68 | 1.18E−65 |
| 10 | IFI44L | 10964 | 2.187273465 | 6.819732478 | 4.26E−21 | 6.30E−20 |
| 11 | CTSH | 1512 | 2.176036634 | 6.944328219 | 4.70E−29 | 1.14E−27 |
| 12 | CX3CR1 | 1524 | 2.110086998 | 6.928705433 | 3.66E−27 | 7.95E−26 |
| 13 | STOX1 | 219736 | 2.039846105 | 5.44957254 | 6.84E−48 | 4.40E−46 |
| 14 | CHST9 | 83539 | 1.939744525 | 6.299341521 | 1.55E−37 | 6.10E−36 |
| 15 | FCGR3A | 2214 | 1.92937674 | 6.545690554 | 3.26E−17 | 3.66E−16 |
| 16 | TMEM119 | 338773 | 1.906375404 | 5.355566776 | 2.45E−31 | 6.82E−30 |
| 17 | C3 | 718 | 1.90211232 | 9.269123585 | 7.02E−24 | 1.25E−22 |
| 18 | GPX3 | 2878 | 1.86973372 | 8.769688384 | 1.31E−15 | 1.29E−14 |
| 19 | CYBB | 1536 | 1.835415091 | 6.234494306 | 3.16E−28 | 7.25E−27 |
| 20 | EMP1 | 2012 | 1.834135809 | 6.881390481 | 3.74E−28 | 8.52E−27 |
| 21 | GNG12 | 55970 | 1.820458644 | 5.716567033 | 8.18E−43 | 4.24E−41 |
| 22 | GLIS3 | 169792 | 1.807535921 | 5.316176886 | 4.77E−34 | 1.56E−32 |
| 23 | S1PR3 | 1903 | 1.7793768 | 5.693925488 | 3.13E−24 | 5.73E−23 |
| 24 | C4A | 720 | 1.77396035 | 9.356125273 | 1.11E−23 | 1.95E−22 |
| 25 | CSF1R | 1436 | 1.769274446 | 7.932815972 | 1.44E−33 | 4.55E−32 |
| 26 | FCGBP | 8857 | 1.767105198 | 7.413173555 | 6.48E−10 | 3.65E−09 |
| 27 | SLC2A5 | 6518 | 1.733874967 | 5.712717101 | 3.87E−28 | 8.77E−27 |
| 28 | ASAP3 | 55616 | 1.728614705 | 6.161999926 | 6.72E−104 | 8.93E−101 |
| 29 | VSIG4 | 11326 | 1.722729451 | 6.398256559 | 5.40E−22 | 8.47E−21 |
| 30 | APBB1IP | 54518 | 1.688615364 | 5.175551918 | 5.84E−26 | 1.18E−24 |
| 31 | SLC14A1 | 6563 | 1.686566128 | 6.690859212 | 2.04E−08 | 9.87E−08 |
| 32 | RHBDF2 | 79651 | 1.657305399 | 5.211084103 | 1.22E−32 | 3.59E−31 |
| 33 | ANXA1 | 301 | 1.65147736 | 5.699546049 | 1.61E−11 | 1.07E−10 |
| 34 | NCKAP1L | 3071 | 1.622180534 | 5.023733112 | 3.17E−25 | 6.18E−24 |
| 35 | ITGB4 | 3691 | 1.616289804 | 6.638836493 | 3.53E−17 | 3.95E−16 |
| 36 | ITGB2 | 3689 | 1.611231495 | 6.661157057 | 2.04E−21 | 3.07E−20 |
| 37 | CD14 | 929 | 1.610309084 | 6.688998526 | 7.12E−17 | 7.74E−16 |
| 38 | CYR61 | 3491 | 1.59320671 | 5.859281289 | 4.20E−12 | 2.99E−11 |
| 39 | WNT5A | 7474 | 1.586977796 | 4.815797944 | 5.26E−40 | 2.30E−38 |
| 40 | FYB | 2533 | 1.586631733 | 5.082136074 | 7.17E−21 | 1.04E−19 |
| 41 | FNBP1L | 54874 | 1.580629677 | 5.739134488 | 8.00E−63 | 1.18E−60 |
| 42 | C3AR1 | 719 | 1.568367139 | 5.206632449 | 1.65E−22 | 2.71E−21 |
| 43 | SYK | 6850 | 1.559415909 | 4.993089913 | 2.17E−25 | 4.28E−24 |
| 44 | HLA-DRA | 3122 | 1.550234591 | 8.504758085 | 1.10E−10 | 6.77E−10 |
| 45 | ADORA3 | 140 | 1.550014195 | 5.584222271 | 3.49E−26 | 7.23E−25 |
| 46 | LILRB4 | 11006 | 1.538197805 | 5.174206255 | 3.14E−21 | 4.68E−20 |
| 47 | C1QB | 713 | 1.514018885 | 7.990107445 | 1.45E−16 | 1.55E−15 |
| 48 | PLD4 | 122618 | 1.511227382 | 4.870047708 | 5.91E−19 | 7.68E−18 |
| 49 | NMB | 4828 | 1.506432102 | 7.335009538 | 8.07E−15 | 7.37E−14 |
| 50 | DOCK8 | 81704 | 1.50576356 | 5.084409081 | 7.07E−24 | 1.25E−22 |
| 51 | DOCK2 | 1794 | 1.504522413 | 4.715726906 | 2.49E−22 | 4.04E−21 |
| 52 | HCLS1 | 3059 | 1.489907309 | 5.888197007 | 2.88E−20 | 4.08E−19 |
| 53 | C2orf67 | 151050 | 1.486003406 | 4.783705413 | 7.62E−83 | 2.76E−80 |
| 54 | C1QC | 714 | 1.481582124 | 7.812675768 | 2.23E−17 | 2.52E−16 |
| 55 | HLA-DMB | 3109 | 1.478296548 | 5.554234398 | 1.87E−15 | 1.83E−14 |
| 56 | LAPTM5 | 7805 | 1.4716604 | 8.059099362 | 8.17E−26 | 1.64E−24 |
| 57 | HAVCR2 | 84868 | 1.469045817 | 5.114430862 | 7.42E−23 | 1.25E−21 |
| 58 | CD74 | 972 | 1.467036007 | 9.98659415 | 3.48E−12 | 2.49E−11 |
| 59 | DHRS3 | 9249 | 1.464790739 | 5.945726621 | 9.42E−37 | 3.63E−35 |
| 60 | DOCK7 | 85440 | 1.463924433 | 6.447777789 | 1.24E−74 | 3.40E−72 |
| 61 | HSPA1B | 3304 | 1.456621834 | 6.52928393 | 5.34E−10 | 3.05E−09 |
| 62 | FCGR2A | 2212 | 1.451480049 | 5.181698415 | 4.46E−17 | 4.93E−16 |
| 63 | PDE8A | 5151 | 1.450036047 | 5.6081043 | 1.75E−28 | 4.08E−27 |
| 64 | CD53 | 963 | 1.448132569 | 5.612529616 | 2.36E−22 | 3.85E−21 |
| 65 | NFIA | 4774 | 1.445520271 | 7.502281392 | 9.41E−99 | 1.07E−95 |
| 66 | OLR1 | 4973 | 1.439657423 | 5.056425174 | 2.88E−14 | 2.50E−13 |
| 67 | GPR34 | 2857 | 1.431174821 | 5.57847909 | 3.31E−22 | 5.29E−21 |
| 68 | GNG5 | 2787 | 1.424324998 | 5.512917188 | 2.93E−46 | 1.75E−44 |
| 69 | CAV1 | 857 | 1.411069872 | 5.651324936 | 2.18E−11 | 1.44E−10 |
| 70 | PLCB2 | 5330 | 1.406764511 | 4.943097886 | 7.63E−20 | 1.05E−18 |
| 71 | SPI1 | 6688 | 1.406476056 | 4.924099137 | 2.86E−19 | 3.80E−18 |
| 72 | P2RY12 | 64805 | 1.40588858 | 6.126591767 | 3.36E−17 | 3.76E−16 |
| 73 | LPCAT2 | 54947 | 1.405433884 | 4.792542778 | 1.54E−19 | 2.10E−18 |
| 74 | AIF1 | 199 | 1.384090935 | 5.381480371 | 4.06E−19 | 5.36E−18 |
| 75 | MAN1C1 | 57134 | 1.381386611 | 5.220214534 | 5.40E−22 | 8.47E−21 |

TABLE 1-continued

Results of the differential gene expression analysis of 1p/19q non-codeleted (n = 127) vs. codeleted (n = 70) IDH-mutated grade II and III gliomas of the TCGA database.

| rank | RefName | EntrezID | logFC | logCPM | PValue | FDR |
|---|---|---|---|---|---|---|
| 76 | ADCY8 | 114 | 1.373021975 | 6.297440731 | 4.39E−16 | 4.49E−15 |
| 77 | C1QA | 712 | 1.372476413 | 7.397761928 | 7.67E−14 | 6.42E−13 |
| 78 | SELPLG | 6404 | 1.370915011 | 5.931871268 | 8.50E−22 | 1.32E−20 |
| 79 | DNALI1 | 7802 | 1.365645383 | 5.05260693 | 1.43E−54 | 1.41E−52 |
| 80 | RGS10 | 6001 | 1.363050062 | 5.049287168 | 2.22E−24 | 4.13E−23 |
| 81 | S100A10 | 6281 | 1.360430768 | 6.029972423 | 4.89E−17 | 5.37E−16 |
| 82 | MIIP | 60672 | 1.343428625 | 5.566016894 | 8.71E−60 | 1.04E−57 |
| 83 | CNN3 | 1266 | 1.342744823 | 8.82749936 | 2.22E−66 | 3.69E−64 |
| 84 | HLA-DPB1 | 3115 | 1.33497315 | 6.608267135 | 1.82E−08 | 8.84E−08 |
| 85 | ID4 | 3400 | 1.323505297 | 8.879648972 | 1.03E−32 | 3.07E−31 |
| 86 | WLS | 79971 | 1.319553155 | 8.306902135 | 1.18E−62 | 1.69E−60 |
| 87 | EDNRA | 1909 | 1.307539013 | 5.040363319 | 5.71E−15 | 5.33E−14 |
| 88 | FLNC | 2318 | 1.306512492 | 5.43208637 | 2.21E−10 | 1.32E−09 |
| 89 | GFPT2 | 9945 | 1.298460292 | 5.796451954 | 2.90E−18 | 3.53E−17 |
| 90 | HLA-DPA1 | 3113 | 1.295844838 | 7.505357274 | 5.02E−08 | 2.30E−07 |
| 91 | INPP5D | 3635 | 1.294467856 | 5.570641812 | 2.32E−26 | 4.84E−25 |
| 92 | FBXO32 | 114907 | 1.292438089 | 5.047281198 | 1.47E−16 | 1.57E−15 |
| 93 | SYNM | 23336 | 1.291598562 | 7.468172518 | 1.90E−25 | 3.76E−24 |
| 94 | TNC | 3371 | 1.29152412 | 7.786280109 | 5.45E−18 | 6.50E−17 |
| 95 | RPS6KA1 | 6195 | 1.286720431 | 4.848815021 | 2.60E−20 | 3.71E−19 |
| 96 | HLA-DMA | 3108 | 1.282970693 | 5.482937543 | 5.36E−12 | 3.75E−11 |
| 97 | GJA1 | 2697 | 1.28164256 | 9.216772983 | 6.67E−15 | 6.18E−14 |
| 98 | UCP2 | 7351 | 1.280644604 | 5.520374729 | 5.14E−16 | 5.23E−15 |
| 99 | C1R | 715 | 1.276459501 | 6.458331089 | 1.27E−08 | 6.24E−08 |
| 100 | HSPA1A | 3303 | 1.275991117 | 9.165522546 | 1.85E−09 | 9.96E−09 |
| 101 | LCP1 | 3936 | 1.26922555 | 5.6478656 | 3.79E−17 | 4.22E−16 |
| 102 | SIGLEC10 | 89790 | 1.266105036 | 4.920495708 | 1.26E−16 | 1.36E−15 |
| 103 | TREM2 | 54209 | 1.263549936 | 5.747746789 | 7.88E−15 | 7.22E−14 |
| 104 | TGFB1 | 7040 | 1.258558824 | 5.53700818 | 6.41E−32 | 1.84E−30 |
| 105 | SIGLEC8 | 27181 | 1.253123216 | 4.945980775 | 2.37E−15 | 2.28E−14 |
| 106 | SYT6 | 148281 | 1.247415128 | 4.967422719 | 1.50E−33 | 4.74E−32 |
| 107 | TYROBP | 7305 | 1.245716035 | 5.71517157 | 1.18E−15 | 1.17E−14 |
| 108 | RGS1 | 5996 | 1.242719545 | 5.869121057 | 4.28E−08 | 1.91E−07 |
| 109 | LOC154822 | 154822 | 1.241730615 | 6.665914308 | 1.02E−05 | 3.28E−05 |
| 110 | TNFRSF1B | 7133 | 1.220781026 | 5.502544608 | 3.93E−21 | 5.83E−20 |
| 111 | RNASET2 | 8635 | 1.216174063 | 6.121746749 | 2.29E−20 | 3.28E−19 |
| 112 | TSPO | 706 | 1.212688574 | 5.256558212 | 8.02E−19 | 1.03E−17 |
| 113 | CSF1 | 1435 | 1.205318162 | 6.132168703 | 4.76E−30 | 1.22E−28 |
| 114 | LTBP4 | 8425 | 1.203362257 | 6.528369208 | 3.50E−16 | 3.63E−15 |
| 115 | ARHGEF10L | 55160 | 1.201149034 | 7.200735804 | 1.43E−47 | 9.00E−46 |
| 116 | APOC2 | 344 | 1.199606721 | 5.102746429 | 1.04E−09 | 5.74E−09 |
| 117 | IFI6 | 2537 | 1.199248737 | 7.036339321 | 4.28E−07 | 1.70E−06 |
| 118 | FAM182B | 728882 | 1.189863553 | 4.796448327 | 5.92E−17 | 6.47E−16 |
| 119 | ALDH4A1 | 8659 | 1.188636618 | 7.234081076 | 7.91E−29 | 1.89E−27 |
| 120 | HLA-DRB1 | 3123 | 1.180347223 | 6.841847705 | 1.35E−06 | 4.95E−06 |
| 121 | HDAC1 | 3065 | 1.179596836 | 5.569657503 | 7.51E−65 | 1.20E−62 |
| 122 | STAB1 | 23166 | 1.179515083 | 6.383436541 | 1.67E−13 | 1.36E−12 |
| 123 | PLEKHA5 | 54477 | 1.174315211 | 5.618044861 | 1.41E−26 | 2.95E−25 |
| 124 | ARPC1B | 10095 | 1.171000905 | 5.841256695 | 5.28E−19 | 6.89E−18 |
| 125 | SALL3 | 27164 | 1.168380174 | 4.755374966 | 5.88E−12 | 4.10E−11 |
| 126 | KANK2 | 25959 | 1.159675777 | 5.738947371 | 1.70E−26 | 3.55E−25 |
| 127 | CEBPA | 1050 | 1.15925427 | 4.938126794 | 1.08E−14 | 9.77E−14 |
| 128 | RHOC | 389 | 1.155665802 | 7.674252842 | 1.77E−44 | 9.88E−43 |
| 129 | GPC4 | 2239 | 1.152285335 | 5.309801091 | 2.62E−24 | 4.81E−23 |
| 130 | AHCYL1 | 10768 | 1.145470922 | 9.916508188 | 1.02E−22 | 1.71E−21 |
| 131 | SLA | 6503 | 1.143292366 | 4.936804392 | 3.66E−13 | 2.89E−12 |
| 132 | MAGI3 | 260425 | 1.143205507 | 5.10672159 | 1.38E−39 | 5.94E−38 |
| 133 | EGR1 | 1958 | 1.14127499 | 7.759166504 | 1.68E−06 | 6.11E−06 |
| 134 | LGALS9 | 3965 | 1.140692257 | 5.666058686 | 7.97E−14 | 6.67E−13 |
| 135 | MS4A7 | 58475 | 1.129313471 | 5.037963562 | 4.86E−13 | 3.80E−12 |
| 136 | C1orf226 | 400793 | 1.124015868 | 5.313447264 | 2.61E−24 | 4.81E−23 |
| 137 | CD4 | 920 | 1.123318601 | 6.084007614 | 2.69E−16 | 2.80E−15 |
| 138 | CCNL2 | 81669 | 1.122740767 | 6.721679128 | 1.19E−20 | 1.72E−19 |
| 139 | HK2 | 3099 | 1.12102438 | 5.231452533 | 3.53E−19 | 4.67E−18 |
| 140 | CORO1A | 11151 | 1.120986513 | 6.200660651 | 1.69E−21 | 2.56E−20 |
| 141 | FLNA | 2316 | 1.12051009 | 8.534935934 | 3.17E−22 | 5.09E−21 |
| 142 | S100A11 | 6282 | 1.118165273 | 5.155923255 | 1.55E−11 | 1.03E−10 |
| 143 | SNX7 | 51375 | 1.116645722 | 4.635718074 | 9.06E−54 | 8.02E−52 |
| 144 | CD68 | 968 | 1.112994781 | 6.78496215 | 7.81E−13 | 5.99E−12 |
| 145 | NOTCH2 | 4853 | 1.112984889 | 8.085766502 | 6.83E−37 | 2.64E−35 |
| 146 | GALNT9 | 50614 | 1.108987557 | 4.926120189 | 1.85E−08 | 8.97E−08 |
| 147 | RHPN2 | 85415 | 1.107624987 | 5.091479994 | 2.72E−19 | 3.62E−18 |
| 148 | CYBA | 1535 | 1.106545276 | 5.299335901 | 1.63E−13 | 1.33E−12 |
| 149 | STK40 | 83931 | 1.101992516 | 5.736398956 | 3.02E−40 | 1.37E−38 |
| 150 | MMP14 | 4323 | 1.100018901 | 6.003942247 | 2.26E−12 | 1.65E−11 |

TABLE 1-continued

Results of the differential gene expression analysis of 1p/19q non-codeleted (n = 127) vs. codeleted (n = 70) IDH-mutated grade II and III gliomas of the TCGA database.

| rank | RefName | EntrezID | logFC | logCPM | PValue | FDR |
|---|---|---|---|---|---|---|
| 151 | CD99 | 4267 | 1.09778675 | 8.043402556 | 8.54E−10 | 4.76E−09 |
| 152 | ANXA2 | 302 | 1.093659002 | 5.719818237 | 2.67E−10 | 1.58E−09 |
| 153 | ARHGDIB | 397 | 1.093274317 | 6.360972645 | 1.51E−18 | 1.88E−17 |
| 154 | CACHD1 | 57685 | 1.092982481 | 5.697078868 | 2.58E−48 | 1.70E−46 |
| 155 | AGTRAP | 57085 | 1.090324988 | 4.693591583 | 1.72E−29 | 4.32E−28 |
| 156 | CTSS | 1520 | 1.089660226 | 5.521981054 | 3.15E−11 | 2.04E−10 |
| 157 | OLFML3 | 56944 | 1.089123166 | 5.216619981 | 7.80E−16 | 7.81E−15 |
| 158 | MOV10 | 4343 | 1.08466363 | 4.790612983 | 5.37E−39 | 2.26E−37 |
| 159 | CD44 | 960 | 1.082819924 | 8.038460419 | 2.43E−09 | 1.29E−08 |
| 160 | VCL | 7414 | 1.076532776 | 6.387839252 | 3.45E−26 | 7.17E−25 |
| 161 | SERPINA3 | 12 | 1.072314577 | 7.850905231 | 5.61E−05 | 0.000160377 |
| 162 | IL13RA1 | 3597 | 1.069428863 | 6.106343293 | 1.52E−20 | 2.20E−19 |
| 163 | SHKBP1 | 92799 | 1.067887266 | 4.74358676 | 1.03E−35 | 3.69E−34 |
| 164 | UBA2 | 10054 | 1.06782487 | 7.198042205 | 7.69E−86 | 4.09E−83 |
| 165 | JUN | 3725 | 1.067105861 | 7.68195442 | 5.46E−16 | 5.55E−15 |
| 166 | YAP1 | 10413 | 1.064613856 | 5.827207368 | 3.31E−20 | 4.64E−19 |
| 167 | NECAP2 | 55707 | 1.063382333 | 6.265635605 | 5.68E−49 | 3.97E−47 |
| 168 | ST3GAL6 | 10402 | 1.062775422 | 4.668074748 | 1.98E−19 | 2.68E−18 |
| 169 | EPB41 | 2035 | 1.06077099 | 5.600606976 | 1.29E−39 | 5.60E−38 |
| 170 | CROCC | 9696 | 1.058351343 | 4.812082884 | 3.33E−24 | 6.07E−23 |
| 171 | CSRP2 | 1466 | 1.05830171 | 6.706140867 | 9.95E−11 | 6.16E−10 |
| 172 | EDNRB | 1910 | 1.054702735 | 9.137094064 | 2.42E−12 | 1.76E−11 |
| 173 | MAD2L2 | 10459 | 1.053946574 | 5.566454219 | 3.36E−50 | 2.45E−48 |
| 174 | PPAP2B | 8613 | 1.046178147 | 8.184546101 | 1.14E−34 | 3.83E−33 |
| 175 | FOLR2 | 2350 | 1.039193345 | 5.150239955 | 3.19E−12 | 2.29E−11 |
| 176 | RYR1 | 6261 | 1.03848531 | 5.821766457 | 2.32E−11 | 1.52E−10 |
| 177 | LHFPL2 | 10184 | 1.033866849 | 5.776809269 | 4.08E−19 | 5.38E−18 |
| 178 | AK2 | 204 | 1.03357355 | 6.002873286 | 8.64E−59 | 9.57E−57 |
| 179 | FARP1 | 10160 | 1.028753099 | 6.898877236 | 3.15E−33 | 9.67E−32 |
| 180 | CTSC | 1075 | 1.028579869 | 5.320651078 | 3.47E−12 | 2.48E−11 |
| 181 | RIPK2 | 8767 | 1.027939411 | 5.115649168 | 4.08E−40 | 1.82E−38 |
| 182 | YBX1 | 4904 | 1.027718153 | 8.529634548 | 1.03E−50 | 7.71E−49 |
| 183 | WNK2 | 65268 | 1.027388184 | 5.866253083 | 8.66E−11 | 5.37E−10 |
| 184 | RNF182 | 221687 | 1.02266399 | 5.219111253 | 7.98E−18 | 9.36E−17 |
| 185 | SIPA1 | 6494 | 1.022632863 | 5.222123587 | 3.48E−22 | 5.55E−21 |
| 186 | SOD2 | 6648 | 1.021191871 | 8.056939197 | 1.25E−08 | 6.16E−08 |
| 187 | DENND3 | 22898 | 1.016200266 | 5.292368802 | 8.50E−16 | 8.51E−15 |
| 188 | STK17B | 9262 | 1.015565193 | 5.769251844 | 2.10E−20 | 3.02E−19 |
| 189 | FN1 | 2335 | 1.013079355 | 9.000424006 | 6.27E−08 | 2.84E−07 |
| 190 | BLVRB | 645 | 1.012669954 | 4.822857444 | 2.73E−21 | 4.09E−20 |
| 191 | NADK | 65220 | 1.011924484 | 5.688340585 | 1.03E−108 | 1.65E−105 |
| 192 | PLEKHG2 | 64857 | 0.999950046 | 5.135266606 | 2.91E−30 | 7.53E−29 |
| 193 | SPP1 | 6696 | 0.998225162 | 9.427328702 | 6.67E−06 | 2.21E−05 |
| 194 | ZFP36 | 7538 | 0.990964969 | 6.410376311 | 9.67E−08 | 4.24E−07 |
| 195 | STON1 | 11037 | 0.990262179 | 5.964947332 | 5.60E−16 | 5.68E−15 |
| 196 | GNAI3 | 2773 | 0.985422021 | 6.613155421 | 2.46E−92 | 1.96E−89 |
| 197 | PTPRF | 5792 | 0.983504274 | 7.742019508 | 8.27E−35 | 2.79E−33 |
| 198 | ZNF436 | 80818 | 0.983275659 | 5.430861964 | 5.84E−37 | 2.27E−35 |
| 199 | ABI3BP | 25890 | 0.980880012 | 5.555021947 | 1.03E−07 | 4.49E−07 |
| 200 | LYN | 4067 | 0.979196476 | 4.961949385 | 1.00E−13 | 8.29E−13 |
| 201 | CSMD2 | 114784 | 0.977856052 | 5.316357232 | 1.11E−21 | 1.71E−20 |
| 202 | FIBIN | 387758 | 0.977016036 | 6.512956156 | 2.86E−08 | 1.35E−07 |
| 203 | S100A6 | 6277 | 0.97532527 | 7.422609769 | 6.47E−11 | 4.06E−10 |
| 204 | BHLHE41 | 79365 | 0.974183487 | 6.846250313 | 6.75E−15 | 6.24E−14 |
| 205 | MAF | 4094 | 0.971780965 | 5.886574955 | 9.85E−22 | 1.52E−20 |
| 206 | MKNK1 | 8569 | 0.971024869 | 4.733990932 | 6.44E−26 | 1.30E−24 |
| 207 | KIAA2013 | 90231 | 0.96679554 | 5.866779227 | 3.19E−71 | 7.28E−69 |
| 208 | FOS | 2353 | 0.965843544 | 7.944287696 | 1.04E−05 | 3.35E−05 |
| 209 | OSBPL9 | 114883 | 0.965268584 | 5.849846913 | 4.51E−43 | 2.37E−41 |
| 210 | KDM1A | 23028 | 0.963491518 | 6.839537646 | 3.20E−61 | 4.11E−59 |
| 211 | STK38L | 23012 | 0.963133162 | 6.173925852 | 2.18E−29 | 5.44E−28 |
| 212 | WASF2 | 10163 | 0.96284773 | 7.481519421 | 2.70E−54 | 2.50E−52 |
| 213 | RHPN1 | 114822 | 0.962547484 | 5.253302035 | 8.21E−13 | 6.26E−12 |
| 214 | SFRS4 | 6429 | 0.96233441 | 6.650410903 | 1.39E−124 | 5.53E−121 |
| 215 | C1orf86 | 199990 | 0.960156025 | 4.705414297 | 2.70E−30 | 7.04E−29 |
| 216 | HMHA1 | 23526 | 0.957484656 | 5.087038801 | 2.23E−19 | 2.99E−18 |
| 217 | GNL2 | 29889 | 0.948127529 | 5.263393486 | 1.74E−66 | 2.95E−64 |
| 218 | FBXO42 | 54455 | 0.947648483 | 4.926353651 | 1.12E−116 | 2.98E−113 |
| 219 | PHF13 | 148479 | 0.944904411 | 4.794197877 | 2.20E−83 | 9.21E−81 |
| 220 | RCC2 | 55920 | 0.944565207 | 6.963413216 | 1.34E−54 | 1.34E−52 |
| 221 | SLC25A33 | 84275 | 0.942397222 | 4.774910691 | 1.45E−29 | 3.66E−28 |
| 222 | TMEM167B | 56900 | 0.930513081 | 6.164776155 | 5.85E−109 | 1.17E−105 |
| 223 | KCND2 | 3751 | 0.929362475 | 6.758384048 | 1.16E−15 | 1.15E−14 |
| 224 | SLC4A2 | 6522 | 0.92776922 | 6.541509086 | 3.76E−36 | 1.42E−34 |
| 225 | BST2 | 684 | 0.927357334 | 5.30761462 | 4.39E−09 | 2.27E−08 |

TABLE 1-continued

Results of the differential gene expression analysis of 1p/19q non-codeleted (n = 127) vs. codeleted (n = 70) IDH-mutated grade II and III gliomas of the TCGA database.

| rank | RefName | EntrezID | logFC | logCPM | PValue | FDR |
| --- | --- | --- | --- | --- | --- | --- |
| 226 | CAPZB | 832 | 0.92532523 | 7.864139987 | 7.25E−87 | 4.13E−84 |
| 227 | KIAA1274 | 27143 | 0.921285062 | 6.378841605 | 3.14E−22 | 5.06E−21 |
| 228 | PRDX1 | 5052 | 0.921271726 | 8.179273311 | 8.52E−15 | 7.75E−14 |
| 229 | DCTD | 1635 | 0.918696703 | 5.080953173 | 1.10E−18 | 1.40E−17 |
| 230 | IFI16 | 3428 | 0.918030401 | 6.641939564 | 2.08E−16 | 2.18E−15 |
| 231 | IGSF3 | 3321 | 0.914153519 | 5.624840491 | 7.41E−07 | 2.83E−06 |
| 232 | NUMBL | 9253 | 0.910793461 | 5.563505085 | 1.85E−22 | 3.04E−21 |
| 233 | CRYAB | 1410 | 0.907916686 | 11.65684749 | 4.11E−09 | 2.13E−08 |
| 234 | PAM | 5066 | 0.904691443 | 7.640318595 | 5.35E−20 | 7.49E−19 |
| 235 | PHACTR4 | 65979 | 0.904650142 | 5.602723012 | 1.89E−72 | 4.70E−70 |
| 236 | C10orf54 | 64115 | 0.903890854 | 6.901740399 | 4.83E−19 | 6.31E−18 |
| 237 | VPS13D | 55187 | 0.900392289 | 8.059588546 | 7.45E−20 | 1.03E−18 |
| 238 | IGSF1 | 3547 | 0.900279594 | 5.175426981 | 0.000134624 | 0.000361764 |
| 239 | TTYH1 | 57348 | 0.900091328 | 9.256392897 | 1.74E−16 | 1.84E−15 |
| 240 | TXLNA | 200081 | 0.899885188 | 6.106226664 | 1.55E−63 | 2.38E−61 |
| 241 | BAIAP3 | 8938 | 0.898737755 | 6.293845485 | 6.73E−09 | 3.42E−08 |
| 242 | PDZRN3 | 23024 | 0.894959297 | 5.527484307 | 2.36E−23 | 4.09E−22 |
| 243 | SCP2 | 6342 | 0.894758315 | 7.07134831 | 6.79E−69 | 1.32E−66 |
| 244 | TXNDC12 | 51060 | 0.891764675 | 6.083433068 | 1.60E−76 | 4.56E−74 |
| 245 | PKN2 | 5586 | 0.890477826 | 5.684510485 | 8.37E−67 | 1.45E−64 |
| 246 | CCDC103 | 388389 | 0.887964961 | 4.994178967 | 2.72E−10 | 1.61E−09 |
| 247 | CD302 | 9936 | 0.887165151 | 4.964477684 | 1.20E−16 | 1.30E−15 |
| 248 | IQGAP1 | 8826 | 0.885504147 | 6.262377041 | 1.25E−18 | 1.58E−17 |
| 249 | ROBO2 | 6092 | 0.883653821 | 4.920009463 | 5.75E−09 | 2.94E−08 |
| 250 | FAM69A | 388650 | 0.882736622 | 5.878303437 | 7.50E−26 | 1.51E−24 | logFC, log fold-change; logCPM, log counts per million; FDR, false-discovery rate adjusted p value.

Figure 9:
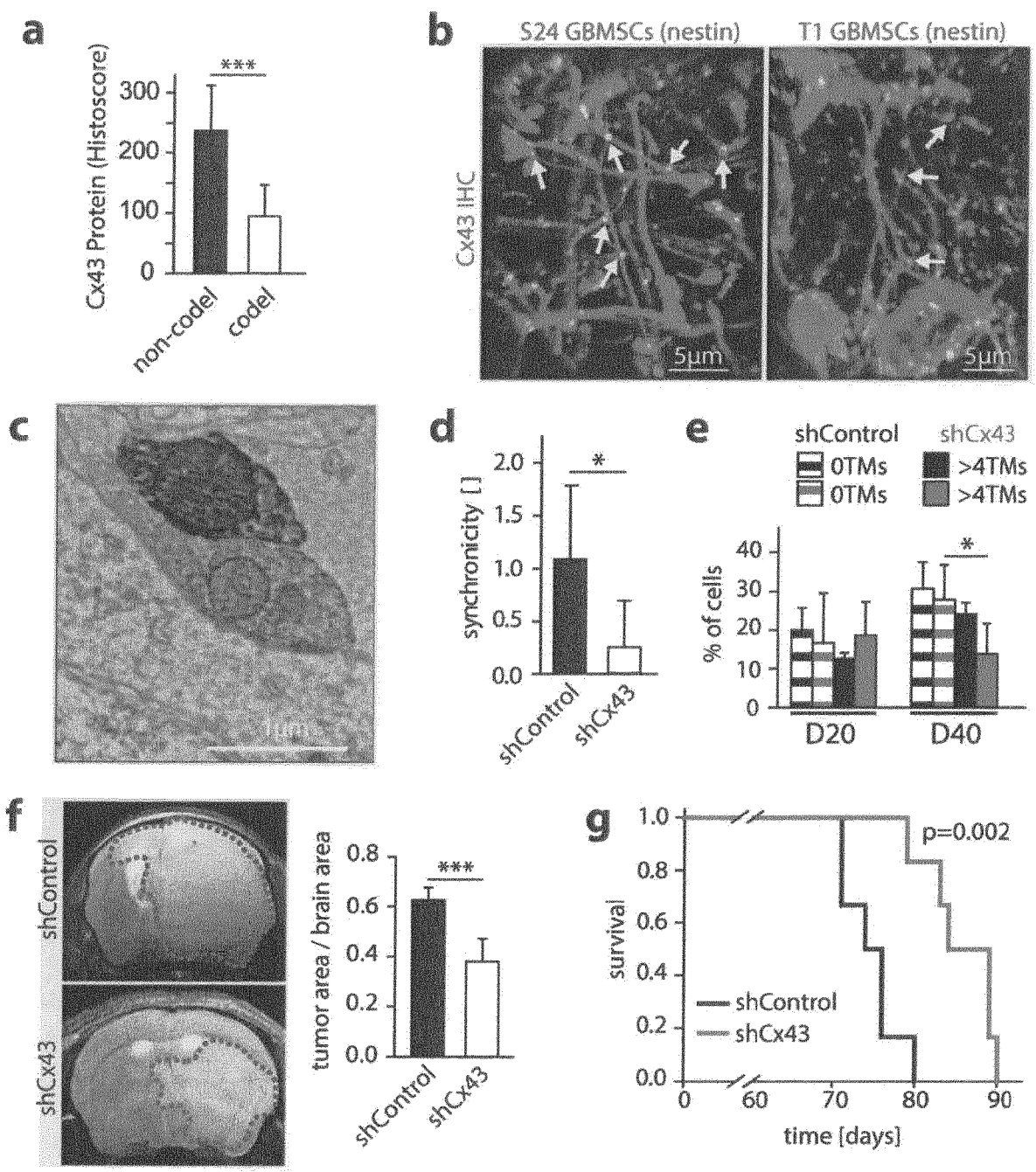

Of the 20 connexins for which reads were mapped, only connexin 43 (Cx43, GJA1) was differentially expressed, and found to be among the top 100 upregulated genes in 1p/19q non-codeleted tumors. Cx43 is a major connexin protein, and also highly expressed in astrocytes, connecting them to functional and resistant multicellular networks. In gliomas, a strong relationship between retention of 1p/19q and Cx43 protein expression was confirmed in patient tumor tissue (FIG. 9a), and also in the primary glioma cell lines (FIG. 8h). Confocal microscopy revealed punctate Cx43 immunoreactivity particularly at the TMs of astrocytoma cells (FIG. 9b), which was not seen for other connexins like Cx31 or Cx37 (located on chromosome 1p), or Cx26 (expressed in normal astrocytes; FIG. 8i). Remarkably, Cx43 immunoreactivity frequently located at the very place where two different TMs crossed each other (FIG. 9b). Contact sites of individual TMs with direct membrane-membrane contact were also detected with 3D SEM (FIG. 9c). Further analysis of our ICW datasets revealed that calcium waves can propagate via those crossings from one TM to another (FIG. 7a, red arrow). Taken together, TM-associated Cx43 gap junctions, including those between different TMs at their frequent crossing sites, create a dense network of intercellular communication in astrocytomas.

To investigate the functional role of the Cx43 gap junction protein in astrocytoma progression, a stable shRNA knockdown of Cx43 was performed in GBMSCs. This significantly reduced the synchronicity of ICWs in vivo (FIG. 9d), and also the proportion of astrocytoma cells with multiple TMs at later time points (FIG. 9e), which suggests a role for Cx43 gap junction-mediated communication in long-term stabilization of TMs. In accordance with the proposed role of functional TMs for tumor progression, Cx43 deficiency resulted in reduced tumor size in MRI (FIG. 9f), and improved survival (FIG. 9g).

Example 5

A Self-Repairing and Resistant Network

To understand the role of TMs for tumor integrity and resistance, advantage was taken of the fact that individual astrocytoma cells showed a striking heterogeneity throughout tumor progression: while the proportion of TM-connected cells increased over time, a substantial part of astrocytoma cells remained unconnected (FIG. 1h). This heterogeneity made it possible to study the differential biological behavior of TM-connected vs. TM-unconnected tumor cells. To investigate the role of TMs in damage repair in vivo, selective ablation of single astrocytoma cells was performed by applying a fatal laser dose to a fraction of their nuclear volume (1 µm$^3$). If the ablated astrocytoma cell was a prior member of the TM-connected network, new TMs were extended towards the dead cell, stabilized, and within a few days a new nucleus advanced via those TMs to the very place of the prior cell (FIG. 10a, n=8 reconstitution events in 8 photodamaged tumor cells from n=3 animals). If a non-TM connected cell was ablated, such repair mechanism was only infrequently observed (2/8 events in n=3 animals; p<0.01, Fisher's exact Test). Sublethal photon damage to a larger volume (0.5-1×10$^6$ µm$^3$) consisting of 6-10 astrocytoma cells and normal brain parenchyma resulted in marked increase in tumor cell content within 2 days (FIG. 10b). This was due to a rapid extension of TMs into that damaged area, followed by increase in tumor cell density (FIG. 10c).

Next it was investigated whether TM-connected tumor cell networks were also resistant against the cytotoxic effects of radiation therapy, which is a standard treatment of gliomas. While TM-connected cells were largely protected from cell death, unconnected tumor cells died in relevant numbers after radiotherapy (FIG. 10d, FIG. 11a,b). Furthermore, TM-connected astrocytoma cells increased both their TM number (FIG. 10e), and their calcium communication (FIG.

10f,g) as a reaction to radiotherapy. Concordantly, Cx43 knockdown reduced the radioprotective effect of TM interconnections, while non-TM connected astrocytoma cells regressed like in control tumors (FIG. 10h). This speaks for a role of functional Cx43 gap junctions in TM-mediated radioresistance.

To explore potential mechanisms of TM-mediated protection from cytotoxicity, basal intracellular calcium levels were measured in astrocytoma cells before and during radiotherapy, using a ratiometric calcium indicator. Basal calcium levels were very homogeneous in non-irradiated cells, and also in TM-connected cells during radiotherapy, while unconnected cells developed a high variability of their intracellular calcium levels during irradiation (FIG. 11c-f). Increases of intracellular calcium levels are required for radiotherapy-induced cytotoxicity34, and even small calcium increases are involved in intrinsic apoptotic cell death in glioma cells. One can speculate that intercellular TMs can serve as a means for an individual cell to distribute small molecules like calcium within the larger network, achieving nonlethal levels.

Together this argues for an important role of TM-mediated intercellular communication as means of primary and adaptive resistance to radiotherapy. In summary, these results support a role for TMs in astrocytoma cell resistance against environmental stress and in communication of adverse events, ultimately leading to a coordinated survival and, if necessary, damage repair.

Example 6

GAP43: A Driver of TM Formation

Figure 12:
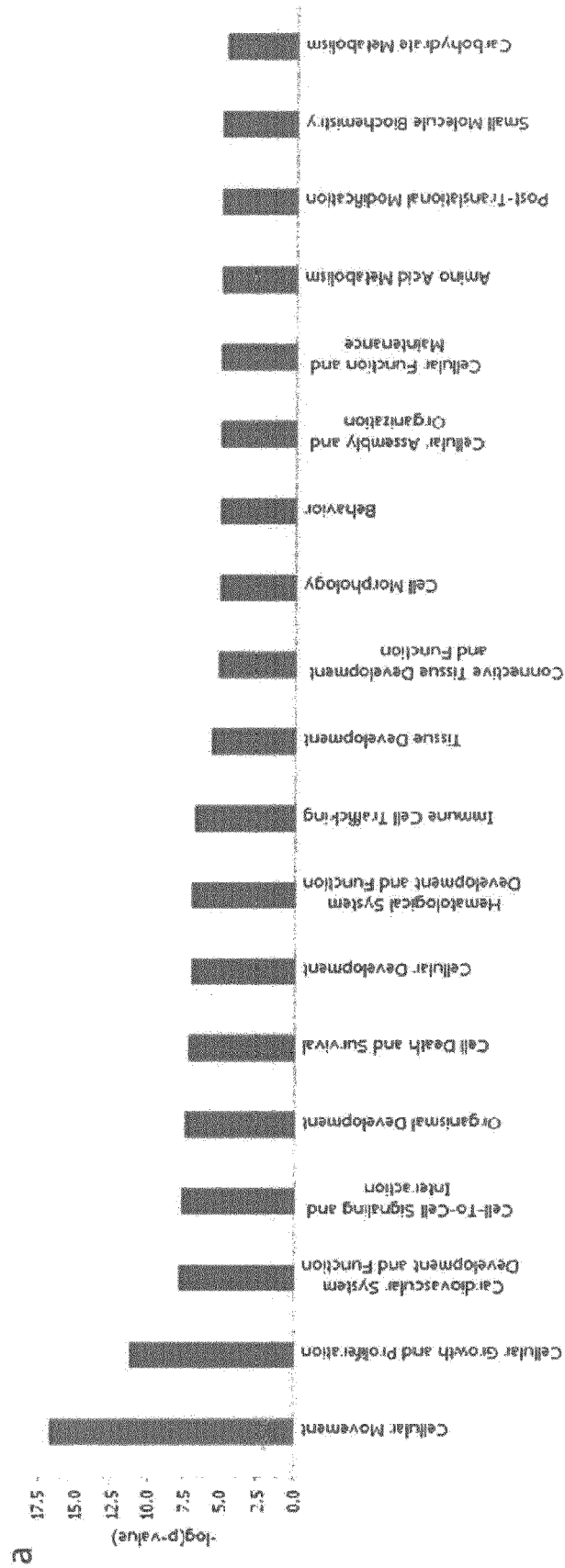
Figure 12:
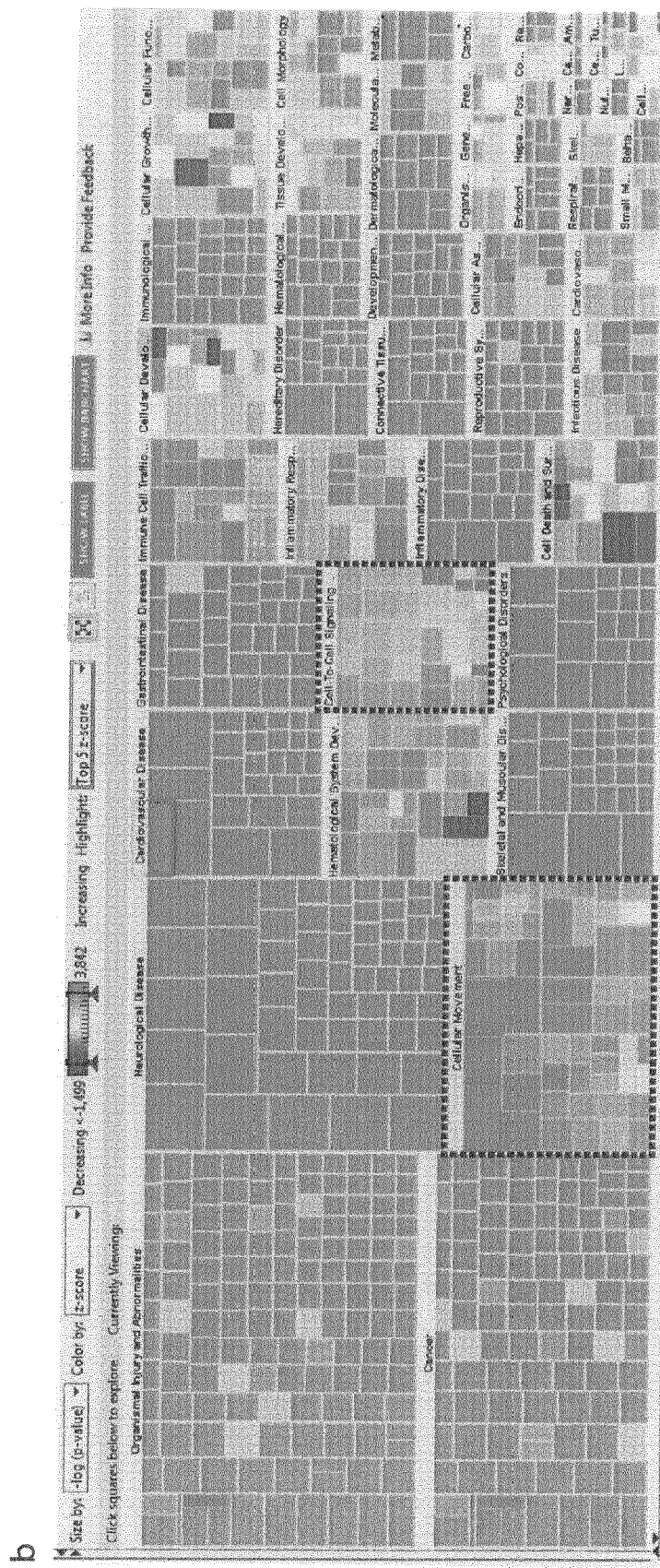
Figure 12C:
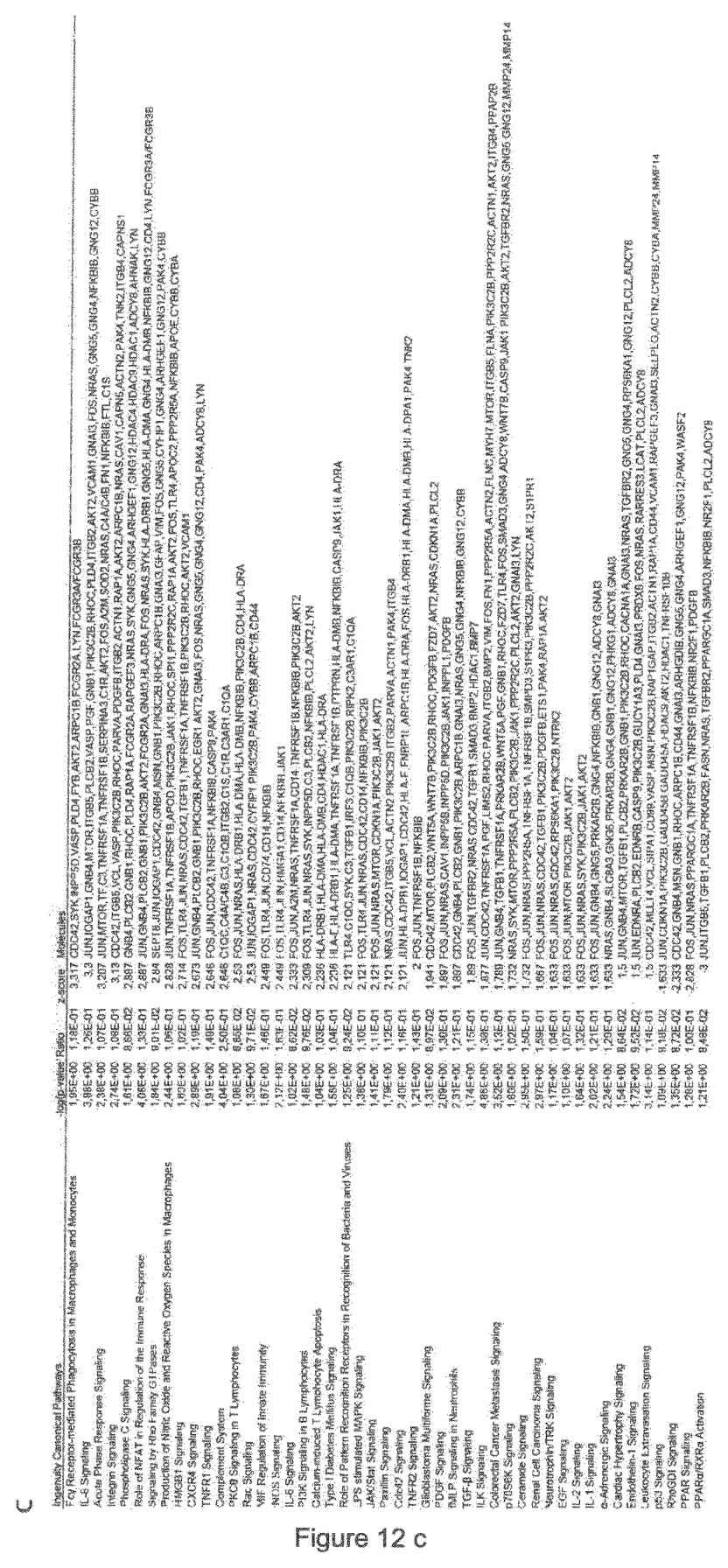

Next it was sought to identify the crucial molecular pathways that drive the formation of TMs—to better understand their nature, and to substantiate their role for tumor progression and resistance. For this purpose, the in silico dataset of human 1p/19q codeleted vs. non-codeleted gliomas (Table 1) was first analyzed by using Ingenuity Pathway Analysis. Here, pathways that were prominently activated in 1p/19q non-codeleted gliomas included "cellular movement", and "cell-to-cell signaling and interaction", supporting the proposed function of TMs in these tumors (FIG. 12a,b). Intriguingly, many pathways were found involved in the outgrowth of neurites, and neurite-like membrane protrusions to be more activated in 1p/19q non-codeleted gliomas, including integrin, phospholipase C, Rho family GTPases, HMGB1, and also the prototypical neurotrophin/TRK signaling pathways (FIG. 12c). The latter was confirmed on the protein level in human gliomas, where NGF (located on 1p) and NT-4 (19q) were downregulated in 1p/19q codeleted tumors, and also their respective membrane receptors TrkA and TrkB, which has been described before (FIG. 13a). Together this data indicated that TM formation in tumor cells, and neurite (-like) extensions of nonmalignant cells share not only many morphological, but potentially also molecular features.

When reviewing the literature for known downstream effectors particularly relevant for the formation of neurites and neurite-like membrane protrusions, the growth-associated protein GAP-43 came into focus. GAP-43 is highly expressed in axonal growth cones, induced by neurotrophin receptor signaling, and drives neuronal progenitor cell migration. Remarkably, GAP-43 overexpression is sufficient for the outgrowth of membrane tubes in neuronal and even in non-neuronal cells. Indeed, GAP-43 was significantly higher expressed in 1p/19q non-codeleted human gliomas (FIG. 14a) and primary cell lines (FIG. 14a, FIG. 13b) when compared with 1p/19q codeleted ones. Of note, GAP-43 preferentially localized to the cone-like and nestin-negative tips of sprouting TMs (FIG. 14c), similar to its known enrichment in the nerve growth cone.

To interfere with TM formation during astrocytoma progression, GBMSCs with a genetic knockdown of GAP-43 were engineered. While in vitro viability of these cells was not affected, their TMs in vivo were structurally abnormal, with reduced branchings (FIG. 14d). This was associated with an impaired dissemination of tumor cells (FIG. 14e, FIG. 13c), resulting from both their decreased invasion velocity (FIG. 14f), and proliferation capacity (FIG. 14g) in the mouse brain. Importantly, intercellular TM connections (FIG. 14h), and ICWs (FIG. 14i) were reduced in GAP-43 deficient tumors, which was accompanied by a selective reduction of Cx43 gap junction protein expression (FIG. 13d). These deficiencies in TM-mediated features of tumor progression lead to a marked reduction of tumor size in the mouse brain (FIG. 14j), and to an improved survival of the animals (FIG. 14k). When radiotherapy was applied, GAP-43 deficiency resulted in an increased regression of tumor cells, as revealed by repetitive in vivo MPLSM (FIG. 14l). This was confirmed by MRIs 6.0 days after radiation, where no relevant tumor-derived signal changes were detectable in shGap43 tumor bearing animals, while shRNA control tumors were large, causing neurological symptoms in mice (FIG. 14m). Histological analysis at this time point confirmed extensive and diffuse tumor growth involving the contralateral hemisphere in control animals, but only small remnants of proliferation-deficient tumor cells in GAP-43 knockdown tumors (FIG. 14n).

Finally, the GAP-43 protein was overexpressed in 1p/19q codeleted primary oligodendroglioma cells, to achieve protein levels comparable to the 1p/19q non-codeleted GBMSC lines (FIG. 13e) that were cultured under the same stem-like conditions. This lead to a morphological shift to a TM-rich, thus astrocytoma-like phenotype of GAP-43 overexpressing oligodendroglioma cells (FIG. 14o,p). Remarkably, the induction of TM formation in these tumors resulted in an increase in tumor cell invasion into the brain (FIG. 14q), and also an increase in radioresistance (FIG. 14r); both was comparably low in control oligodendrogliomas.

Example 7

Ttyh1: Another Driver of TM Formation

To find more crucial molecular drivers of TM formation and functionality, the gene expression profiles of GBMSCs cultured under stem-like neurosphere conditions (capable of TM-mediated brain colonization within 7 days), and the same GBMSC line cultured under adherent, serum-containing conditions (not capable to form TMs and to colonize the mouse brain within 100 days) were compared. Here, GAP-43 was the most differentially expressed gene, and upregulated in stem-like GBMSCs, confirming the crucial importance of GAP-43 for TM formation and function outlined in Example 6. Moreover, in this screen Ttyh1 was also identified, which has been associated with neuronal development and calcium homeostasis before, to be the third most differentially expressed gene (of >10.000 genes mapped in the screen), again upregulated in stem-like GBMSCs. Interestingly, Ttyh1 is located on chromosome 19q, and protein expression was higher in 1p/19q non-codeleted GBMSCs compared with 1p/19q codeleted oligodendroglioma cells. Accordingly, Ttyh1 mRNA expression was also significantly upregulated in 1p/19q non-codeleted human gliomas, compared to codeleted ones (8-fold, p=1.74×10$^{-16}$, Table 1).

Figure 15:
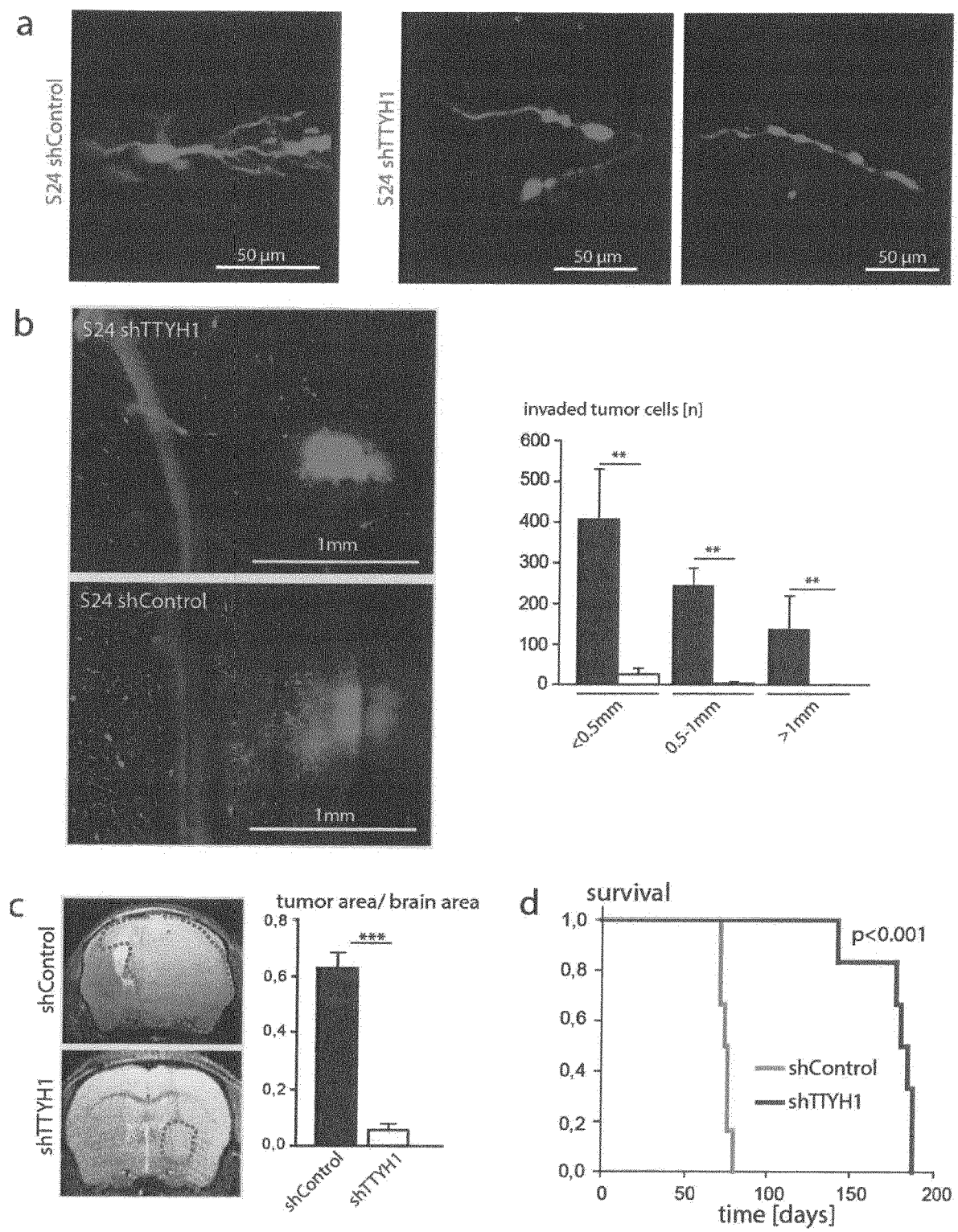

Supporting a central role of Ttyh1 for TM formation, Ttyh1 deficiency resulted in fewer and highly aberrant TMs in astrocytomas (FIG. 15a). Concordantly, brain invasion and proliferation was dramatically reduced when Ttyh1 was knocked down (FIG. 15b), leading to strong inhibition of tumor growth in the mouse brain (FIG. 15c), and ultimately survival times that were more than doubled compared to control animals (FIG. 15d).

Example 8

A Screen to Discover New TM-Relevant Genes

Figure 17:
Figure 17:
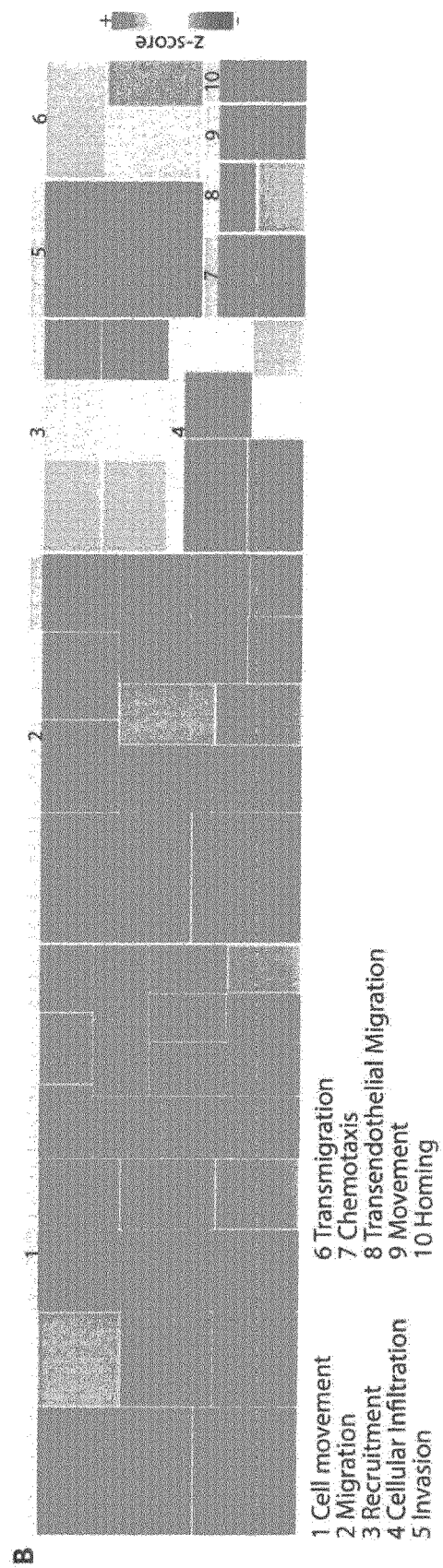

To study the formation and functions of TMs, and to interrogate potential molecular drivers, primary glioblastoma cells from resected brain tumors were kept under non-differentiating, non-adhering, stem-cell like conditions (GBMSCs), and dynamic tumor growth in the mouse brain was followed using repetitive in vivo multi-photon laser scanning microscopy (MPLSM). This technique allows to study brain tumor growth, and the cellular behavior of individual tumor cells, over minutes, hours, days, ultimately several months, deep in the brain of living mice. As early as two weeks after implantation, GBMSCs typically extended multiple TMs in the live mouse brain, and have started to invade it effectively (FIGS. 16 A,C). In contrast, cultivation of the same glioblastoma cells under differentiating, serum-containing conditions for four weeks in vitro resulted in a strong impairment of TM formation in vivo for many weeks, accompanied by massively impaired tumor cell invasion into the mouse brain (FIGS. 16 B-D). Remarkably, when followed for months by intravital microscopy, these TM- and invasion-inhibitory effects were reversible. Around day 100 of slow in vivo growth, gliomas derived from those glioblastoma cells that had been cultured under differentiating conditions in vitro suddenly transformed into TM-proficient and invasive tumors, at this point of time not unsimilar to their rapidly progressing counterparts where glioblastoma cells had been cultured under stem-like conditions in vitro (FIGS. 16 E,F). Considering these findings it was hypothesized that the differentiating in vitro cell culture conditions did not completely eradicate TM-relevant tumor cell subpopulations, but decreased the expression of TM- and invasion-relevant genes in the broad tumor cell population—which is in principle reversible when these cells are later re-educated by the brain microenvironment. Thus it was plausible to perform a gene expression microarray analysis in which glioblastoma cells cultured under both conditions were compared. Ingenuity analysis, and assessment of relative pathway activation revealed that pathways involved in cellular movement were most activated under stem-like conditions compared to serum-containing conditions (FIG. 16 G, FIG. 17). The three genes: growth-associated protein 43 (GAP-43), VGF (no acronym), and tweety homologue 1 (TTYH1) were expressed highest under stem-like conditions when compared to differentiating conditions (Table 2), which was confirmed on the protein level (FIG. 17 A). All three have been associated with CNS (particular neuronal) development before. GAP-43 is the only gene known so far to drive TM formation and function, which supported the potential of the screen to identify TM-relevant genes.

TABLE 2

The 20 most upregulated (A) and 20 most downregulated (B) genes in a RNA microarray comparing S24 GBMSCs cultured under stem-like vs. adherent conditions (see text for details; fold change of mean normalized data for every gene).

| Position | Gene Symbol | Fold change |
| --- | --- | --- |
| (A) | | |
| 1. | GAP43 | 27.59 |
| 2. | VGF | 20.88 |
| 3. | TTYH1 | 14.78 |
| 4. | KCNF1 | 14.08 |
| 5. | OLIG2 | 12.79 |
| 6. | CA9 | 12.29 |
| 7. | OLIG1 | 11.53 |
| 8. | H19 | 10.79 |
| 9. | FXYD6 | 10.07 |
| 10. | HES5 | 9.51 |
| 11. | NDUFA4L2 | 9.36 |
| 12. | C18orf51 | 9.13 |
| 13. | TEK | 9.05 |
| 14. | C1orf61 | 8.32 |
| 15. | C1orf115 | 8.05 |
| 16. | GRIK1 | 8.05 |
| 17. | HEPACAM | 8.05 |
| 18. | FAM181B | 7.39 |
| 19. | CDC20 | 7.06 |
| 20. | ASCL1 | 6.57 |
| 21. | GAP43 | 27.59 |
| (B) | | |
| 31 408. | LUM | 0.06 |
| 31 409. | ID3 | 0.06 |
| 31 410. | CFI | 0.06 |
| 31 411. | SLC47A2 | 0.06 |
| 31 412. | FRZB | 0.06 |
| 31 413. | INHBE | 0.05 |
| 31 414. | DBC1 | 0.05 |
| 31 415. | GLIPR1 | 0.05 |
| 31 416. | VIPR1 | 0.04 |
| 31 417. | IFITM1 | 0.04 |
| 31 418. | IFI27 | 0.04 |
| 31 419. | RGS4 | 0.04 |
| 31 420. | SLPI | 0.04 |
| 31 421. | CCL2 | 0.04 |
| 31 422. | GPNMB | 0.03 |
| 31 423. | AKR1C3 | 0.03 |
| 31 424. | ALDH3A1 | 0.03 |
| 31 425. | PCP4 | 0.03 |
| 31 426. | CXCL14 | 0.02 |
| 31 427. | SRG1 | 0.02 |
| 31 408. | LUM | 0.06 |

Example 9

Two New Candidates for TM Formation

Figure 18:
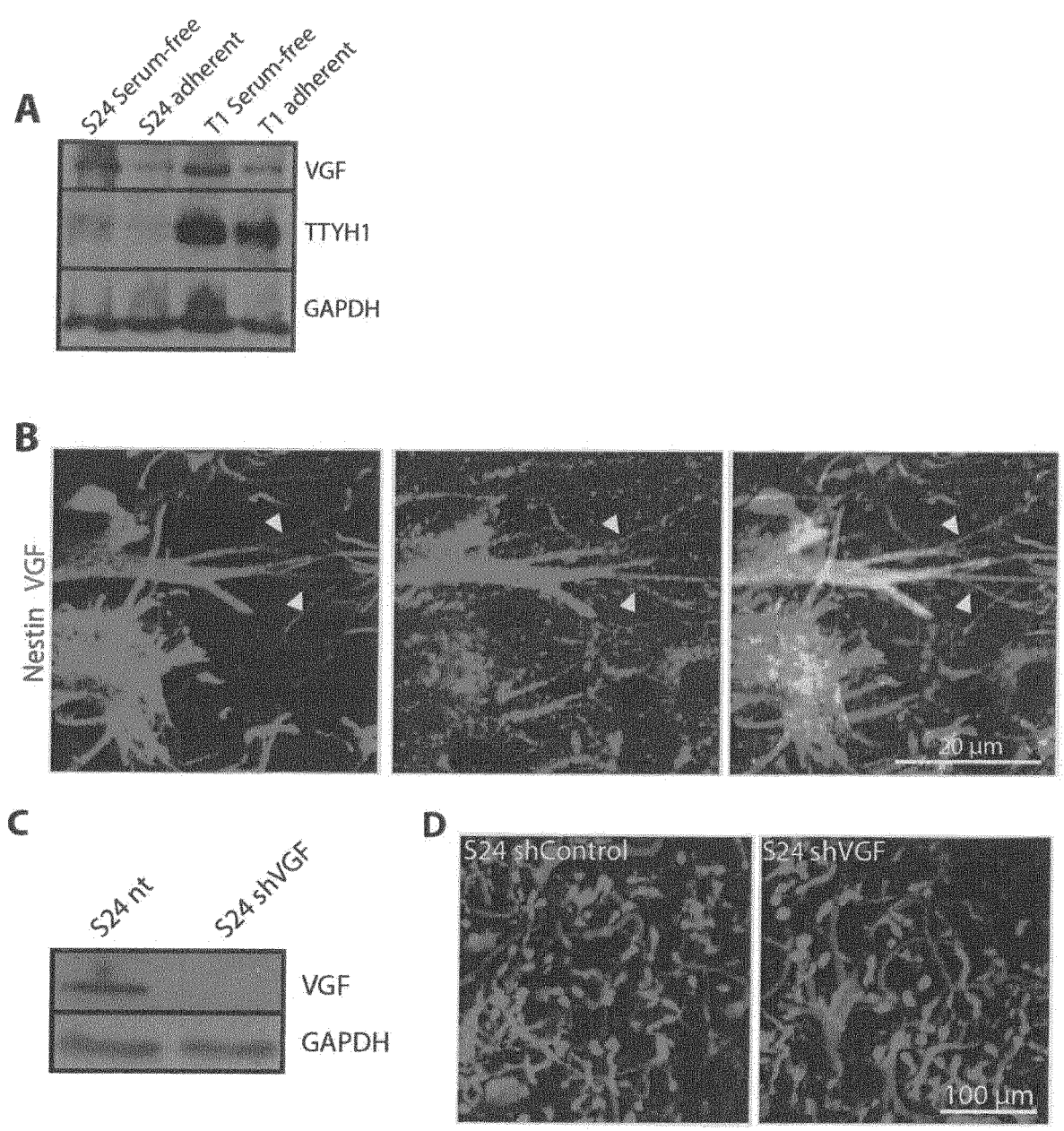

Both VGF and TTYH1 appear to have functions in neurite outgrowth, which made it interesting to investigate whether the second and third scoring hit in the above screen are also involved in the outgrowth of TMs. Although VGF was expressed in GBMSCs, detectable in cell somata as well as in TMs (FIG. 18 B), marked reduction of its gene expression via shRNA (FIG. 18 C) did not result in any differences in growth pattern of gliomas in the brain, including the formation of TMs (FIG. 18 D).

This apparent lack of functional relevance of VGF suggested to proceed to TTYH1. To reveal the subcellular compartments in which TTYH1 was localized, immunocytochemical stainings of GBMSCs were then performed, which demonstrated a preferential localization of TTYH1 as punctuate structures in the cell body, along the membrane of TM-like cellular protrusions, and most prominent at their growth cone-like tips (FIG. 19 A). Furthermore, immunohistochemical stainings of S24 gliomas and human tumor specimen were performed to investigate whether TTYH1 can also be found in TMs in the mouse brain, and in human astrocytoma. Since TTYH1 is expressed to some extent in the normal brain, co-immunofluorescence staining with an anti-TTYH1 antibody together with a tumor cell-specific staining (IDH1-R132H mutation specific antibody for human tumor specimens, anti-human-Nestin for GBMSCs growing in mouse brains) was performed. This allows an unequivocal detection of tumor cells and their filamentous TM protrusions in the filament-rich brain parenchyma. The stainings revealed a heterogeneous expression: while some TMs were strongly TTYH1-positive (arrowheads in FIGS. 19 B and C), many TMs were negative (arrows in FIG. 19 B-D). Of note, some individual tumor cells had both TTYH1-positive and—negative TMs (FIG. 19 C). In human astrocytomas, the vast majority (86.4±5.35%, 6 regions from n=3 patients) of all tumor cell bodies were TTYH1 positive, some of them with clearly TTYH1-positive TMs (FIG. 19 D). Furthermore, colocalization of TTYH1 and integrin α5, most pronounced at the growth cone like tip (FIG. 19 E) was found. Together these findings suggested to investigate the role of Tthy1 for TM formation and function, while questioning the relevance of TTYH1 for all TMs, and/or all TM-related functions.

Example 10

TTYH1 Drives Glioma Cell Invasion and is Crucial for TM Morphology

TTYH1 protein expression in different GBMSCs (FIG. 20 A) correlated with the ability of these cell lines to effectively invade the brain tissue in vivo (FIG. 20 B). This was the first indication that TTYH1 might indeed be of functional relevance for glioma cell invasion.

ShRNA-mediated knockdown of TTYH1 was then performed in the three highly invasive and TTYH1-expressing GBMSCs cell lines S24, T269 and T1, to investigate whether decreased TTYH1 expression results in decreased TM formation and/or function. T1 GBMSCs did not survive the knockdown and died in itro, while shControl-transduced cells survived. In contrast, in S24 and T269 GBMSCs, overall tumor cell viability in vitro was not impaired (data not shown) by the TTYH1 knockdown (FIG. 21 A).

As TTYH1 was both enriched in the invasive tip of TMs, and correlated with the invasion capacity of different GBMSC lines, the invasion capacity of shRNA and shControl-transduced tumor cells in vitro and in vivo was next studied. In vitro, the TTYH1 knockdown led to a reduced invasion in a Collagen I matrix (FIG. 20 C). To investigate if this inhibitory effect was also present in the complex extracellular matrix and microenvironment of the live brain, the three-dimensional migration of individual glioma cells in a growing brain tumor was followed over 24 hours using in vivo MPLSM. This revealed a nearly 4-fold reduction in average cell soma invasion speed in the TTYH1 knockdown cells (FIG. 20 D-F). Glioma cells in control tumors invaded the brain efficiently while dynamically extending TMs (FIG. 20 D), but invasion was reduced to a minimum in the shTTYH1 GBMSCs (FIG. 20 E,F).

After implantation into the mouse brain, striking features of shTTYH1 GBMSCs could be observed: their TMs, which were the leading routes for invasion (FIG. 20 D,E), frequently showed morphological abnormalities resembling chains of beads (FIG. 20 G,H). This phenomenon had been observed after silencing of TTYH1 in hippocampal neurons in vitro before. Remarkably, the morphology of a subpopulation of GBMSCs with multiple TM-connections to other tumor cells was not altered by the shRNA-mediated TTYH1 knockdown, which included their normal appearing TMs in vivo (FIG. 21 B). Although TTYH1 was also located in some TMs of this subpopulation (FIG. 19 C), it had no apparent morphological impact on this subtype of cells and their respective TMs.

Example 11

Cellular Heterogeneity, Invasiveness, and TTYH1

During the analysis of single GBMSC behavior in the live brain, it was noticed that distinct cellular subgroups existed with respect to extent and pattern of TM formation, reproducible in different GBMSC lines (FIG. 22 A, FIG. 21 C). These morphological subtypes could also been found in human astrocytoma specimens (FIG. 22 B), where tumor cells could similarly be subcategorized according to their number of TMs. Four cellular subtypes were most striking: tumor cells with no TMs; 1 TM (unipolar cell); 2 TMs (bipolar cell); and more than 4 TMs (multipolar cell).

The TTYH1 knockdown reduced the relative portion of cells with 1 or 2 TMs, whereas the population with more than 4 TMs was relatively (while not absolutely) increased (FIG. 22 C). To better understand these potential cellular subtypes and to exclude that simply the integration into a densely woven multicellular network itself hinders glioma cell migration, the invasion speed of tumor cell populations with 0 TMs vs. 1 or 2 TMs vs. >4 TMs was analyzed, both for control and shTTYH1 gliomas. This analysis revealed that somata of brain tumor cells with 1 or 2 TMs invaded significantly faster than cells with no TMs, or more than 4 TMs (FIG. 22 D). Video analyses of in vivo cellular movements over 2-3 hours confirmed that control tumor cells with 1-2 TMs were highly dynamic in the live brain, while those with many TMs demonstrated a more resting phenotype. The TTYH1 knockdown reduced the invasion speed of this particularly mobile tumor cell population extending 1-2 TMs (FIG. 22 D). In contrast, the particularly extensive TM-mediated cell-cell interconnections of GBMSCs with more than 4 TMs, plausibly reducing their invasion capacity, was preserved in shTTYH1 tumors when compared to controls (FIG. 21 D). All in all, this data indicates that the reduced invasion capacity of TTYH1 knockdown cells is a combined effect of a proportional reduction of the particularly invasion-competent tumor cell subpopulation with 1 or 2 TMs, and an additional migration deficit of the remaining cells of this subtype.

Example 12

Glioma Growth is Strongly Reduced by TTYH1 Deficiency

To investigate whether the compromised TM morphology and function of shTTYH1 GBMSCs prevented their effective brain colonization, in vivo MPLSM images of large brain regions were next analyzed. Whereas control tumors revealed diffuse infiltration of the whole brain hemisphere with many cells having migrated further than 1 mm from the main tumor (FIG. 23 A), S24 GBMSC TTYH1 knockdown tumors were growing circumscribed at the implantation site, with only few tumor cells that have invaded the brain (FIG. 23 B,E). In T269 GBMSC, a highly invasive glioma cell line showing a very diffuse growth pattern, TTYH1 shRNA knockdown led to a marked reduction of overall tumorigenicity in vivo, with only very few remnant tumor cells detectable in the brain parenchyma after many weeks (FIG. 23 C,D, F).

To investigate the effect of TTYH1 knockdown on gross brain tumor growth, S24 tumors after more than 70 days were analyzed by high-field MRI. The S24 model was chosen because of all three GBMSC lines tested, S24 GBMSCs were least affected by the TTYH1 knockdown, with some preserved capacity to colonize the brain in vivo. A marked reduction of MRI tumor size by the TTYH1 knockdown was evident, with minimal tumor-derived signal changes detectable, and a mean midline shift of only 0.08 (±0.07) mm (FIG. 23 G). At the same time, control tumors were very large and space-occupying, extending over the whole hemisphere (FIG. 23 G), which lead to a significant mass effect with a mean midline shift of 1.35 mm (0.16) mm (p=<0.001), and neurological symptoms. Most importantly, inhibition of glioma progression by TTYH1 downregulation significantly improved the clinical course of the disease, with median survival time massively prolonged (from 75 to 182 days; FIG. 23 H) in this animal model of malignant glioma which in many aspects closely reflects the human disease.

Example 13

A More Interconnected Tumor Cell Network is More Radioresistant

It was finally aimed to clarify whether the TTYH1 knockdown also influenced another crucial TM-mediated function: interconnection of single glioma cells to one large and resistant multicellular network. As the relative fraction of cells bearing multiple TMs was increased in the small TTYH1 knockdown tumors of low cellular density (FIG. 22 C), it was investigated whether this leads to a more interconnected multicellular networks. Indeed, anatomical cell-cell connectivity via TMs was increased in TTYH1 knockdown tumors (FIG. 24 A).

A higher TM interconnectivity has been shown to lead to increased glioma cell resistance against the cytotoxic effects of radiotherapy. In accordance, the sparse and invasion-deficient, but more densely interconnected TTYH1 knockdown gliomas were highly therapy-resistant when treated with radiotherapy, compared to control tumors (FIG. 24. B). A closer analysis revealed that the cytotoxic effects of irradiation were indeed largely restricted to the non-TM-connected tumor cells, while TM-connected GBMSCs were largely protected (FIG. 24 C)—and this was very similar for shTTYH1 and control gliomas (FIG. 24 C). Together this data speaks for functionally undisturbed TM-mediated tumor cell—tumor cell interconnections despite TTYH1 deficiency, preserving the radioresistance of these otherwise growth-deficient tumors.

Discussion:

It has been a long-standing question in neurooncology why codeletion of the chromosomal arms 1 p and 19q in gliomas is associated with a much better disease course, and particularly improved survival after cytotoxic therapy. Likewise, the reason for the aggressive biological behavior of non-codeleted gliomas, which includes primary glioblastomas, is not fully understood. Here it is demonstrated that the ability to form ultra-long and highly functional TMs via proficient GAP-43 and Ttyh1 expression is an important determinant of progression and therapy resistance in 1p/19q non-codeleted brain tumors.

In conclusion, these data support the notion that tumors are complex organs, which has so far been attributed to the supportive contribution of non-malignant cell types, including neurons in brain tumors. The present study adds to this concept by demonstrating that single cancer cells within one tumor communicate and cooperate with each other in a complex but ordered manner that is by itself reminiscent of a functional organ. It has become clear that tumors can hijack programs that are part of normal tissue development. The key finding of this study is that TMs, generated by similar mechanisms like axons in neurons, represent a means by which invaded tumor cells can communicate with their fellows over long distances, resulting in optimal functionality, efficient tumor progression, and—specifically via GAP-43—resistance to adverse events like radiotherapy (FIG. 13f). Thus, pharmacological targeting of TM formation and function adds to the attempts in finding the Achilles' heel of treatment-resistant brain tumors.

More than that, the results of the present studies imply that at least two different TM-proficient glioma cell subtypes exist: one particularly invasive with 1-2 TMs where TTYH1 is of high functional relevance, and one with multiple TMs, typically forming a dense multicellular network with other glioma cells; the latter appears uncompromised by interference with TTYH1.

First a microarray analysis comparing primary glioblastoma cells that were cultured under two different conditions in vitro (that made them TM-proficient vs. transiently TM-deficient in vivo) not only confirmed GAP-43 as a TM driver, but identified the new candidates VGF and TTYH1. From these two, only the genetic knockdown of TTYH1 produced a significant phenotype in GBMSCs in vitro and in vivo. Further confirming the validity of this screening approach, OLIG2, which was the fifth most upregulated gene under stem-like conditions, was connected before to sternness of glioblastoma cells, and also CNS development. Likewise, in a similar screen performed in 6 different primary glioblastoma cell lines, all three GAP-43, TTYH1, and OLIG2 were among the top 20 upregulated genes under stem-like vs. differentiating conditions.

TTYH1 is a membrane protein with chloride conductance and calcium-binding activity, which is normally restrictively expressed in neural tissue and the testis, particularly during development. While not much work has been published regarding TTYH1 yet, it has been implicated in neuronal structural plasticity, calcium homeostasis, and embryonic development. Interestingly, the sole overexpression of TTYH1 was sufficient to induce marked extensions of neurites, i.e. long membrane protrusions involved in the formation of axons and dendrites, in neuronal as well as non-neuronal cells, whereas the knockdown of TTYH1 led to morphological changes of protrusions described as neurite beading. The latter phenotypical change was also evident in glioma cells in vivo after TTYH1 shRNA knockdown in the present study. Later reports indicated that TTYH1 is also expressed in reactive and migrating astrocytes where it concentrated at the leading edge of filopodia, resembling the present results from subcellular distribution of TTYH1 protein in glioma cells. The basal expression in non-reactive astrocytes was low, emphasizing a more restricted function to the migratory subgroup of cells, which again is in accordance to our findings in glioma cells. Interestingly, it has been shown that neuronal activity promotes the proliferation and growth of high-grade glioma through the activity-regulated secretion of Neuroligin-3, which was associated (while not functionally verified) with increased TTYH1 expression in a gene expression screen.

Since one of the proposed functions of TTYH1 includes a $Ca^{2+}$-activated chloride channel, it is possible that it executes its pro-migratory function through its chloride-conducting properties. Gliomas accumulate chloride ions and thus create an outwardly directed chloride gradient. The chloride efflux is then followed by efflux of water, enabling the migrating cell to adjust their cell shape when migrating through narrow extracellular spaces. Chloride channel blockade or knockdown leads to reduced invasion capacity similar to the effect of the TTYH1 knockdown. The interference with chloride ion channels and transporters is currently investigated as potential therapeutic target in clinical trials. This might explain why TTYH1 plays functional roles preliminary in the TMs of the migratory 1-2 TM glioma cell subtype, while the protein is located in many TMs of all glioma cell subtypes. The observed filament beading induced by TTYH1 knockdown could be the equivalent of local cell swelling thereby hindering effective cell shape adaptation, that is crucial for cellular translocation in the dense neuropil.

Another potential mechanism of action of TTYH1 could be an interaction with pro-invasive integrins, as it has been demonstrated that TTYH1 co-localized with α5-integrin which was also seen in the GBMSCs of the present study. Integrins interact indirectly with the actin cytoskeleton, are involved in growth-cone migration and are enriched at growth-cone tips. As TTYH1 can directly interact with the cytoskeleton by binding to actin and tubulin and both cytoskeleton elements are structural components in TMs, it is possible that TTYH1 might be a mediator of the integrin-actin interactions and that the effects on the cytoskeleton are responsible for the impaired invasion in Tthy1 knockdown cells.

When comparing the quantitative impact of undisturbed TTYH1 expression on successful brain colonization with that of GAP-43, it appears that TTYH1 might be even more relevant for tumor cell invasion and overall tumor growth than GAP-43. In fact, the findings of this study suggest a particular involvement of TTYH1 in the extension and function of dynamic TMs from migratory glioma cells. The present results also demonstrate that knockdown of TTYH1 in three different GBMSC lines was lethal for one of them in vitro, largely lethal for one of them in vivo, and strongly decreased in vivo growth in the third (S24). This supports a crucial impact of proficient TTYH1 expression on cell viability, or at least the ability to colonize the brain in different gliomas. In contrast, unlike GAP-43, its knockdown even increased the relative number of highly TM-interconnected, more stationary glioma cells in S24 GBMSCs. One can speculate that the small size and the invasive deficit of the TTYH1 knockdown tumors might facilitate the interconnection of neighboring tumor cells with TMs, using TTYH1-independent machineries like GAP-43 for the formation of this TM subtype. Finally, the results of this study support the finding that TM-interconnected glioma cells build the resistant backbone of the brain tumor that is not relevantly affected by the adverse effects of radiotherapy—no matter how invasion-deficient and small the tumor is.

In conclusion, next to GAP-43, TTYH1 is a novel important molecular driver of distinct TM functions that has mainly been associated with CNS development and repair so far. It also provides important additional information about TM-associated tumor cell heterogeneity in gliomas, pointing towards the necessity of distinct therapeutic strategies to target different tumor cell subtypes. Both TM-associated tumor cell subtypes with their intrinsic features of diffuse infiltration (1-2 TMs) vs. high therapy resistance (multiple TMs) appear to contribute to the current poor prognosis of malignant astrocytomas. Thus, the question how and when to target which TMs is probably the translationally most important. In contrast to GAP-43, inhibition of which appears to be most promising during radiotherapy, the most promising therapeutic window for TTYH1 inhibition could be after completion of standard cytotoxic therapy, or even instead of; combination with radiotherapy should be avoided. The strong anti-invasive and anti-proliferative effects of the genetic TTYH1 knockdown, however, and the potentially limited importance for the adult non-malignant CNS make TTYH1 an interesting target for future drug development.

The invention claimed is:

1. A method for the treatment of glioma in a subject, wherein said method comprises the step of administering to a subject in need thereof an agent capable of interfering with tumor microtube (TM)-mediated (a) invasion and/or (b) proliferation and/or (c) intracellular communication and/or (d) resistance to radiotherapy and/or chemotherapy of glioma cells, wherein said agent is an agent capable of mediating RNAi for the specific knockdown of the human tweety homologue 1 (Ttyh 1) gene and is targeted at one of the nucleic acid sequences laid out in SEQ ID NOs: 12-16.

* * * * *